(12) United States Patent
Messick et al.

(10) Patent No.: US 12,116,359 B2
(45) Date of Patent: Oct. 15, 2024

(54) EBNA1 INHIBITOR CRYSTALLINE FORMS, AND METHODS OF PREPARING AND USING SAME

(71) Applicant: THE WISTAR INSTITUTE, Philadelphia, PA (US)

(72) Inventors: Troy E. Messick, Upper Darby, PA (US); Paul M. Lieberman, Wynnewood, PA (US); Garry R. Smith, Elverson, PA (US); Arlindo L. Castelhano, New York, NY (US)

(73) Assignee: The Wistar Institute, Philadelphia, PA (US)

( * ) Notice: Subject to any disclaimer, the term of this patent is extended or adjusted under 35 U.S.C. 154(b) by 0 days.

(21) Appl. No.: 17/896,767

(22) Filed: Aug. 26, 2022

(65) Prior Publication Data

US 2023/0103362 A1 Apr. 6, 2023

Related U.S. Application Data

(63) Continuation of application No. 17/576,018, filed on Jan. 14, 2022, now abandoned, which is a continuation of application No. 16/414,198, filed on May 16, 2019, now Pat. No. 11,242,338.

(60) Provisional application No. 62/672,743, filed on May 17, 2018.

(51) Int. Cl.
| | |
|---|---|
| *C07D 405/12* | (2006.01) |
| *A61K 31/404* | (2006.01) |
| *A61K 45/06* | (2006.01) |
| *A61P 25/28* | (2006.01) |
| *A61P 31/22* | (2006.01) |
| *A61P 35/02* | (2006.01) |
| *A61K 9/00* | (2006.01) |

(52) U.S. Cl.
CPC .......... *C07D 405/12* (2013.01); *A61K 31/404* (2013.01); *A61P 25/28* (2018.01); *A61P 31/22* (2018.01); *A61P 35/02* (2018.01); *A61K 9/0053* (2013.01); *A61K 45/06* (2013.01); *C07B 2200/13* (2013.01)

(58) Field of Classification Search
CPC ............. C07D 405/12; C07B 2200/13; A61K 31/404; A61K 9/0053; A61K 45/06; A61P 25/28; A61P 31/22; A61P 35/02
See application file for complete search history.

(56) References Cited

U.S. PATENT DOCUMENTS

| | | | |
|---|---|---|---|
| 4,638,002 A | 1/1987 | Szekely et al. | |
| 5,155,248 A | 10/1992 | Ullrich et al. | |
| 5,185,454 A | 2/1993 | Bader et al. | |
| 5,356,919 A | 10/1994 | Djuric et al. | |
| 6,166,028 A | 12/2000 | Bloom et al. | |
| 6,811,983 B2 | 11/2004 | Sugden et al. | |
| 9,469,673 B2 | 10/2016 | Sheikh et al. | |
| 10,442,763 B2 * | 10/2019 | Messick | A61K 31/5377 |
| 10,981,867 B2 | 4/2021 | Messick et al. | |
| 2003/0032623 A1 | 2/2003 | Ban et al. | |
| 2003/0199511 A1 | 10/2003 | Li et al. | |
| 2004/0044041 A1 | 3/2004 | Kuduk et al. | |
| 2006/0030613 A1 | 2/2006 | Conte-Mayweg et al. | |
| 2006/0258645 A1 | 11/2006 | Failli et al. | |
| 2008/0153802 A1 | 6/2008 | Lessene et al. | |
| 2009/0171091 A1 | 7/2009 | Thombare et al. | |
| 2011/0009447 A1 | 1/2011 | Huth et al. | |
| 2013/0040949 A1 | 2/2013 | Gray et al. | |
| 2014/0113897 A1 | 4/2014 | Lieberman et al. | |
| 2018/0086699 A1 | 3/2018 | Messick et al. | |

FOREIGN PATENT DOCUMENTS

| | | |
|---|---|---|
| CN | 1634810 A | 7/2005 |
| CN | 103476770 A | 12/2013 |
| JP | 4991532 B2 | 8/2012 |
| JP | 6223336 B2 | 11/2017 |
| WO | 0153274 A1 | 7/2001 |
| WO | 0190101 A1 | 11/2001 |
| WO | WO2003024913 | 3/2003 |
| WO | 2006019831 A1 | 2/2006 |
| WO | 2006055070 A2 | 5/2006 |
| WO | 2007002433 A1 | 1/2007 |
| WO | 2007002587 A2 | 1/2007 |
| WO | 2007023242 A1 | 3/2007 |
| WO | 2010048332 A2 | 4/2010 |
| WO | 2010092043 A1 | 8/2010 |
| WO | 2010100475 A1 | 9/2010 |
| WO | 2010118009 A1 | 10/2010 |
| WO | 2010124047 A1 | 10/2010 |
| WO | 2010127440 A1 | 11/2010 |

(Continued)

OTHER PUBLICATIONS

Soldan et al., Gastric Cancer, 2021, 24, 1076-1088.*
Epstein-barr-virus, 2024, https://www.webmd.com/a-to-z-guides/epstein-barr-virus.*
MS, 2024, https://www.mayoclinic.org/diseases-conditions/multiple-sclerosis/diagnosis-treatment/drc-20350274.*
Bendele, "Animal Models of Arthritis: Relevance to Human Disease", Toxicol Pathol 1999, 27:134-142.
Bendele, "Animal models of rheumatoid arthritis", J Musculoskel Neuron Interact 2001; 1(4):377-385.

(Continued)

*Primary Examiner* — Sun Jae Yoo
(74) *Attorney, Agent, or Firm* — Kathryn Doyle; Domingos J. Silva; Saul Ewing LLP

(57) ABSTRACT

The invention relates, in certain aspects, to developable forms of certain compounds that are useful to treat and/or prevent EBV infection and related conditions in a subject. The invention further provides EBNA1 inhibitors, and/or pharmaceutical compositions comprising the same, that are useful for the treatment of diseases caused by latent Epstein-Barr Virus (EBV) infection and/or lytic EBV infection.

10 Claims, 35 Drawing Sheets

(56) References Cited

FOREIGN PATENT DOCUMENTS

| WO | 2011082098 A1 | 7/2011 |
| WO | 2011090911 A1 | 7/2011 |
| WO | 2012098416 A1 | 7/2012 |
| WO | 2012162291 A1 | 11/2012 |
| WO | 2014145022 A1 | 9/2014 |
| WO | 2015073864 A1 | 5/2015 |
| WO | 2016183534 A1 | 11/2016 |

OTHER PUBLICATIONS

Chaichian, "Targeted Therapies in Systemic Lupus Erythematosus: A State-of-the-Art Review", J Clin Cell Immunol 2013, S6, 1-8.
Costenbader, "Epstein-Barr virus and rheumatoid arthritis: is there a link?", Arthritis Research & Therapy, vol. 8, No. 1, pp. 1-7.
Damia, "Contemporary pre-clinical development of anticancer agents—What are the optimal pre-clinical models?". European Journal of Cancer 2009, 45, 2768-2781.
Johnson, et al., "Relationships between drug activity in NCI preclinical in vitro and in vivo models and early clinical trials", British Journal of Cancer 2001, 84, 1424-1431.
Ledford, "US cancer institute overhauls cell lines", Nature. Feb. 25, 2016, vol. 530, p. 391.
Mahieu, "A critical review of clinical trials in systemic lupus erythematosus", Lupus (2016) 25, 1122-1140.
Munger, "No association of multiple sclerosis activity and progression with EBV or tobacco use in Benefit", Neurology (2015), 85(19), 1694-1701.
Munz, "Epstein Barr Virus vol. 1 One Herpes Virus: Many Diseases", Current Topics in Microbiology and Immunology Springer Cham: Heidelberg New York Dordrecht London, 2015.
Ocana, "Preclinical development of molecular targeted agents for cancer", Nat. Rev. Clin. Oneal. 2011, 8, 200-209.
Pilz, "Modern multiple sclerosis treatment—what is approved, what is on the horizon", Drug Discovery Today Dec. 2008, vol. 13, Nos. 23/24, 1013-1025.
Sharma, "Cell line-based platforms to evaluate the therapeutic efficacy of candidate anticancer agents", Nature Reviews Cancer, Apr. 2010, vol. 10, 241-253.
Thompson, "Development of a High-Throughput Screen for Inhibitors of Epstein-Barr Virus EBNA1", Journal of Biomolecular Screening, 15(9); 2010, pp. 1107-1115.
International Search Report and Written Opinion dated Jul. 23, 2019, PCT/US2019/032623.
Supplemental European Search Report dated Nov. 9, 2021, EP Application No. 19804410.9.
Byrn, et al., "Pharmaceutical Solids: A Strategic Approach to Regulatory Considerations", Pharmaceutical Research, vol. 12, No. 7, Jul. 1, 1995, pp. 945-954.
Caira, et al., "Crystalline Polymorphism of Organic Compounds", Topics in Current Chemistry, Springer, Berlin, DE, vol. 198, Jan. 1, 1998 (Jan. 1, 1998), pp. 163-208, XP008166276, ISSN: 0340-1022.
Sun, et al., "Stability of Amorphous Pharmaceutical Solids: Crystal Growth Mechanisms and Effect of Polymer Additives", The AAPS Journal, vol. 14, No. 3, Sep. 2012 (# 2012) DOI: 10.1208/s12248-012-9345-6.
Vranić E., "Amorphous pharmaceutical solids," Bosn J Basic Med Sci. Jul. 2004;4(3):35-9. doi: 10.17305/bjbms.2004.3383. PMID: 15629010; PMCID: PMC7245478.
Chemotherapy, 2021, https://www.webmd.com/cancer/how-chemo-works#1-4.
MultipleSclerosis, 2021, https://www.webmd.com/cancer/how-chemo-works#1-4.

PubChem. Compound Summary for: CID 1962039. Create Date: Dec. 5, 2007 [retrieved on Mar. 31, 2015]. Retrieved from the Internet: <URL: https//pubchem.ncbi.nlm.nih.gov/compound/19612039>. entire document.
STN registration file RN 873330-62.2, 2006.
STN Registry 178742-95-5, 1996.
STN Registry RN 10601-99-7, 1984.
STN Registry RN 1244017-13-7, 2010.
Bochkarev, et al., "Crystal Structure of the DNA-Binding Domain of the Epstein-Barr Virus Origin-Binding Protein, EBNA1, Bound to DNA", 1996, Cell 84:791-800.
Crawford, et al., "The Preparation of Some Alkyl-substituted Benxoic Acids", Jan. 1, 1952—Retrieved from the Internet: URL:http://pubs.rsc.org/en/content/articlepdf/1952/jr/jr9520004443 [retrieved on Apr. 7, 2017].
Deakyne, et al., "Stuctural and Functional Basis for an EBNA1 Hexameric Ring in Epstein-Barr Virus Episome Maintenance.", 2017, J. Virol 91(19)e01046-17 (17 pages) Jul. 12, 2017.
Dheekollu, et al., "Carcinoma-risk variant of EBNA1 deregulates Epstein-Barr Virus episomal latency.", 2017, Oncotarget 8(5):7248-7264.
Faigl, et al., "Organometallic Approach to the Functionalization of Alkyl Groups Containing 1-Phenylpyrroles.", 2006, Synthetic Communications 36:2841-2849 Abstract.
Gao, et al., "Discovery and Optimization of 3-(2-(Pyrazolo[1,5-a]pyrimidin-6-yl) ethynyl)benzamides as Novel Selective and Orally Bioavailable Discoidin Domain Receptor 1 (DDR1) Inhibitors", J. Med. Chem., 2013, 56 (8), pp. 3281-3295 (Abstract).
Ghosh, et al., "Histone deacetylase inhibitors are potent inducers of gene expression in latent EBV and sensitize lymphoma cells to nucleoside antiviral agents.", 2012, Blood 119(4):1008-1017.
Kim, et al., "Palladium-Catalyzed Domino Cyclization (5-exo/3-exo), Ring-Expansion by Palladium Rearrangement, and Aromatization: An Expedient Synthesis of 4-Arylnicotinates from Morita-Baylis-Hillman Adducts.", 2013, Advanced Synthesis & Catalysis 355:1977-1983 Abstract.
Li, et al., "Discover of selective inhibitors agains EBNA1 via high throughput in silico virtual screening.", PLoS One, Apr. 12, 2010, vol. 5, No. 4, pp. e10126.
Liu, et al., "Studies of Phenylethynyl-pyrrolo[1,2-a]pyrazine as mGluR5 Antagonists Using 3D-QSAR Method", Asian Journal of Chemistry: vol. 24, No. 1 (2012), 238-248.
Martin, et al., "Do Structurally Similar Molecules Have Similar Biological Activity?", 2002 J Chem Med 45:4350-4358.
Newman, et al., "The Synthesis of 6,6'-Diethynyldiphenic Anhydride.", 1971, J Org Chem 36(10:1398-1401.
Penning, et al., "Structure-Activity Relationship Studies on 1-[2-(4-Phenylphenoxy)ethyl]pyrrolidine (SC-22716), a Potent Inhibitor of Leukotriene A4 (LTA4) Hydrolase.", 2000, J Med Chem 43:721-735.
Shimakage, et al., "Significant role of macrophages in human cancers associate with Epstein-Barr virus (Review)."; Oncology Reports 32:1763-1771, 2014.
Thompson, et al., "Development of a High-Throughput Screen for Inhibitors of Epstein-Barr Virus EBNA1", Journal of Biomolecular Screening 15(9); 2010 pp. 1107-1115.
European Search Report dated Jun. 30, 2023, EP Application No. 19804410.9.
Aaltonen, et al., "Solid form screening—A review", European Journal of Pharmaceutics and Biopharmaceutics, vol. 71, No. 1, pp. 23-37 (2009).
Yu, L., "Amorphous Pharmaceutical Solids: Preparation, Characterization and Stabilization", Advanced Drug Delivery Reviews, vol. 48, No. 1, pp. 27-42 (2001).

* cited by examiner

EBNA1 INHIBITOR CRYSTALLINE FORMS, AND METHODS OF PREPARING AND USING SAME

CROSS-REFERENCE TO RELATED APPLICATIONS

The present application is a continuation of, and claims priority to, U.S. patent application Ser. No. 17/576,018, filed Jan. 14, 2022, which is a continuation of U.S. patent application Ser. No. 16/414,198, filed May 16, 2019, now issued as U.S. Pat. No. 11,242,338, which claims priority under 35 U.S.C. § 119(e) to U.S. Provisional Patent Application No. 62/672,743, filed May 17, 2018, all of which applications are incorporated by reference herein in their entireties.

STATEMENT REGARDING FEDERALLY SPONSORED RESEARCH OR DEVELOPMENT

This invention was made with government support under grant number 5 R43 AI079928 and 1 R21 NS063906 awarded by the National Institutes of Health. The government has certain rights in the invention.

BACKGROUND OF THE INVENTION

EBV is a human gamma-herpesvirus that infects over 90% of the adult population worldwide. In combination with known and unknown cofactors, especially immunosuppression, EBV infection constitutes a high carcinogenic risk. EBV has been classified by the World Health Organization as a class I human carcinogen because of its causal association with Burkitt's lymphoma, nasopharyngeal carcinoma, about 50% of all Hodgkin's lymphoma, gastric carcinoma, angiocentric T/NK lymphoma, and lymphoproliferative disorders of the immunosuppressed. EBV is responsible for about 1% of all human cancers, worldwide. The oncogenic potential of EBV is readily demonstrated in vitro by its capacity to immortalize primary B-lymphocytes in culture, and in vivo by its ability to drive infected B-cells into aggressive lymphoblastic lymphomas in immunocompromised hosts.

EBV, like other herpesviruses, has a latent and lytic replication cycle. While the EBV lytic cycle is essential for viral transmission and increases risk of EBV-associated malignancy, it is the latent viral infection that is oncogenic. The latent virus expresses a limited set of viral genes that stimulate cellular proliferation and survival. Clinically available inhibitors of herpesvirus DNA polymerases, including variants of acyclovir (e.g., ganciclovir) and phosphonoacetic acid (e.g., foscarnet) have at least partial inhibitory activity against EBV lytic replication. However, none of the available herpesvirus antivirals are effective at blocking the virus from progressing to a latent infection or eliminating latent infection. Primary infections with EBV can evoke a robust, sometimes debilitating immune response referred to as infectious mononucleosis (IM). Despite this robust immune reaction, the virus efficiently establishes latent infection in B-lymphocytes, where the virus can reside in long-lived memory B-cells. In some circumstances, latent infection can also be established in T-lymphocytes and epithelial cells. During latency, the virus does not produce infectious particles, and viral gene expression is limited to a subset of transcripts with growth-transforming and anti-apoptotic functions that contribute to EBV carcinogenesis. Thus, no existing anti-viral drug or immunological response can block the establishment of an EBV latent infection, which has the potential to drive lymphoid and epithelial cell oncogenic growth transformation.

There is thus a need to identify developable compounds that can be used to effectively treat and/or prevent EBV infection in a subject. Such compounds should be useful for treating and/or preventing subjects afflicted with diseases and conditions associated with EBV infection, and/or subjects that are refractory to current treatments for infectious mononucleosis, chronic fatigue syndrome, multiple sclerosis, systemic lupus erythematosus, and/or rheumatoid arthritis. Such compounds should be easily and reproducibly prepared in large scale, so that they can be used to treat large number of patients infected with EBV, or at risk on being infected with EBV. The present invention addresses this need.

BRIEF SUMMARY OF THE INVENTION

The present disclosure provides 2-(1H-Indol-6-yl)-3-[4-(tetrahydro-pyran-4-yloxymethyl)-phenylethynyl]-benzoic acid (I) free acid crystalline solid, which is characterized by one of certain X-ray powder diffraction (XRPD) patterns. The present disclosure further provides pharmaceutical compositions comprising at least one pharmaceutically acceptable carrier and any of the crystalline solids contemplated herein. The present disclosure further provides a method of treating and/or preventing a disease or disorder caused by EBNA1 activity in a subject. In certain embodiments, the method comprises administering to the subject a therapeutically effective amount of any of the solids contemplated herein and/or any of the pharmaceutical compositions contemplated herein. The present disclosure further provides a method of treating and/or preventing Epstein-Barr Virus (EBV) infection, and/or a disease or disorder associated with EBV infection, in a subject. In certain embodiments, the method comprises administering to the subject a therapeutically effective amount of any of the solids contemplated herein and/or any of the pharmaceutical compositions contemplated herein. The present disclosure further provides a method of treating and/or preventing lytic and/or latent EBV infection in a subject. In certain embodiments, the method comprises administering to the subject a therapeutically effective amount of any of the solids contemplated herein and/or any of the pharmaceutical compositions contemplated herein.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

(from crystallization in nitromethane); e. Crystalline Pattern 2 (from crystallization in toluene). See also representative peak listings in Table 15.

Figure 1:
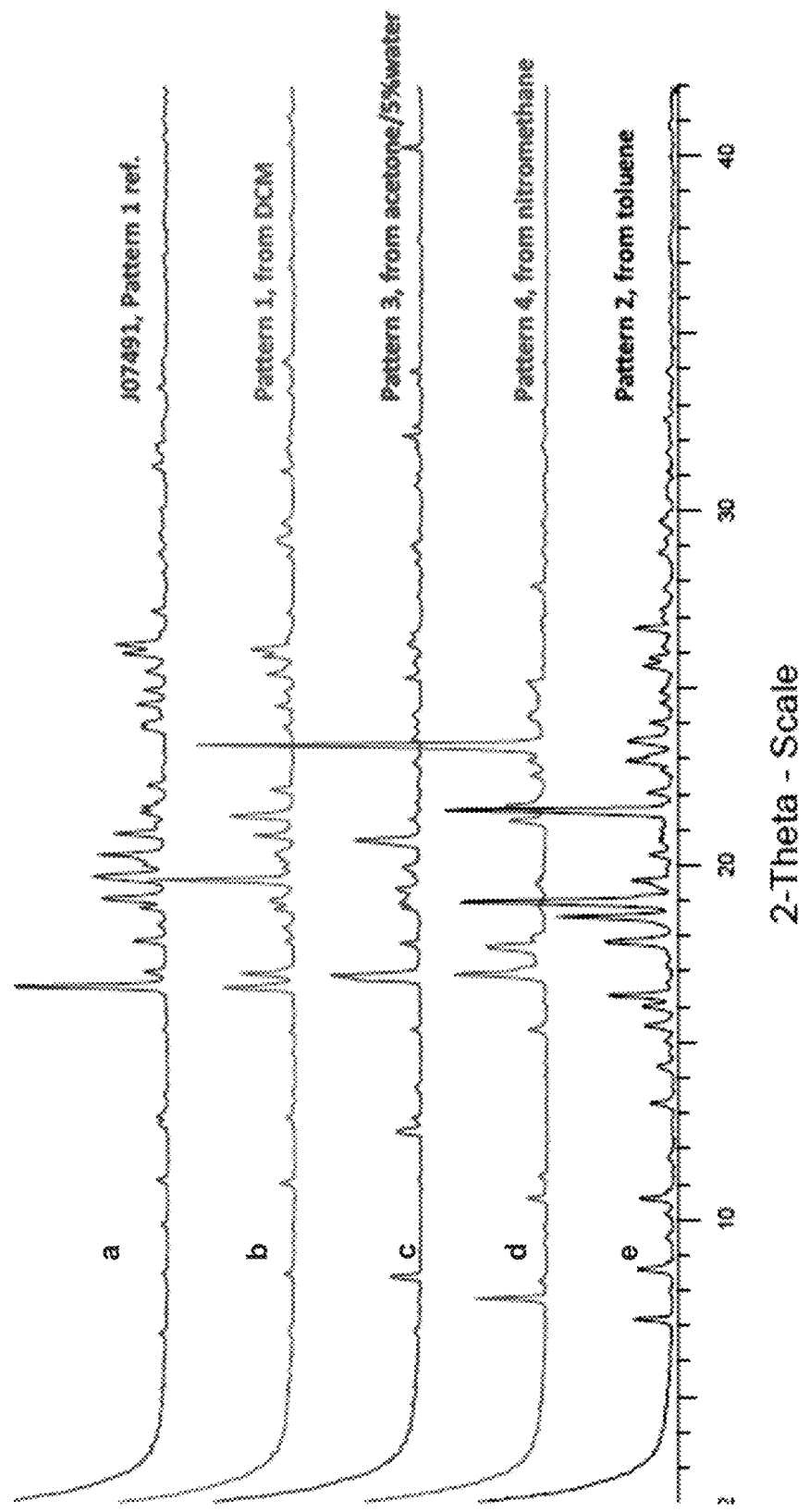
FIG. 1 illustrates XRPD traces of crystalline forms of 2-(1H-Indol-6-yl)-3-[4-(tetrahydro-pyran-4-yloxymethyl)-phenylethynyl]-benzoic acid (I) free acid obtained through screening. From top to bottom: a. Crystalline Pattern 1 (as originally obtained from crystallization in dichloromethane, DCM); b. Crystalline Pattern 1 (as obtained from de novo crystallization in DCM); c. Crystalline Pattern 3 (from crystallization in acetone/water); d. Crystalline Pattern 4
Figure 2:
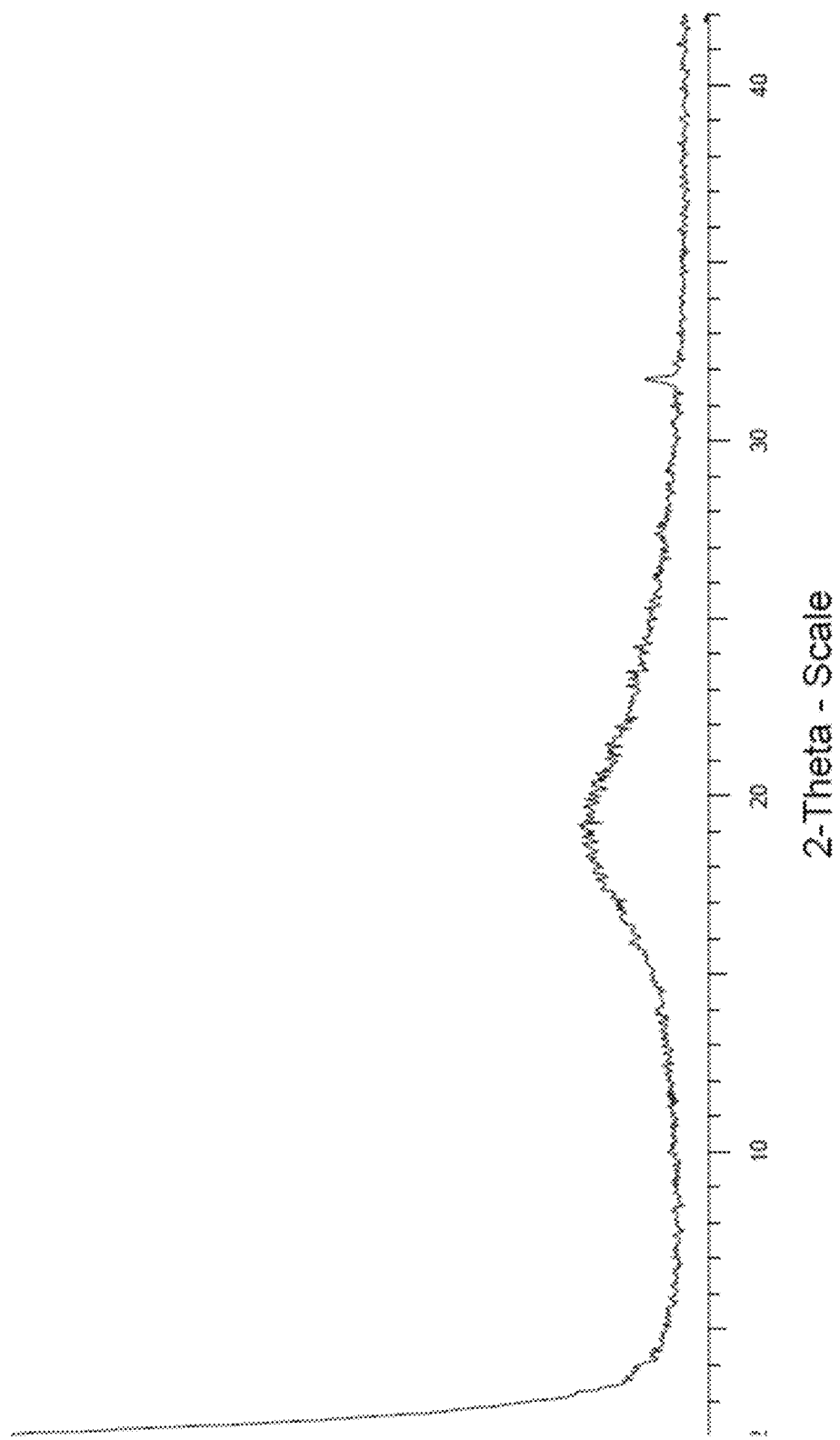

FIG. 2 illustrates a XRPD trace of amorphous (I) free acid. The small peak at about 32° was assigned to a NaCl impurity.

Figure 3:
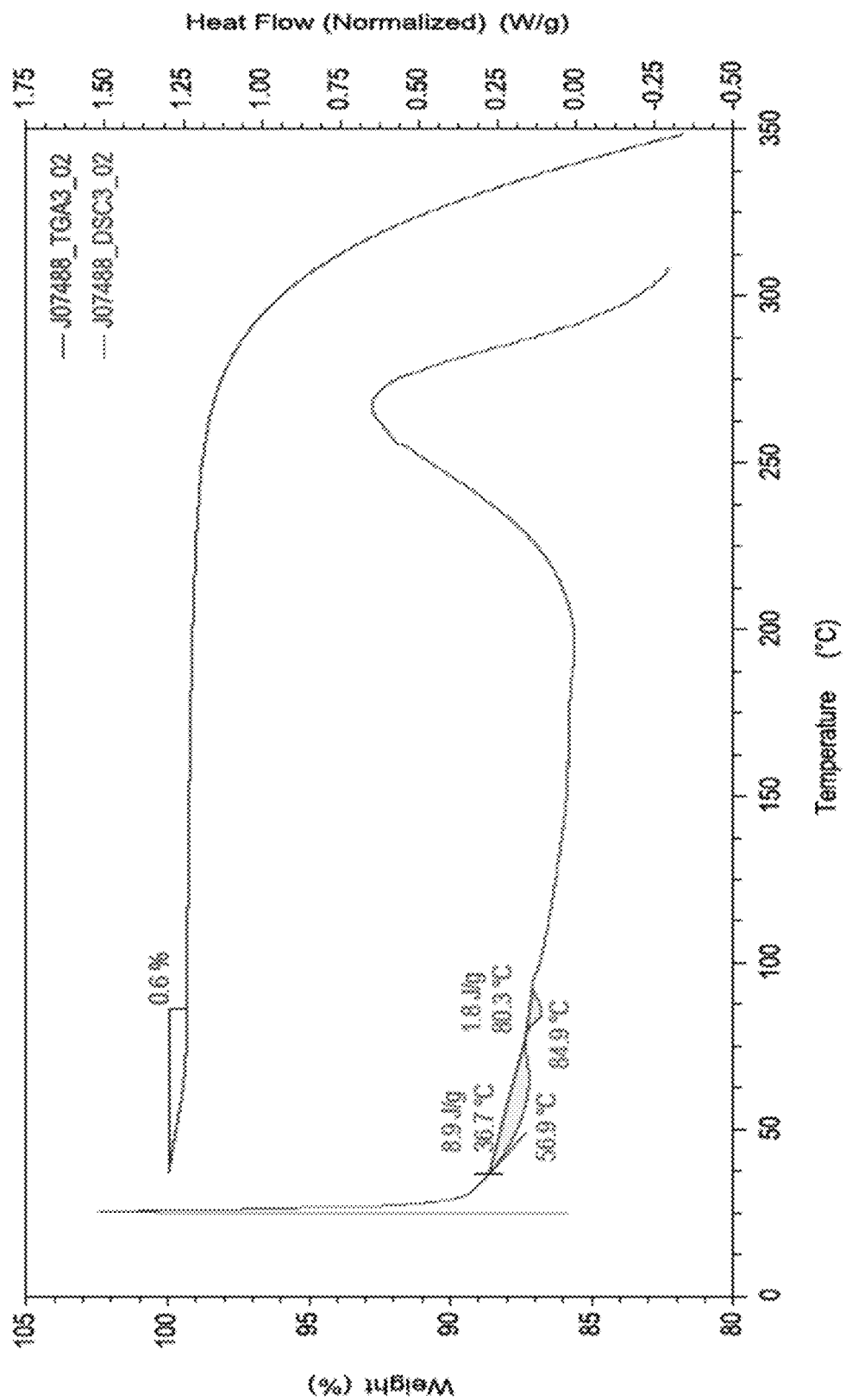

FIG. 3 illustrates TGA and DSC traces of amorphous (I) free acid.

Figure 4:
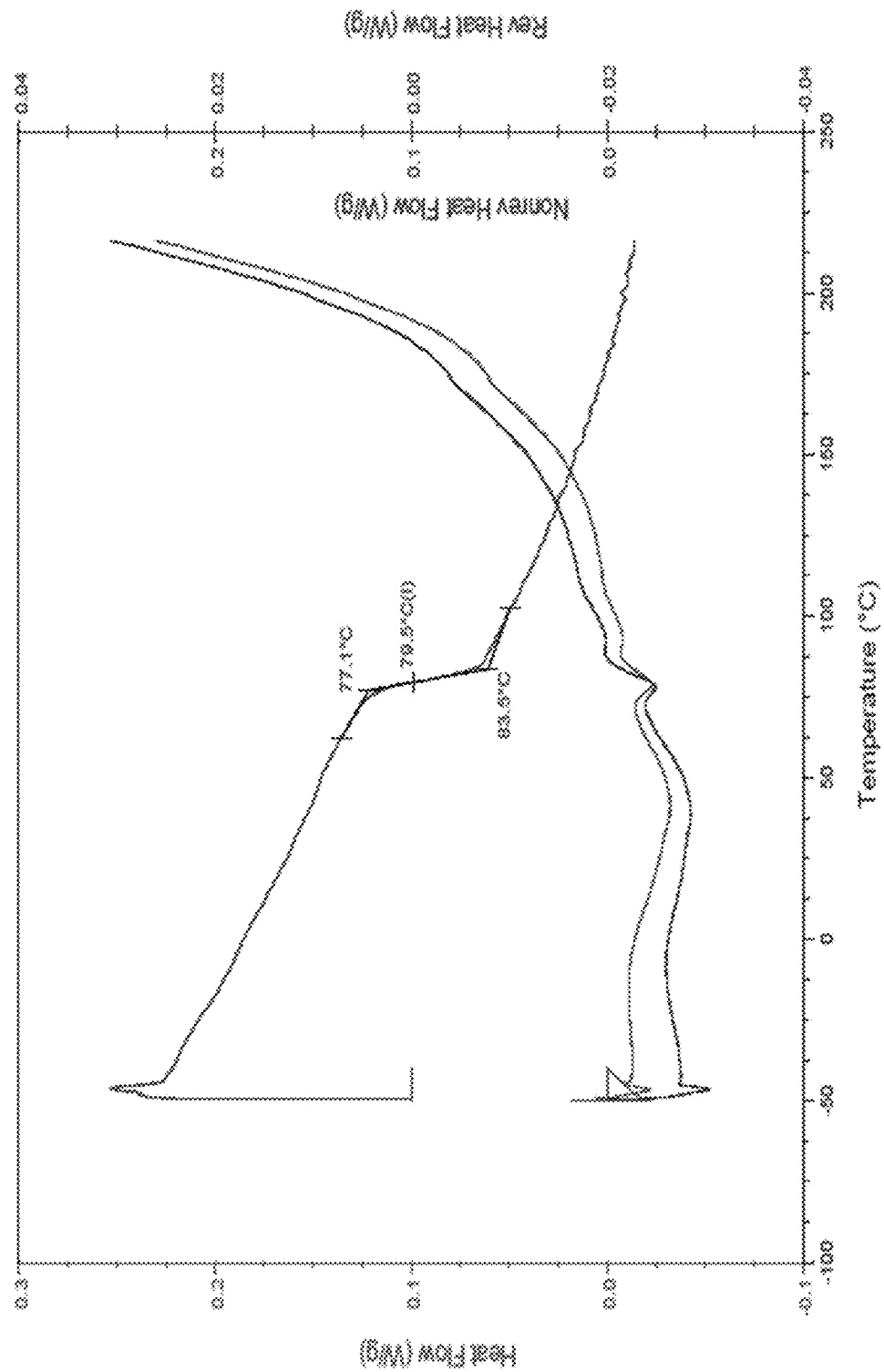

FIG. 4 illustrates MDSC traces of amorphous (I) free acid.

Figure 5:
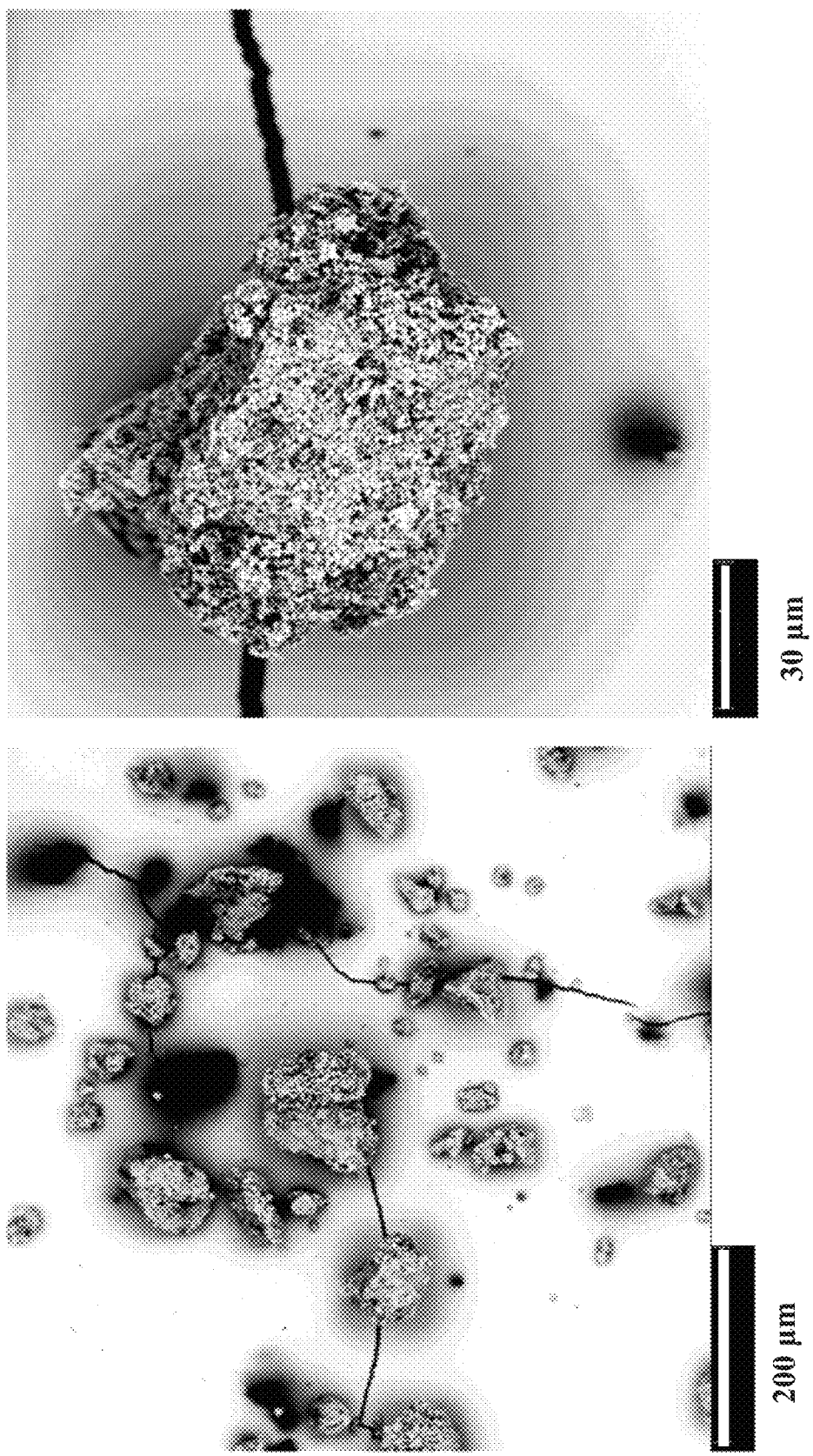

FIG. 5 illustrates SEM images of amorphous (I) free base.

Figure 6:
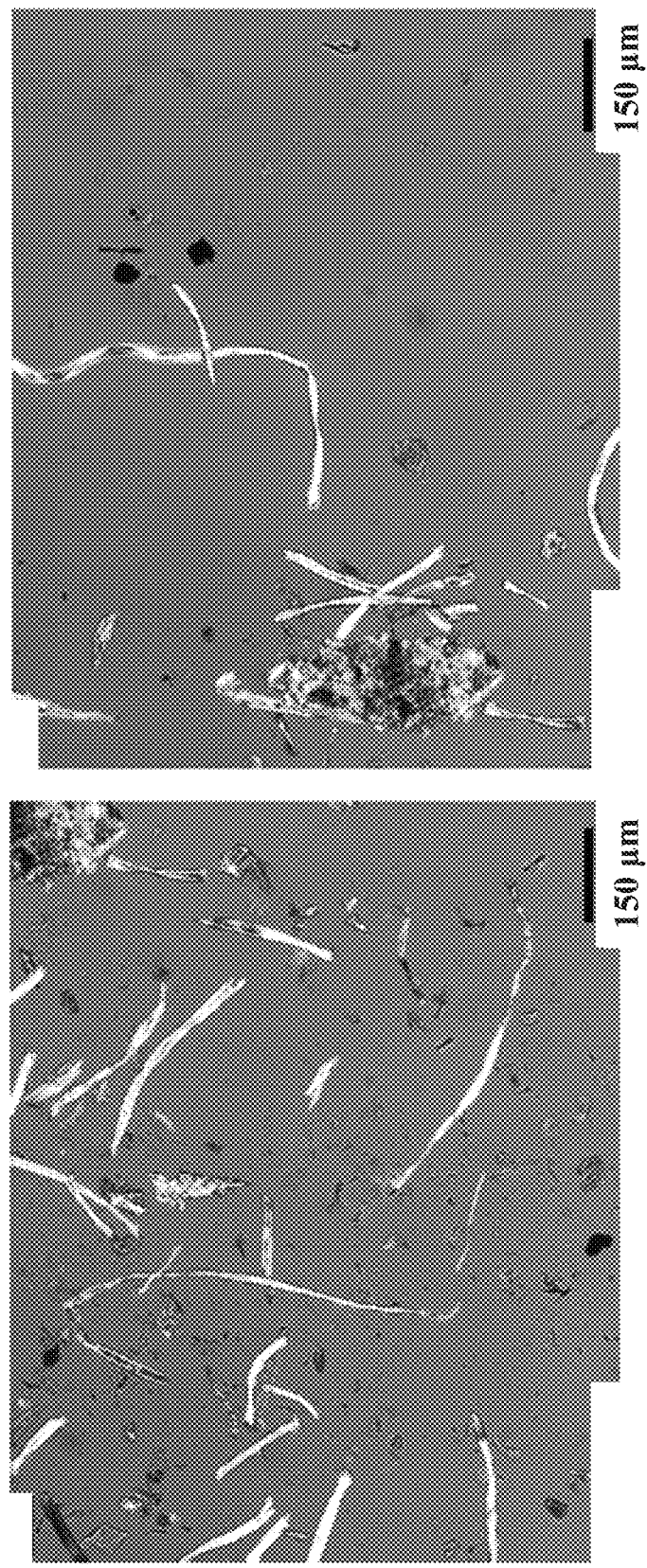

FIG. 6 illustrates optical images of amorphous (I) free acid.

Figure 7:
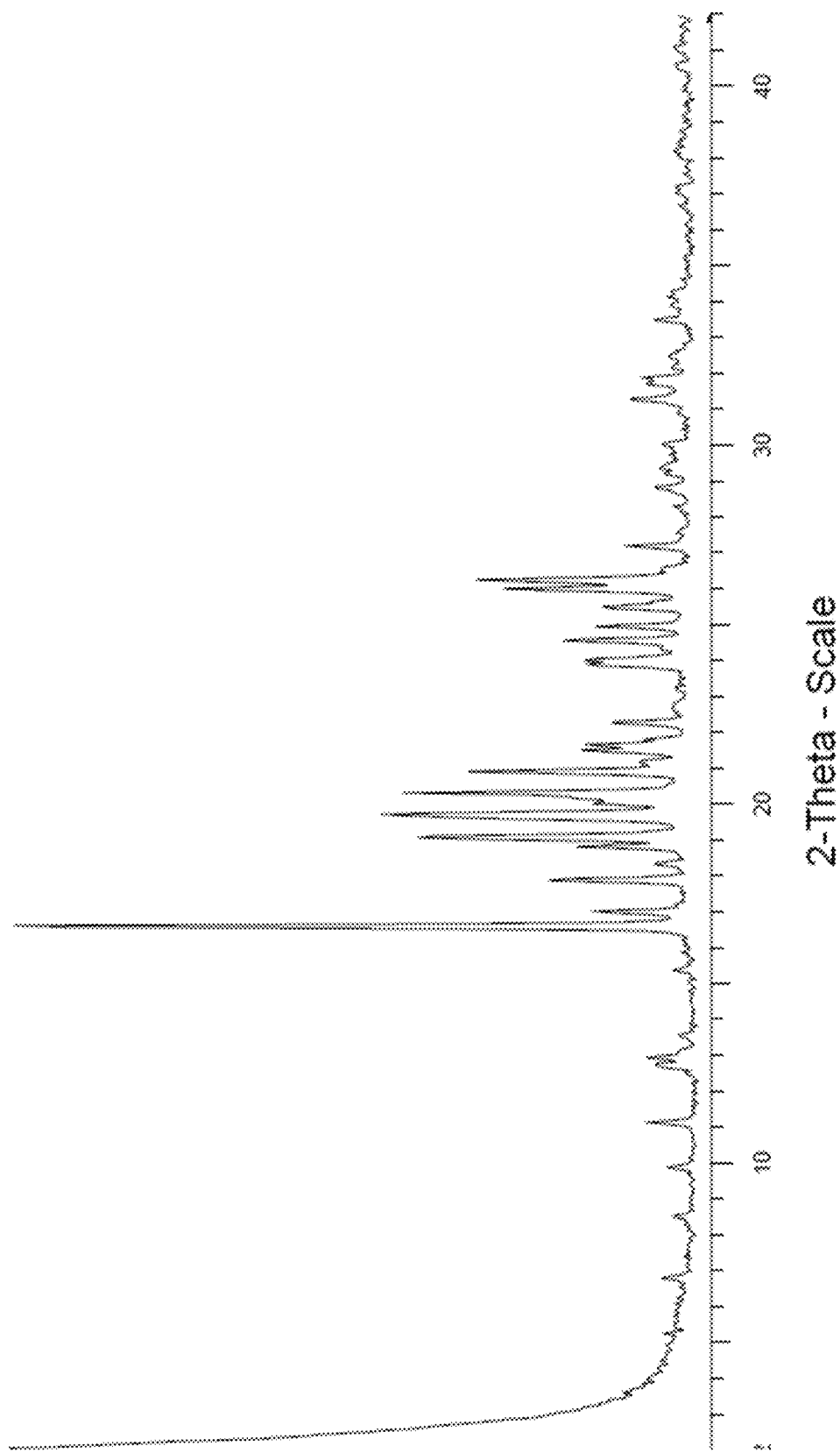

FIG. 7 illustrates a XRPD trace of Crystalline Pattern 1 of (I) free acid.

Figure 8:
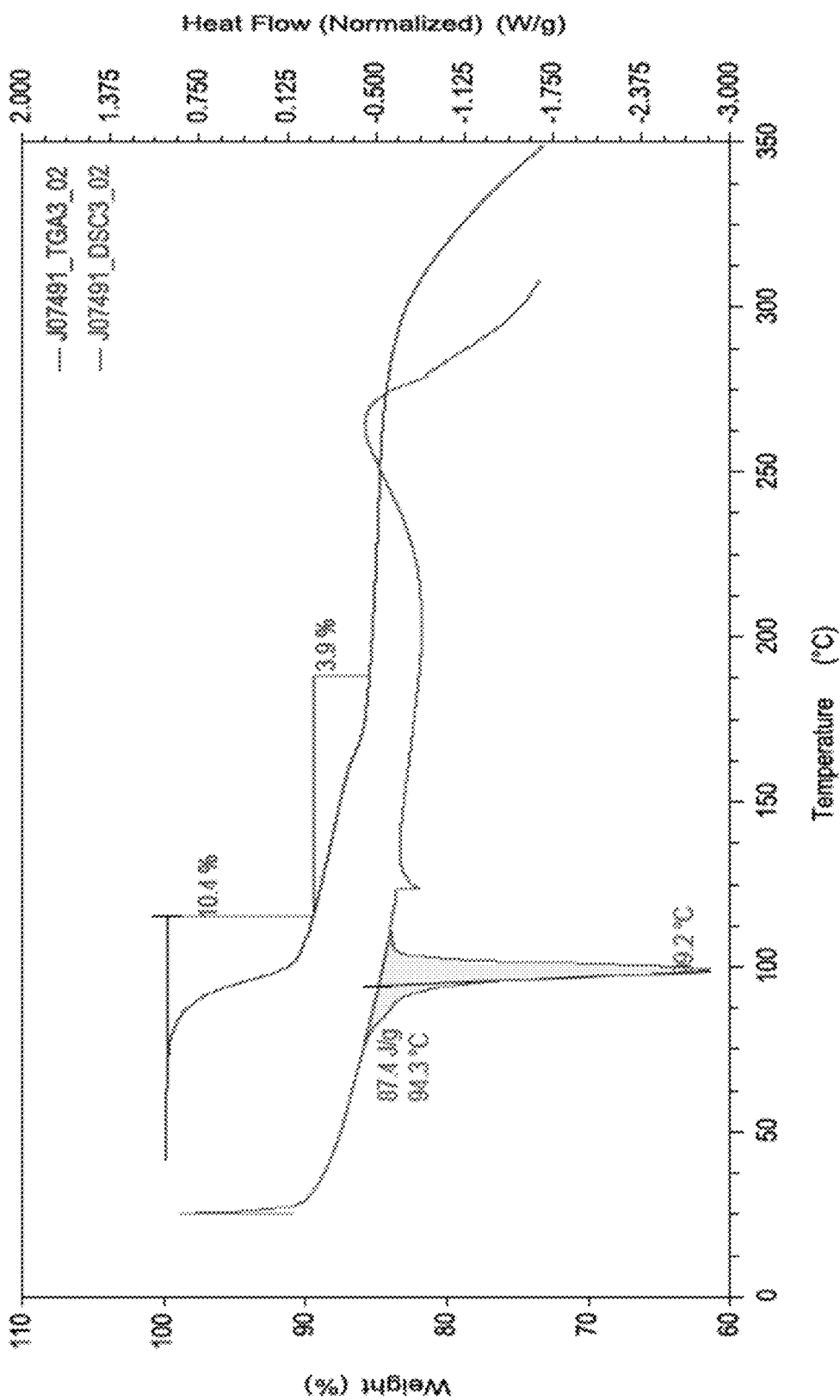

FIG. 8 illustrates TGA and DSC traces of Crystalline Pattern 1 of (I) free acid.

Figure 9:
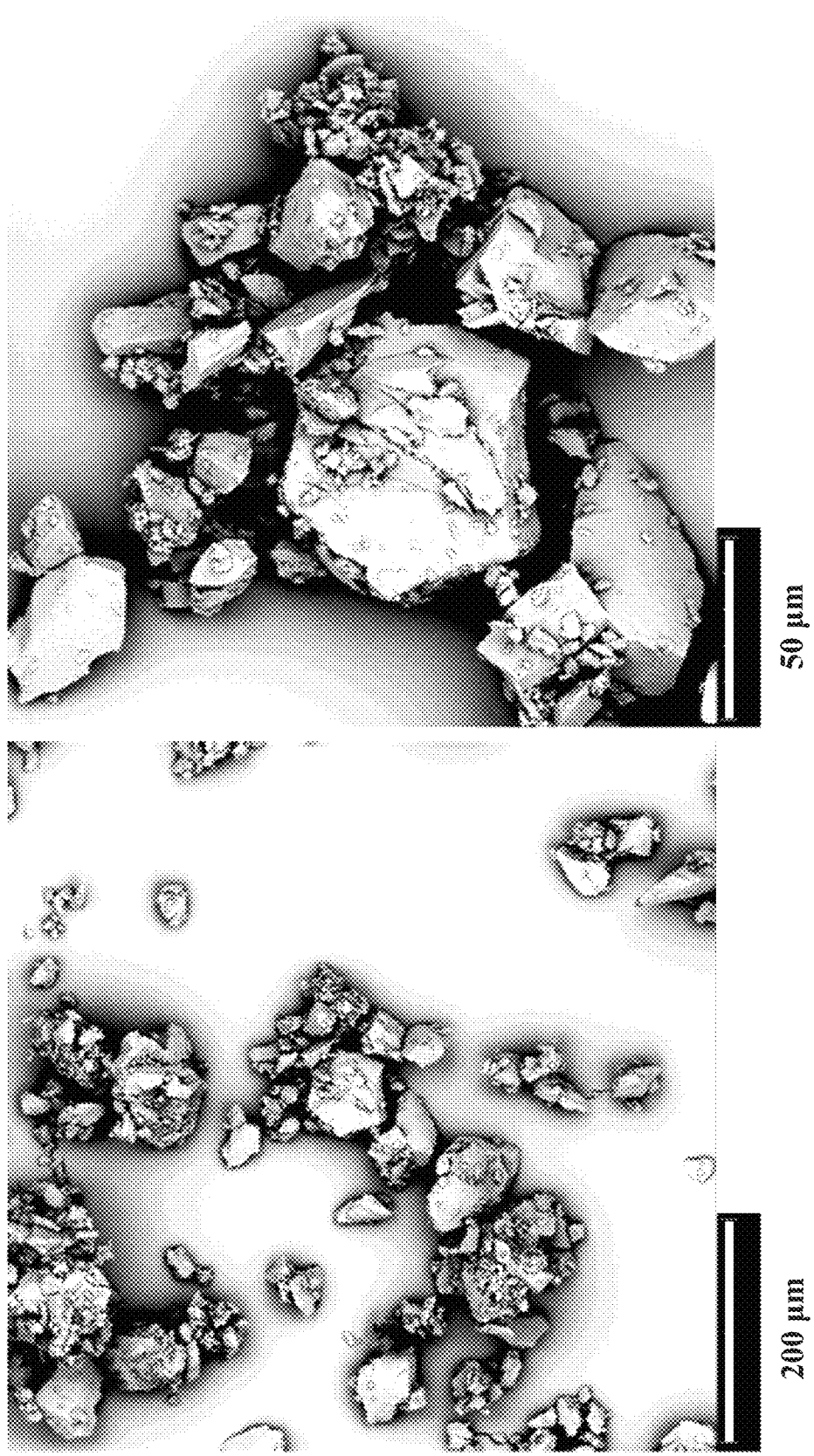

FIG. 9 illustrates SEM images of Crystalline Pattern 1 of (I) free acid.

Figure 10:
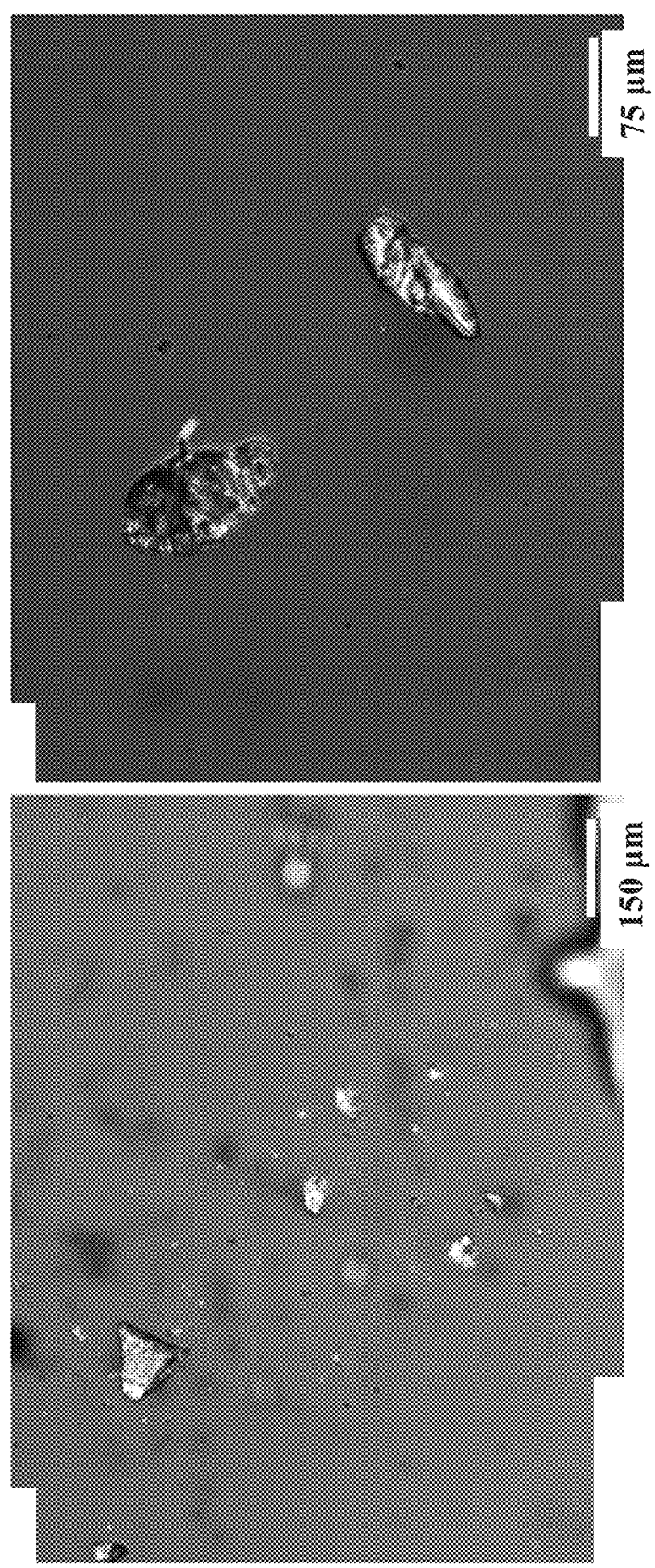

FIG. 10 illustrates optical images of Crystalline Pattern 1 of (I) free acid.

Figure 11:
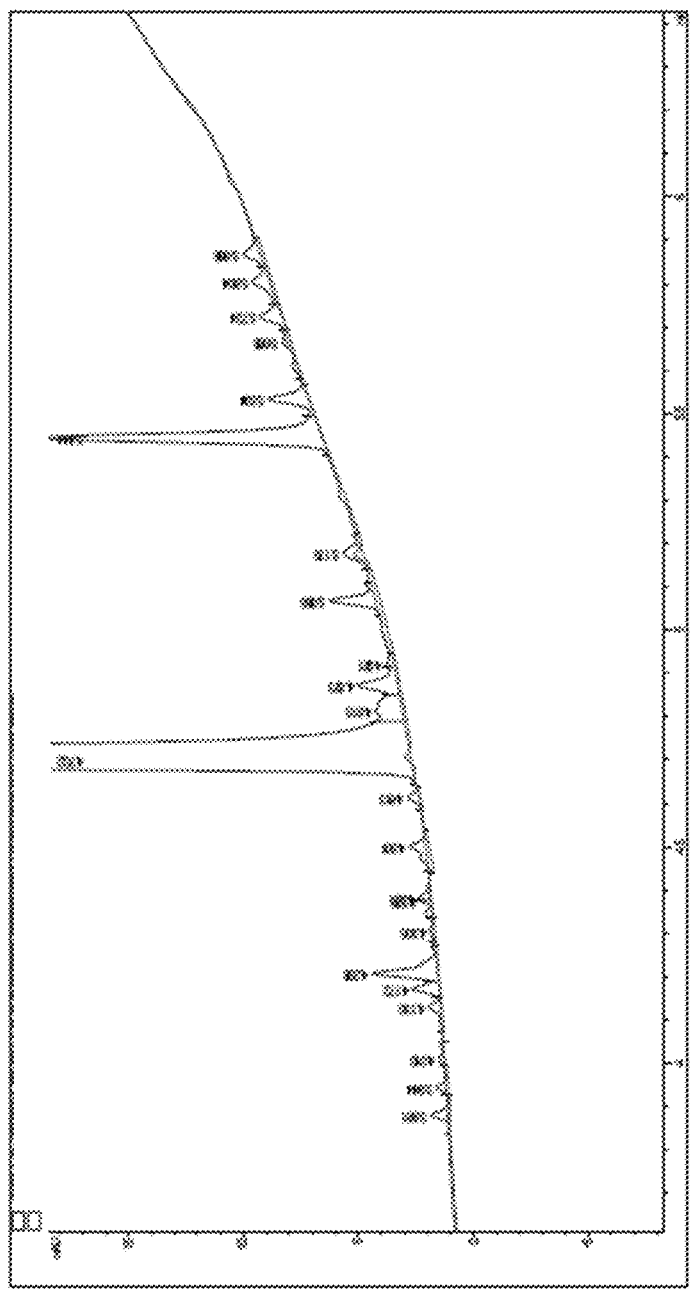

FIG. 11 illustrates a HPLC analysis trace for Crystalline Pattern 1 of (I) free acid.

Figure 12:
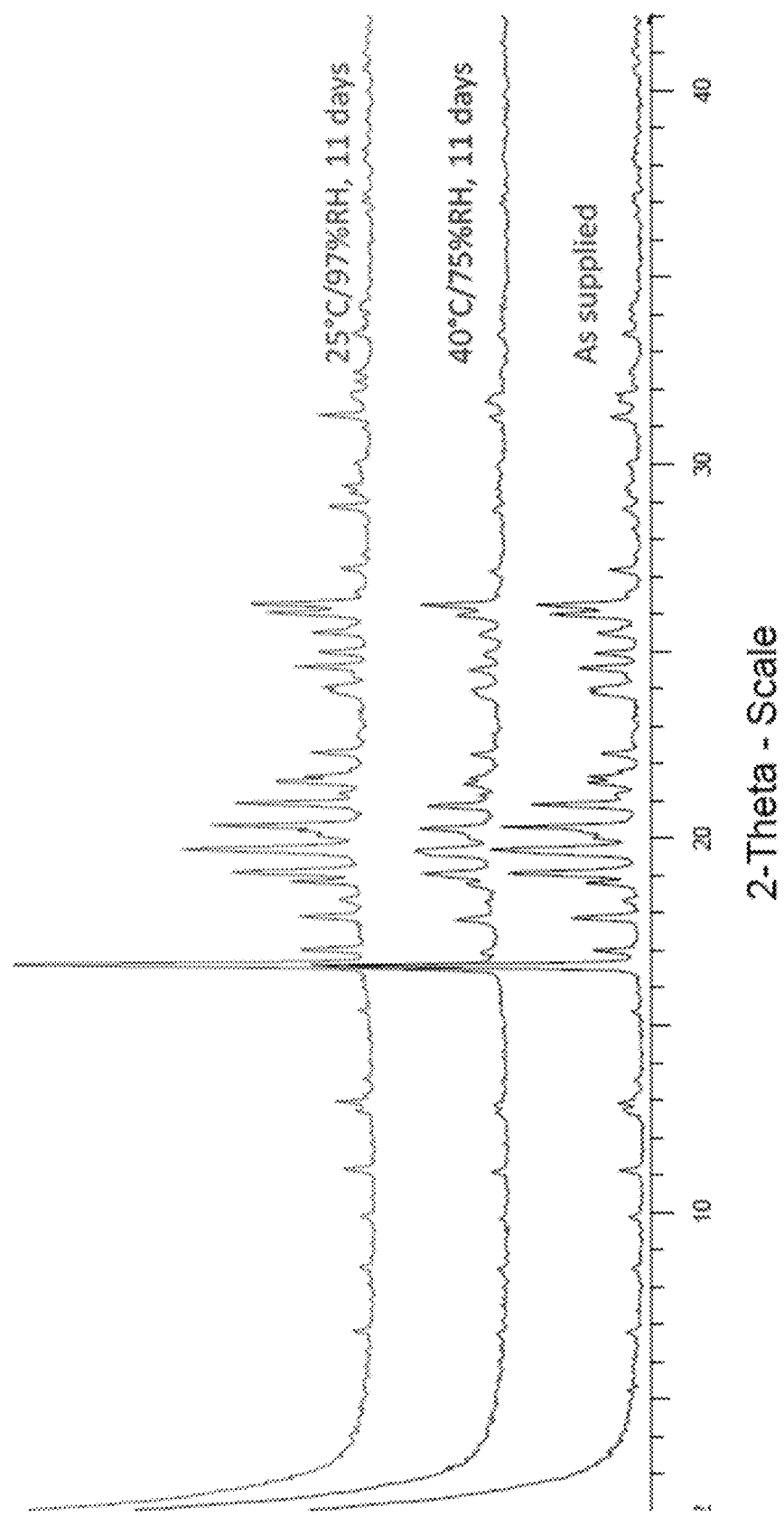

FIG. 12 illustrates XRPD traces of Crystalline Pattern 1 of (I) free acid, as originally obtained, and after storage at 40° C./75% RH and 25° C./97% RH.

Figure 13:
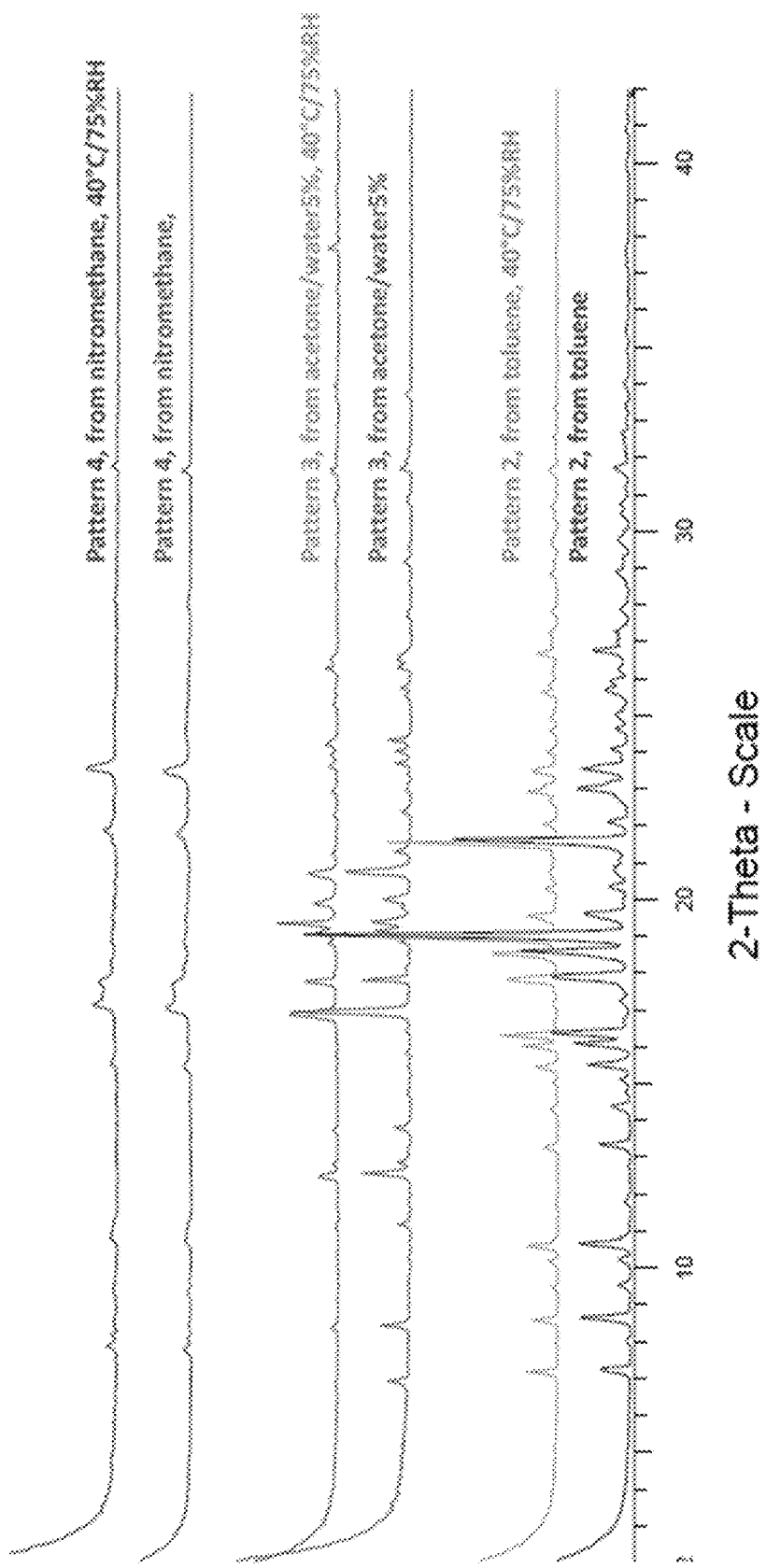

FIG. 13 illustrates XRPD of crystalline (I) free acid materials as originally obtained and after storage at 40° C./75% RH.

Figure 14:
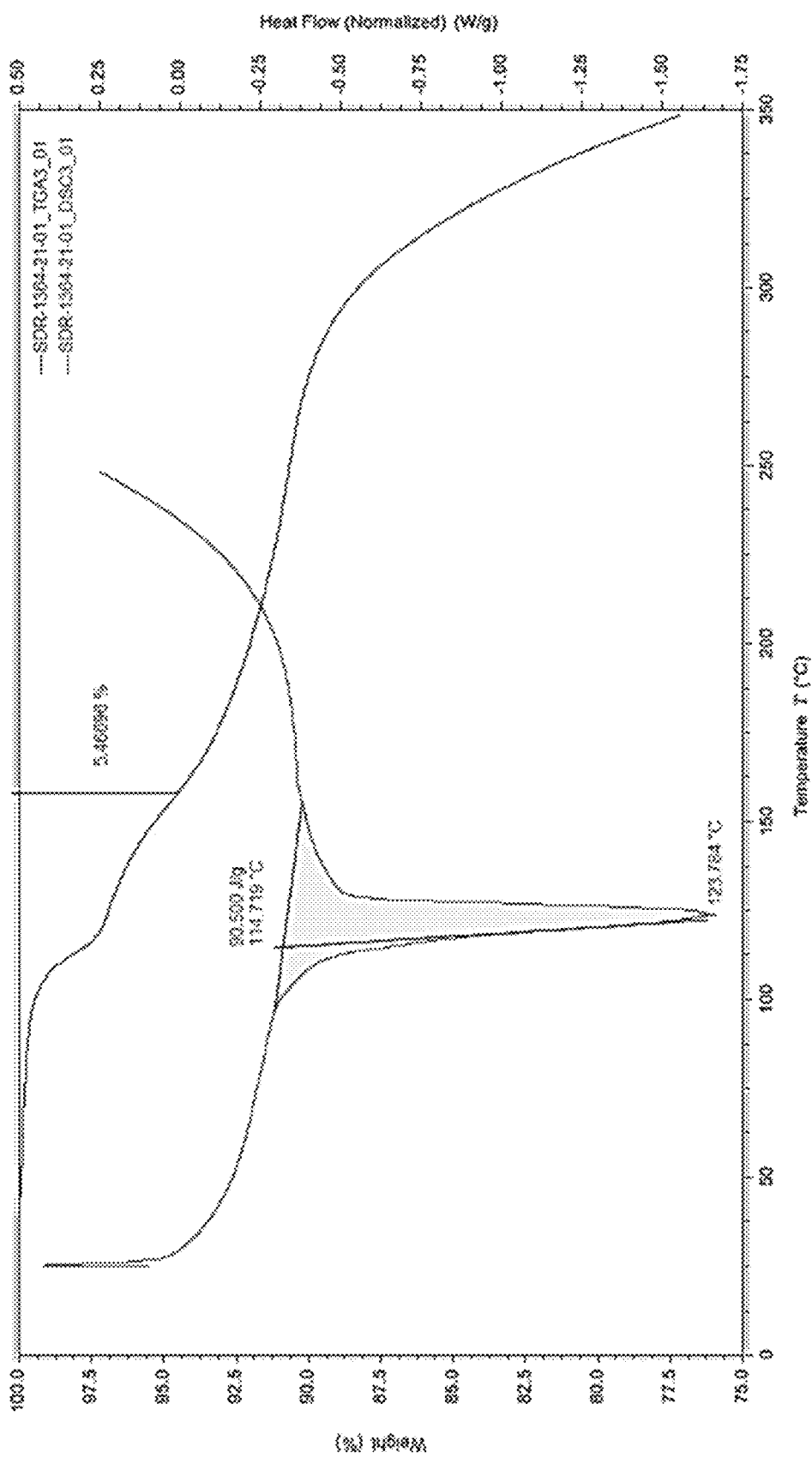

FIG. 14 illustrates TGA and DSC traces of Crystalline Pattern 2 of (I) free acid.

Figure 15:
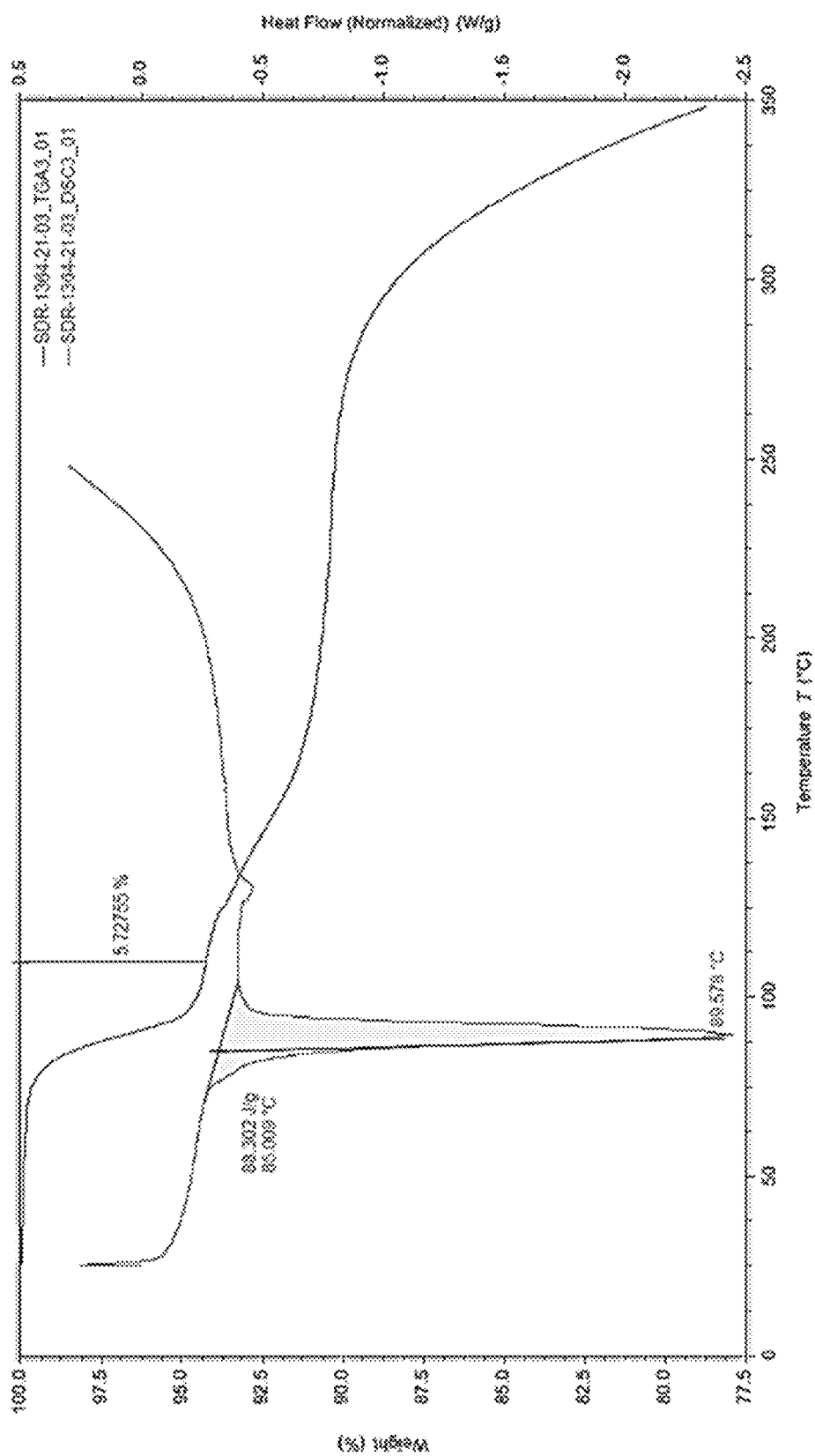

FIG. 15 illustrates TGA and DSC traces of Crystalline Pattern 3 of (I) free acid.

Figure 16:
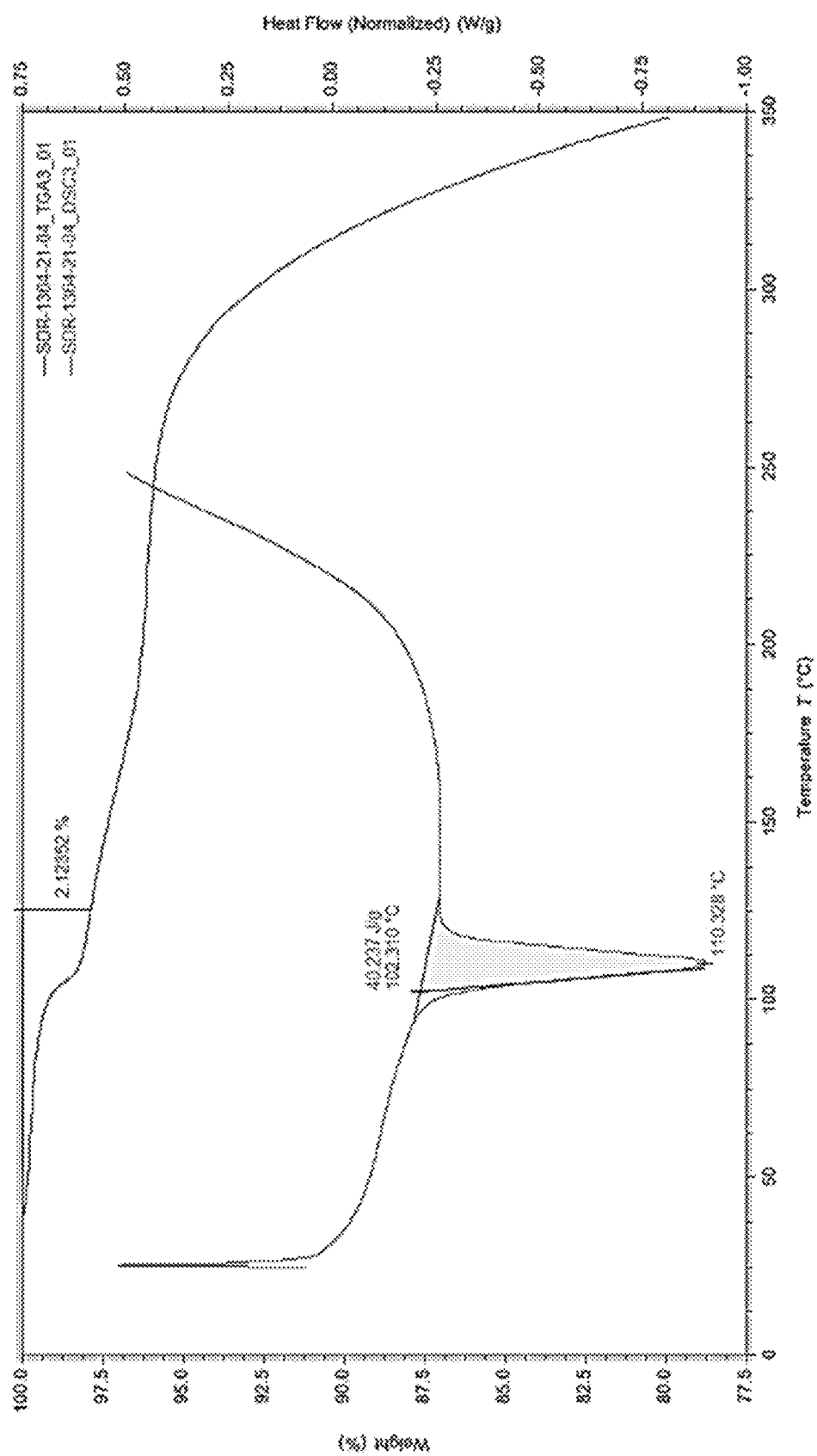

FIG. 16 illustrates TGA and DSC traces of Crystalline Pattern 4 of (I) free acid.

Figure 17:
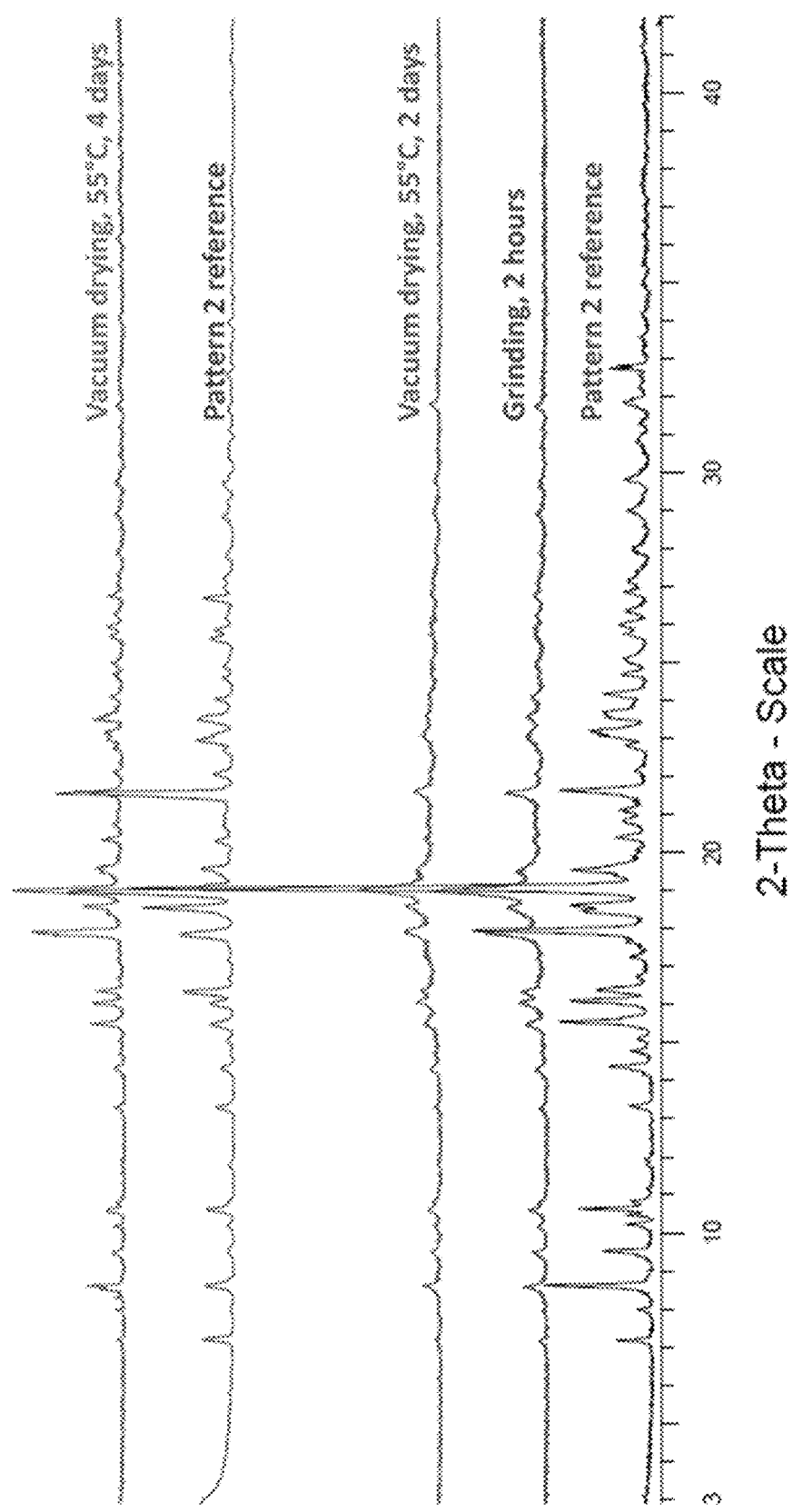

FIG. 17 illustrates XRPD traces of Crystalline Pattern 2 of (I) free acid after stability studies.

Figure 18:
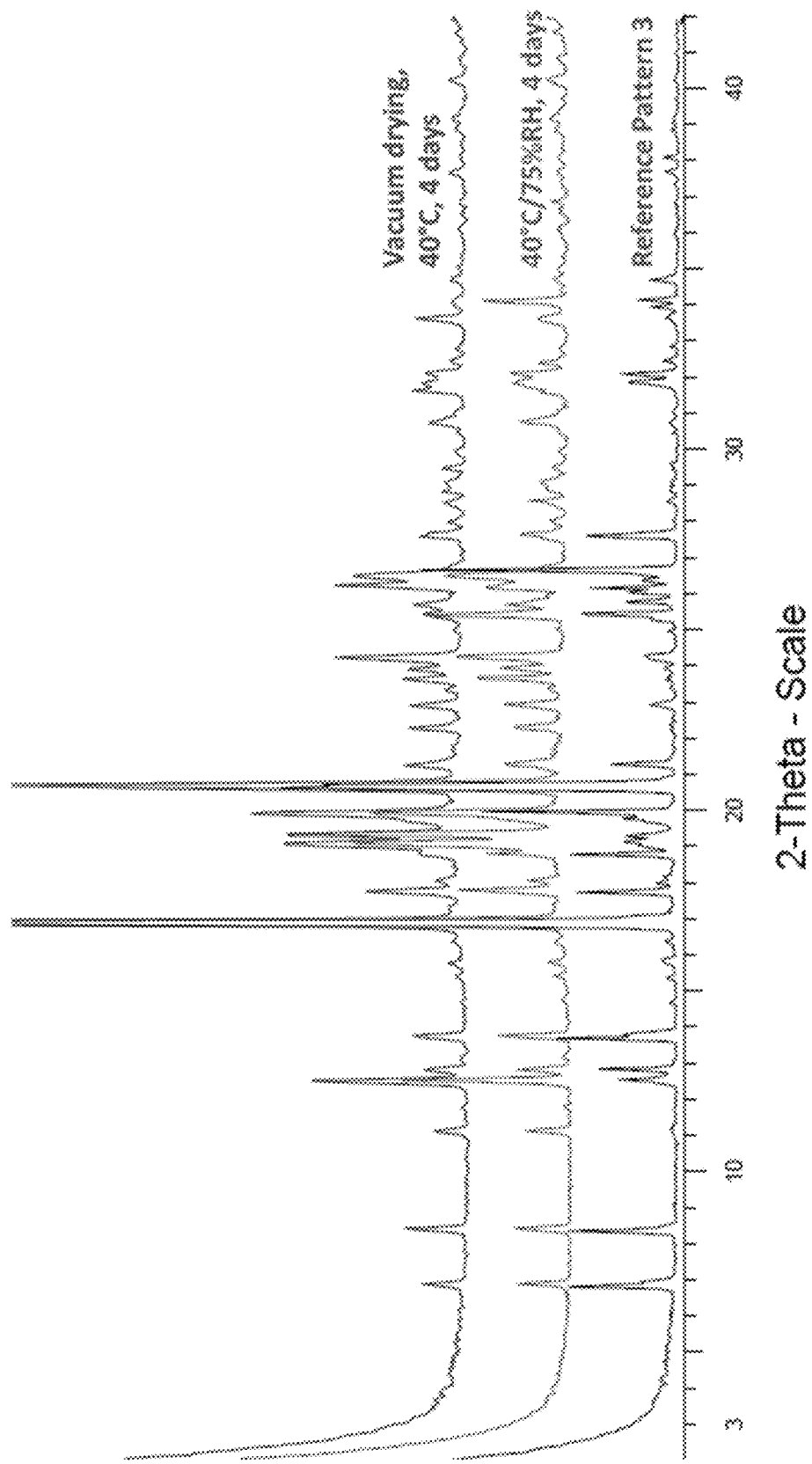

FIG. 18 illustrates XRPD traces of Crystalline Pattern 3 of (I) free acid after stability studies.

Figure 19:
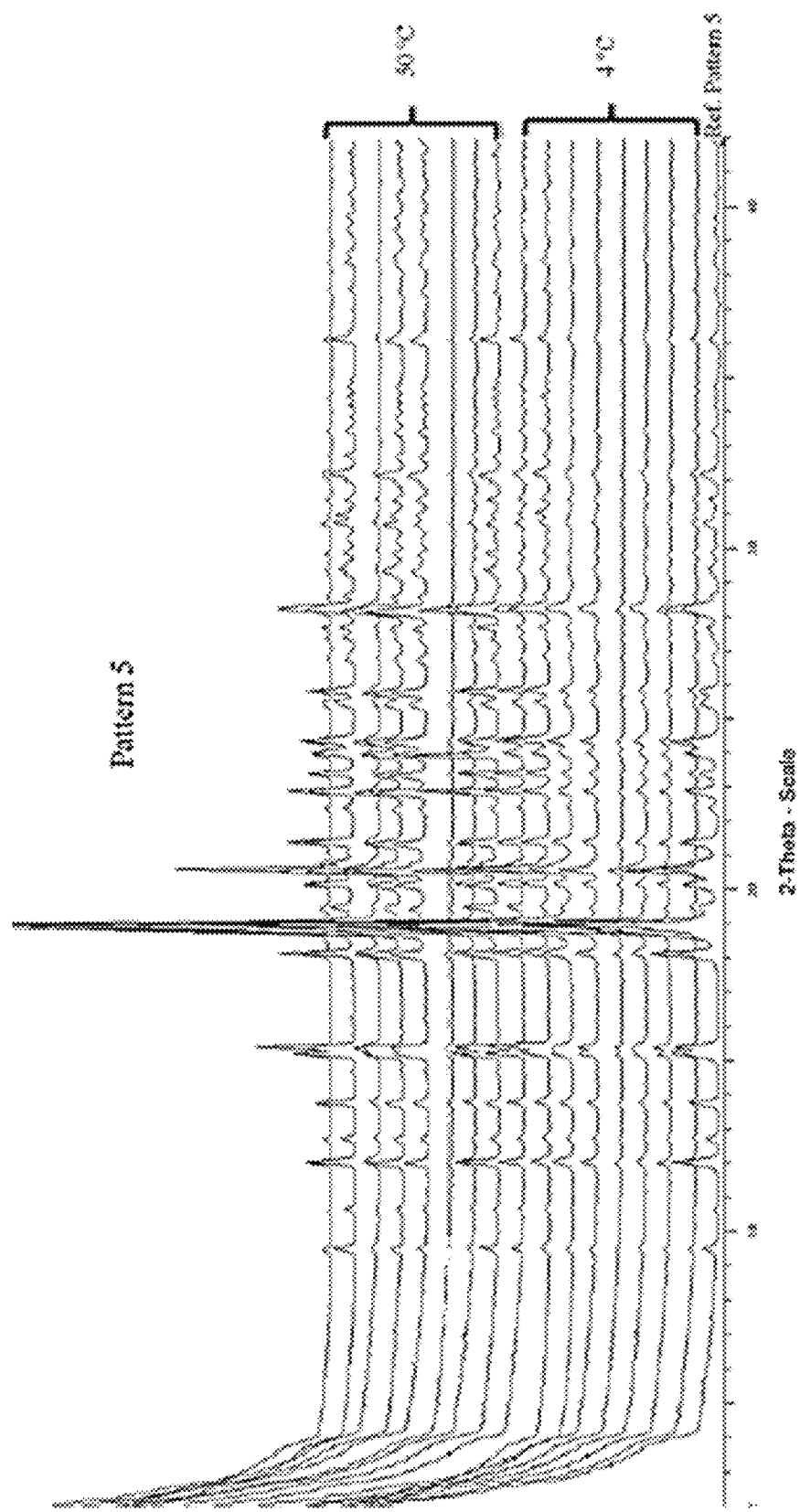

FIG. 19 illustrates XRPD traces of isolated solids from stability assessment, as relating to Crystalline Pattern 5 of (I).

Figure 20:
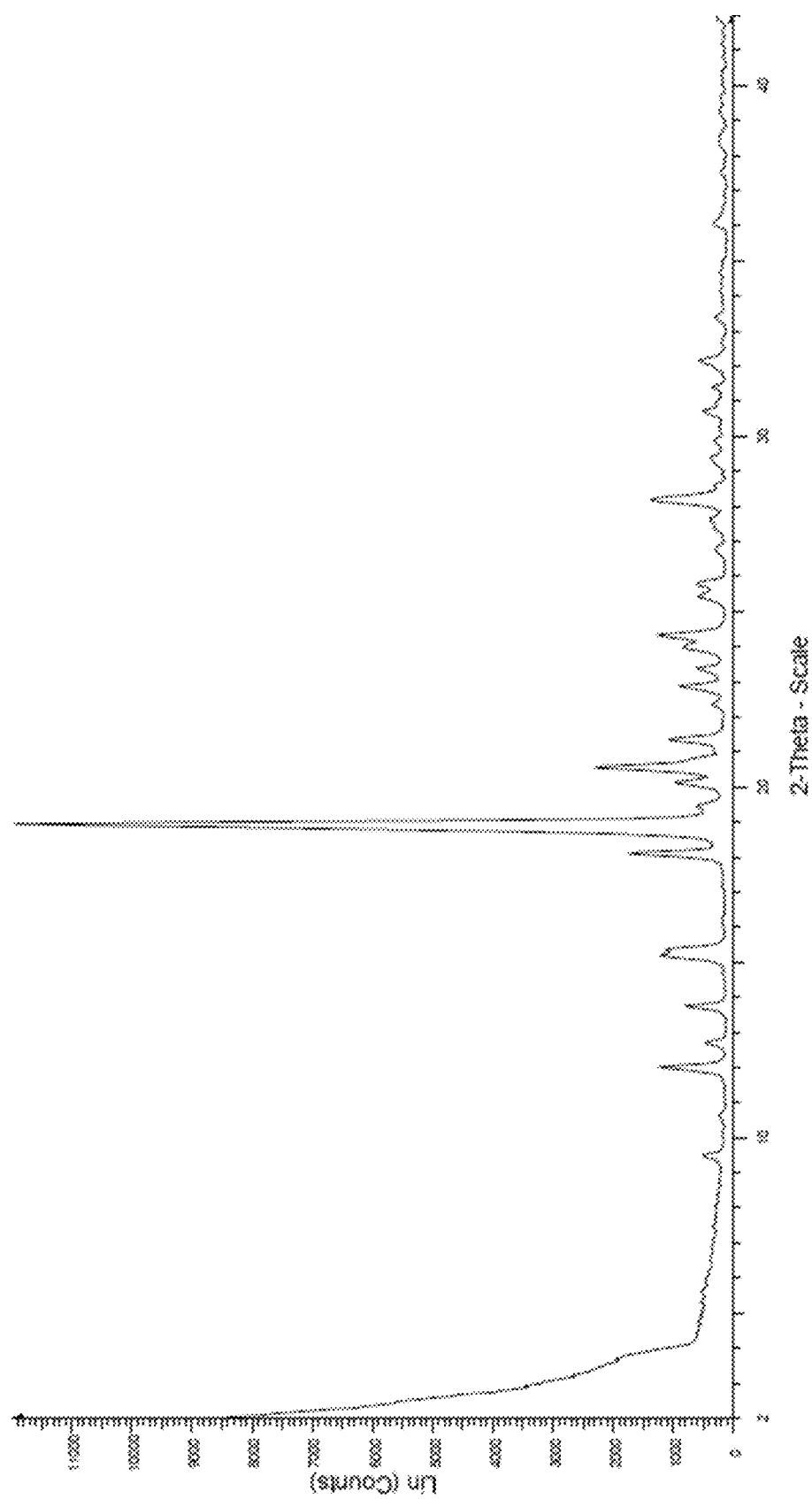

FIG. 20 illustrates a XRPD trace of Crystalline Pattern 5 of (I) free acid.

Figure 21:
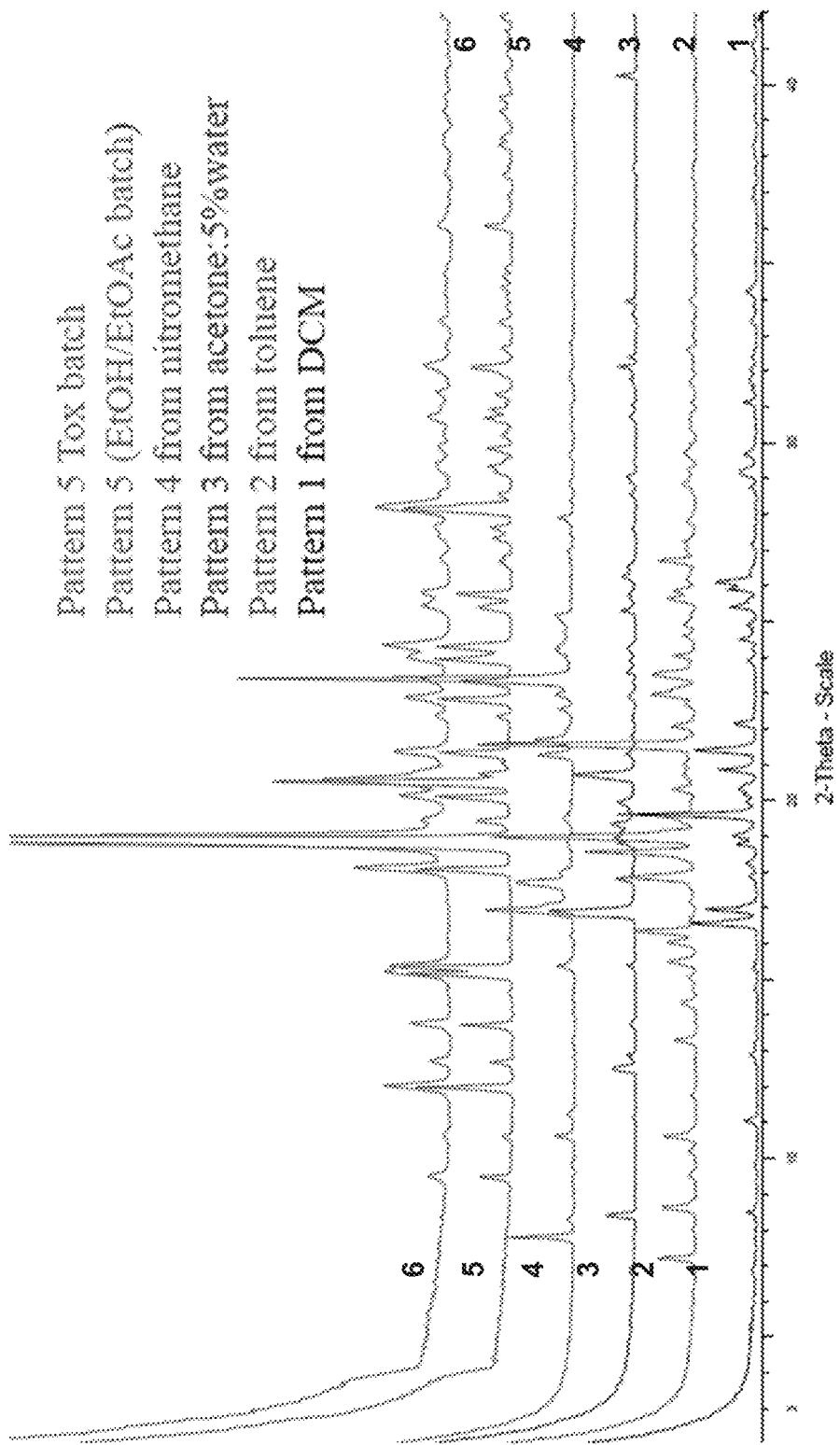

FIG. 21 illustrates XRPD traces for certain solid forms of (I) free acid as described herein.

Figure 22:
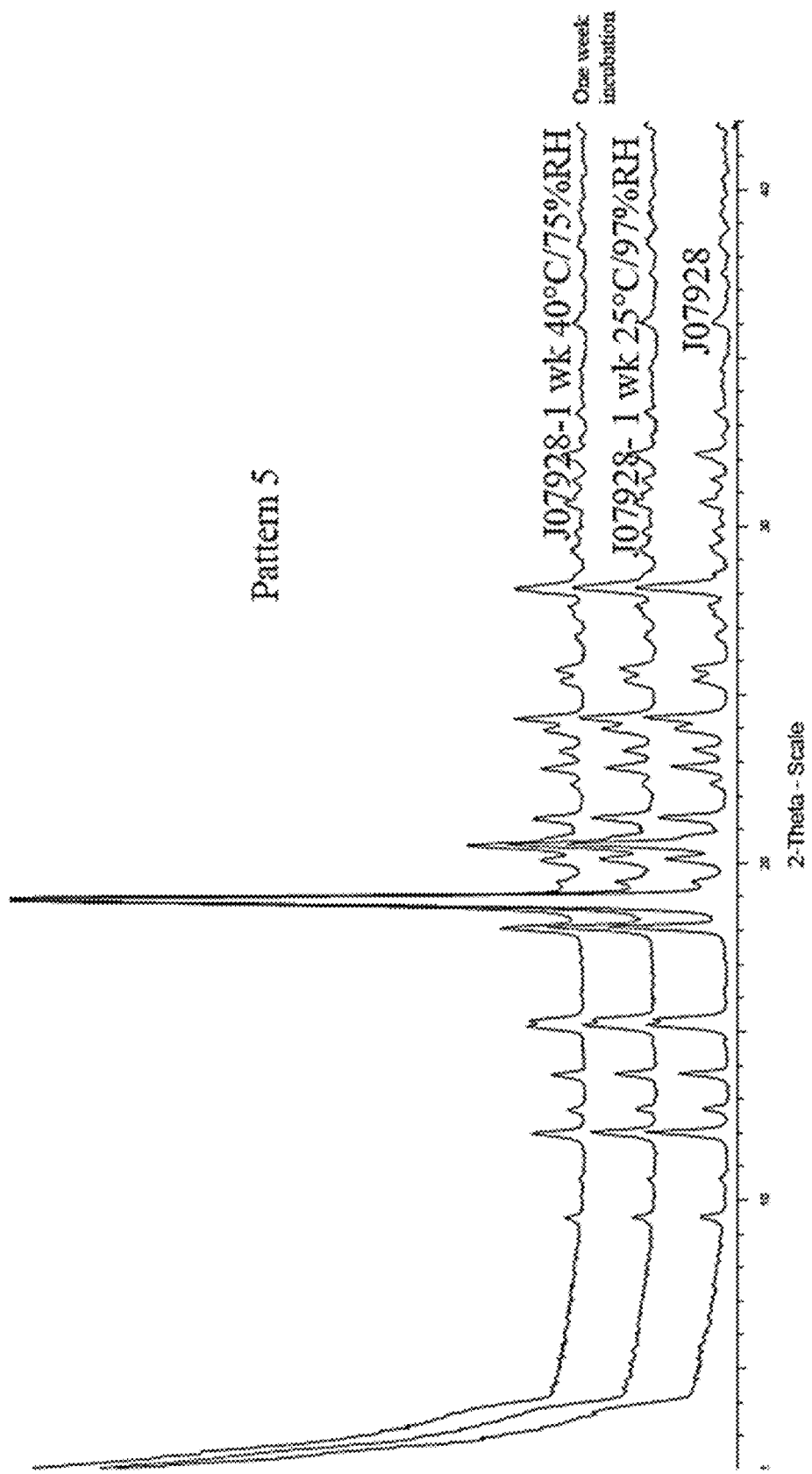

FIG. 22 illustrates XRPD traces of Crystalline Pattern 5 of (I) free acid after one week storage at 40° C./75% RH and 25° C./97% RH.

Figure 23:
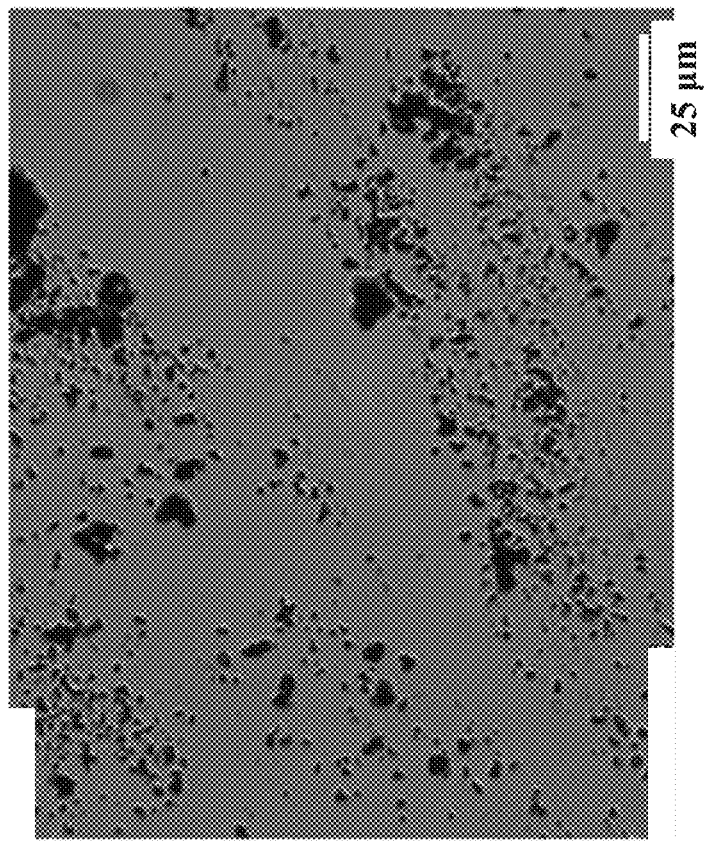
Figure 23:
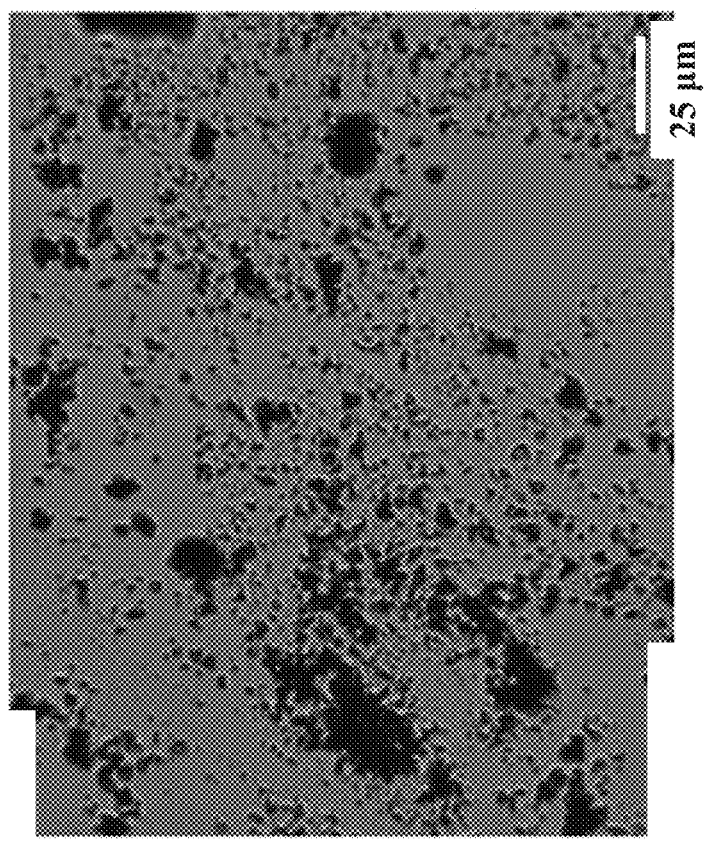

FIG. 23 illustrates PLM illustrations of Crystalline Pattern 5 of (I) free acid.

Figure 24:
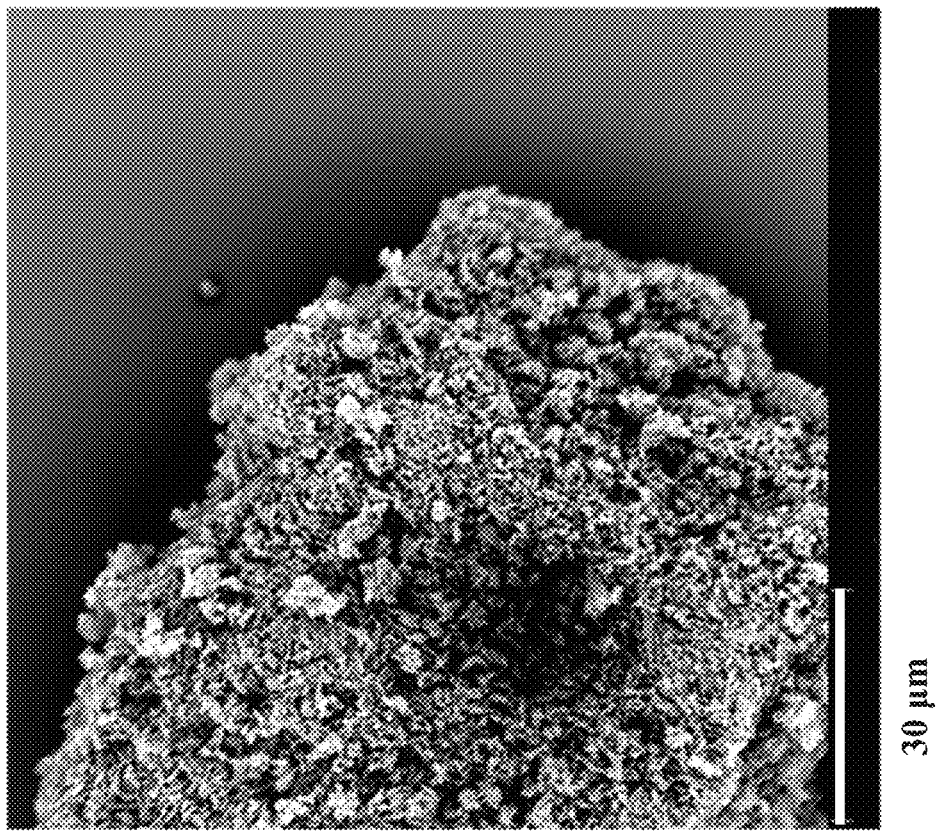
Figure 24:
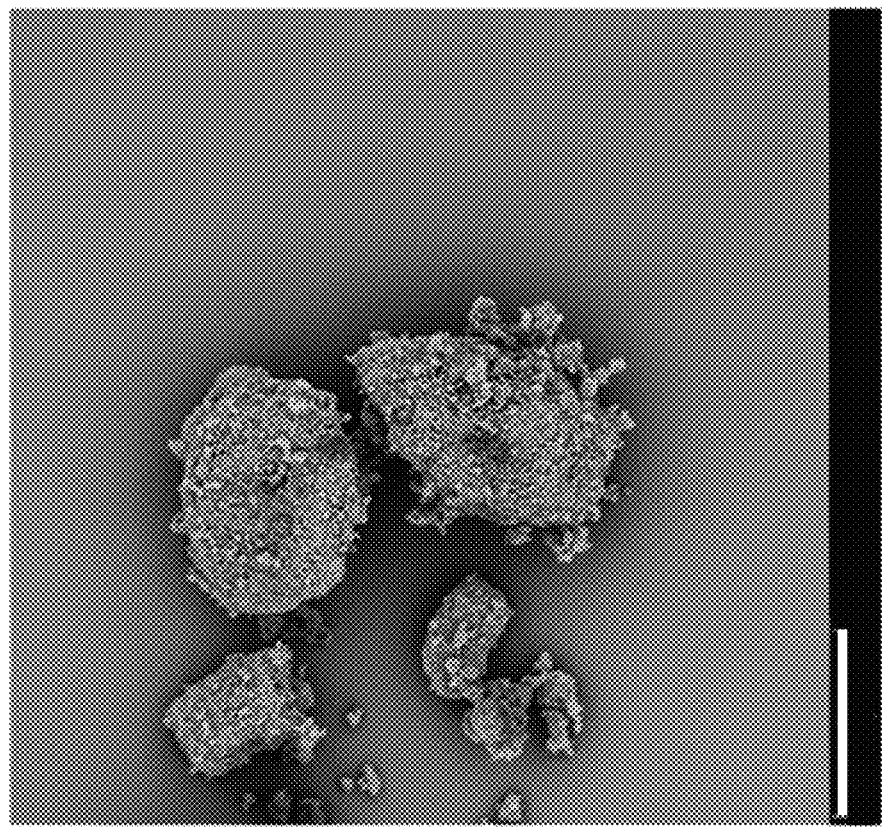

FIG. 24 illustrates SEM illustrations of Crystalline Pattern 5 of (I) free acid.

Figure 25:
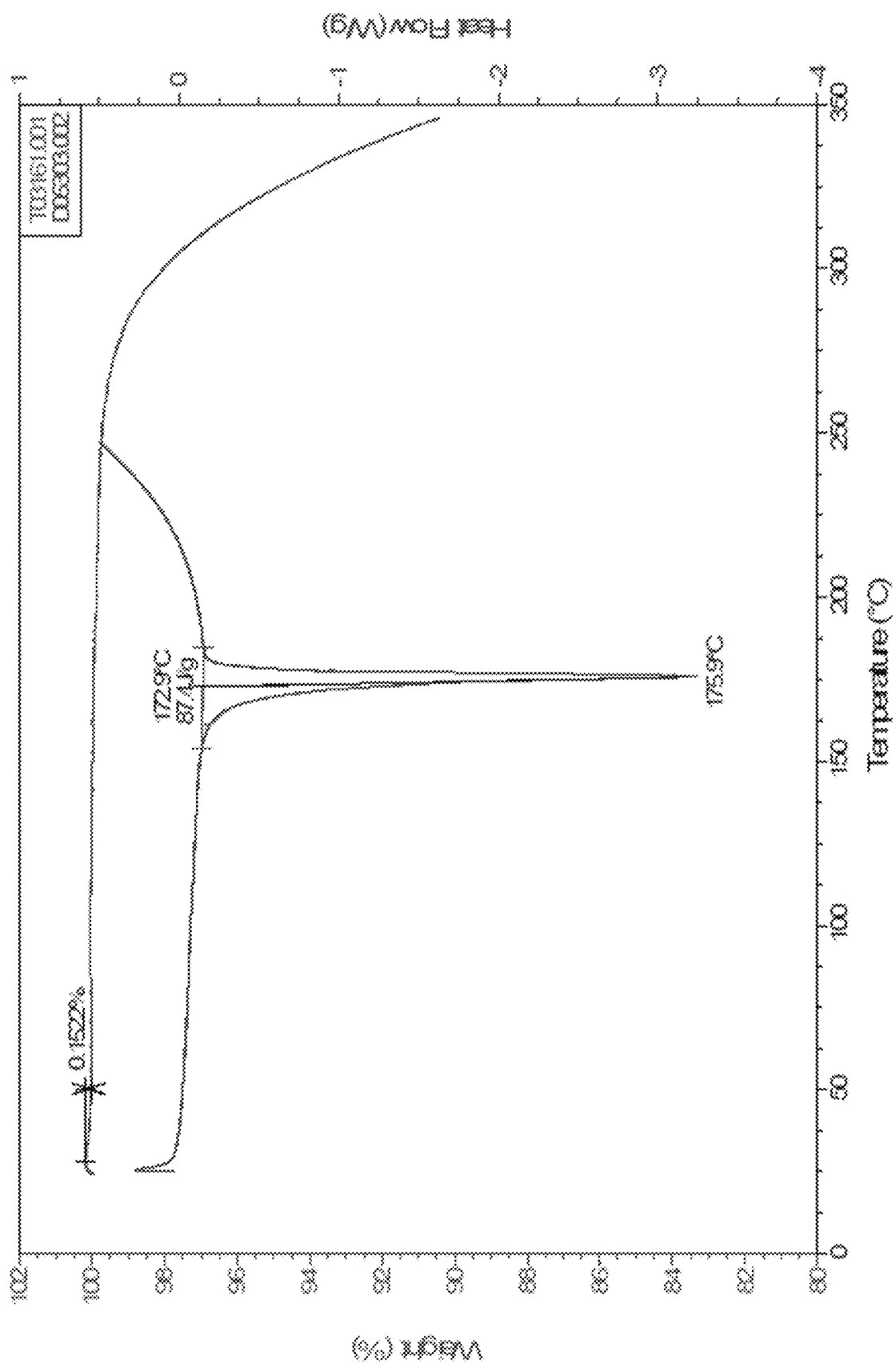

FIG. 25 illustrates thermal analysis of Crystalline Pattern 5 of (I) free acid.

Figure 26:
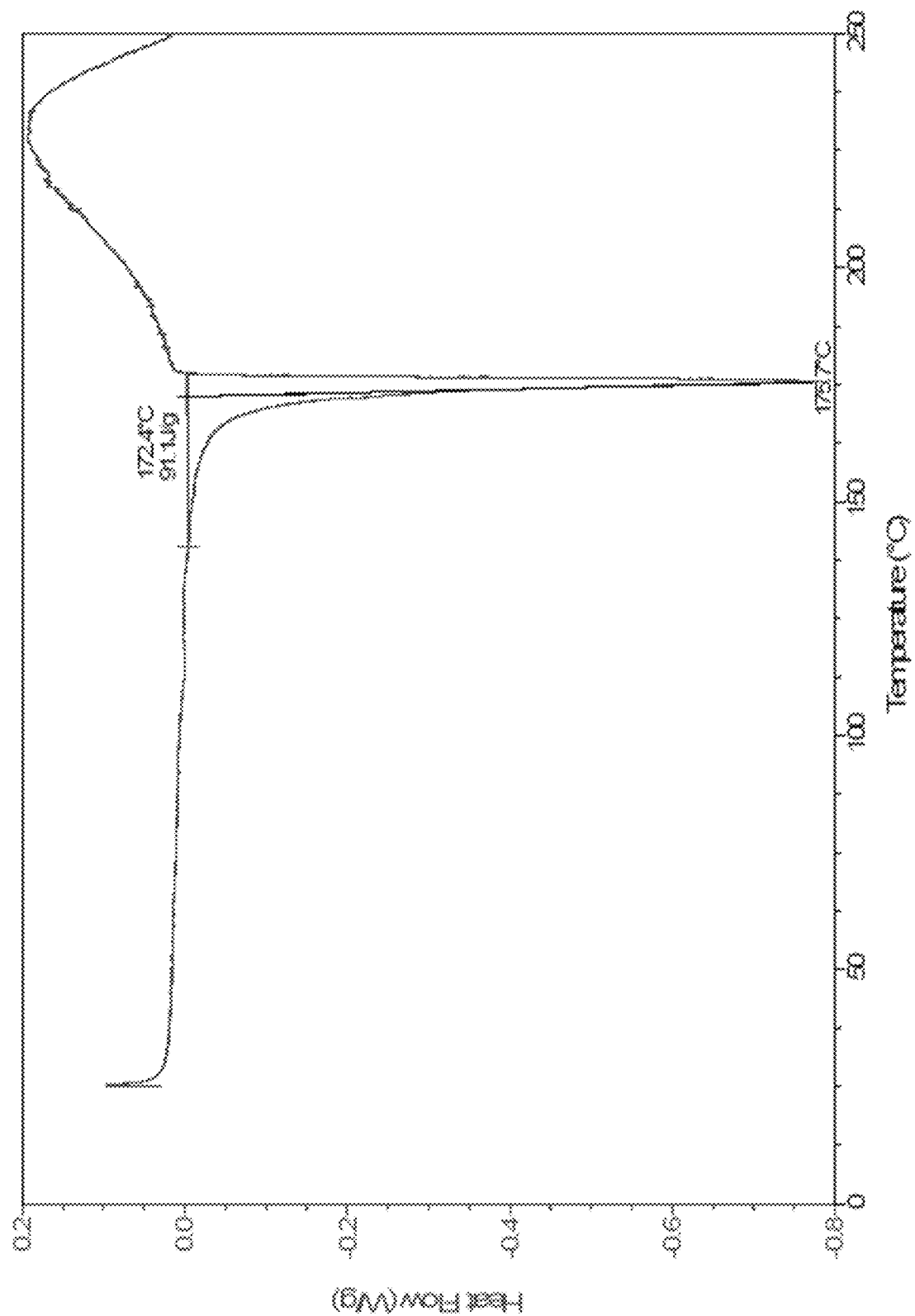

FIG. 26 illustrates a DSC trace of Crystalline Pattern 5 of (I) free acid at 2° C./min.

Figure 27:
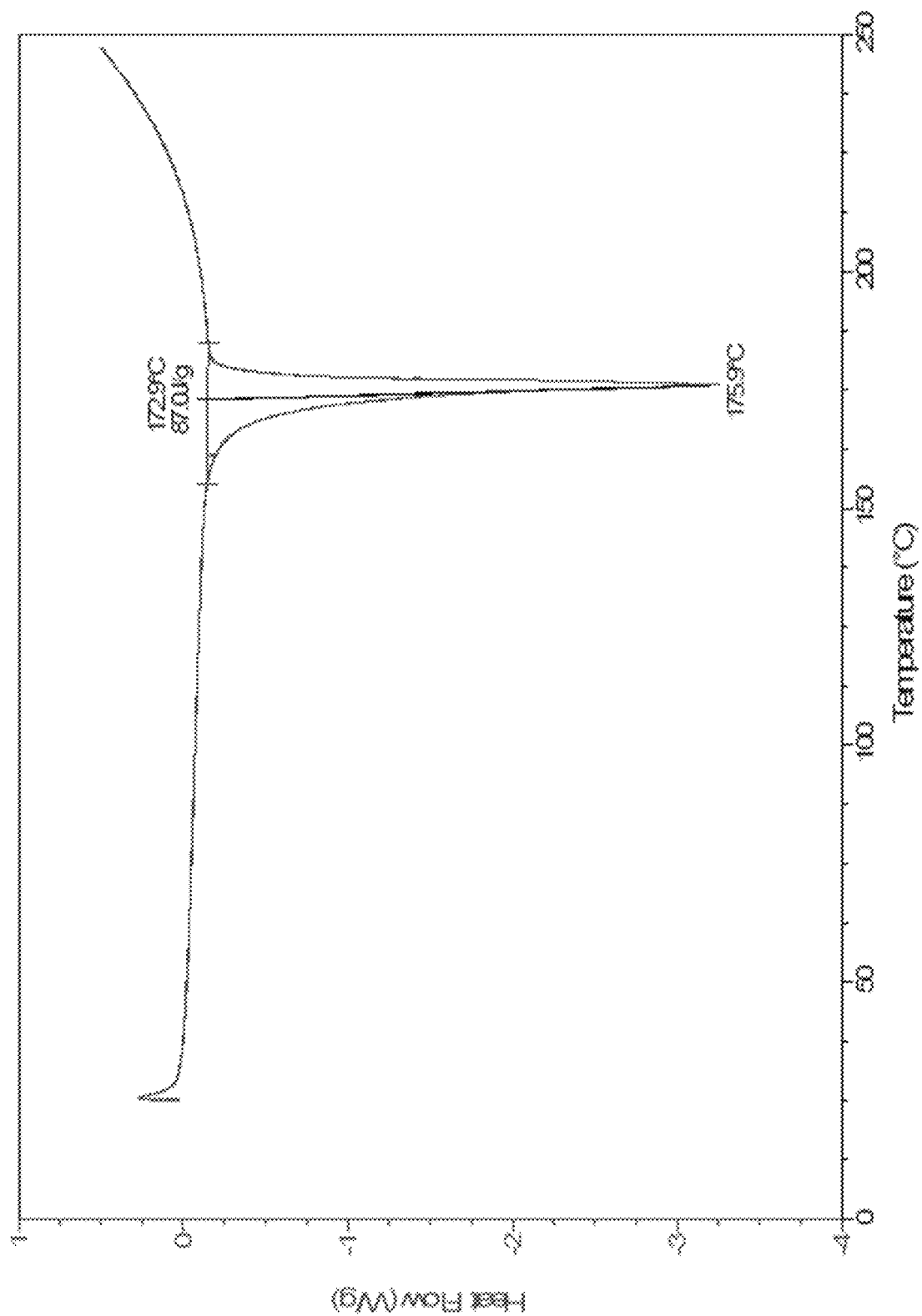

FIG. 27 illustrates a DSC trace of Crystalline Pattern 5 of (I) free acid at 10° C./min.

Figure 28:
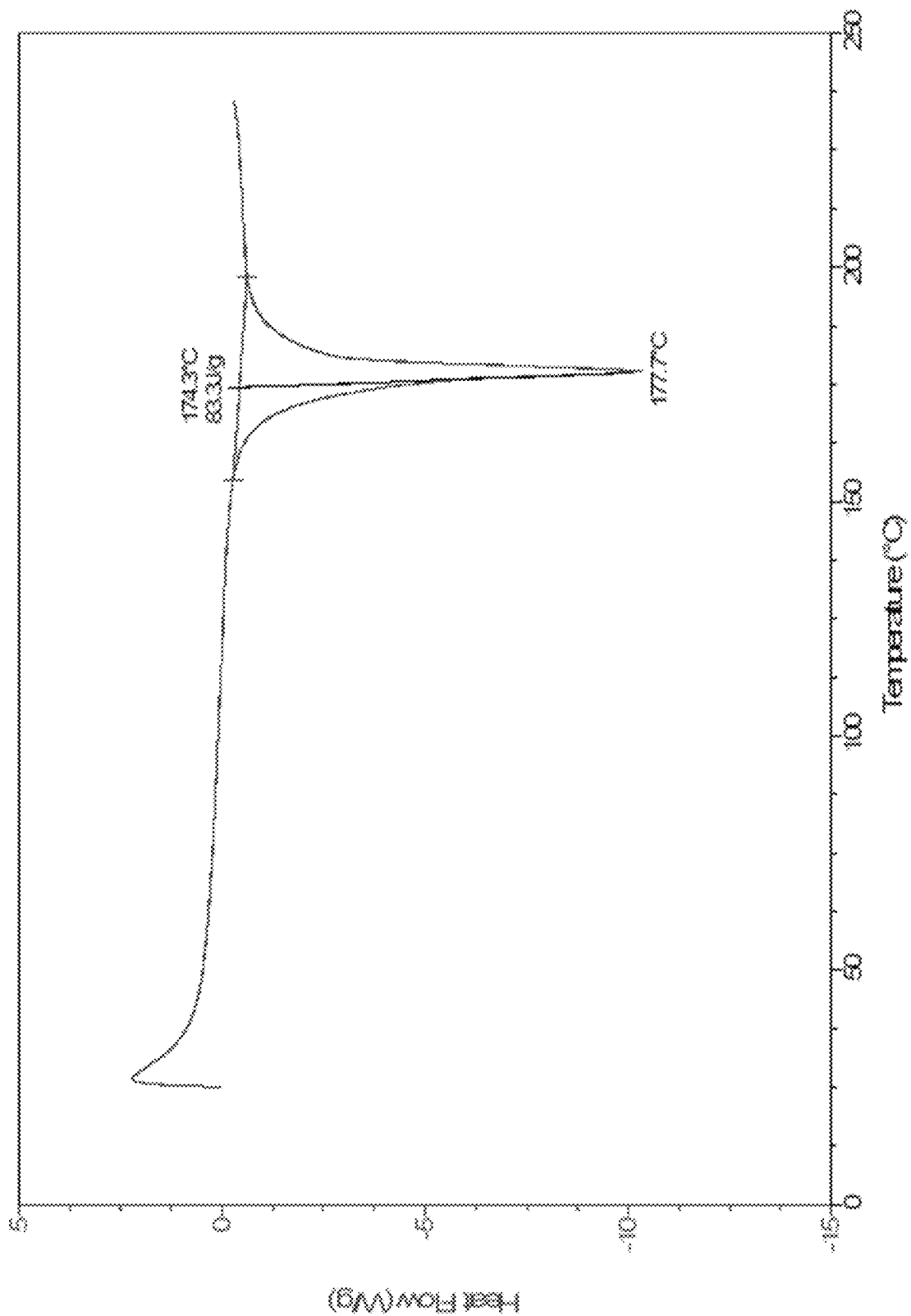

FIG. 28 illustrates a DSC trace of Crystalline Pattern 5 of (I) free acid at 50° C./min.

Figure 29:
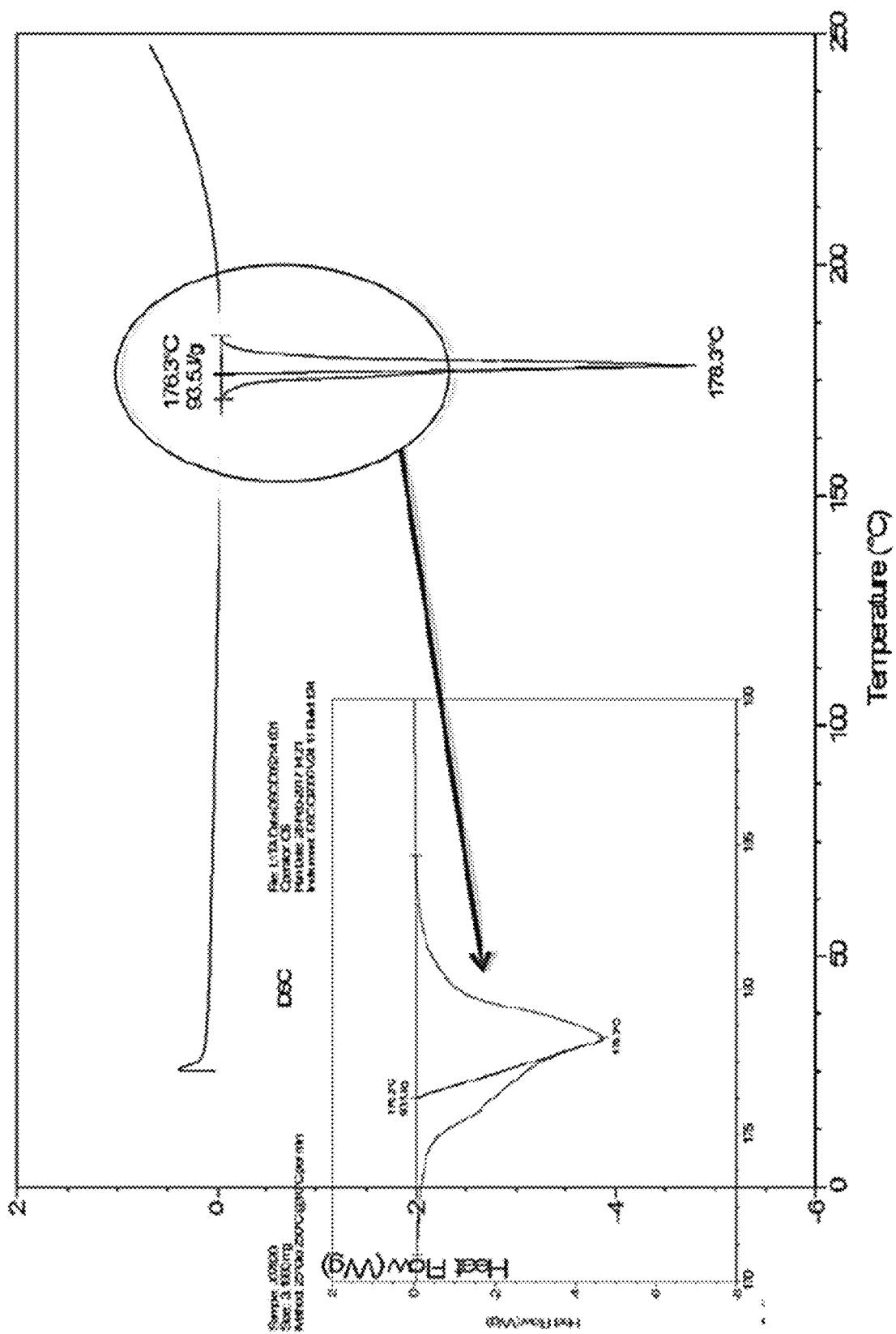

FIG. 29 illustrates a DSC trace of Crystalline Pattern 5 of (I) free acid at 10° C./min.

Figure 30:
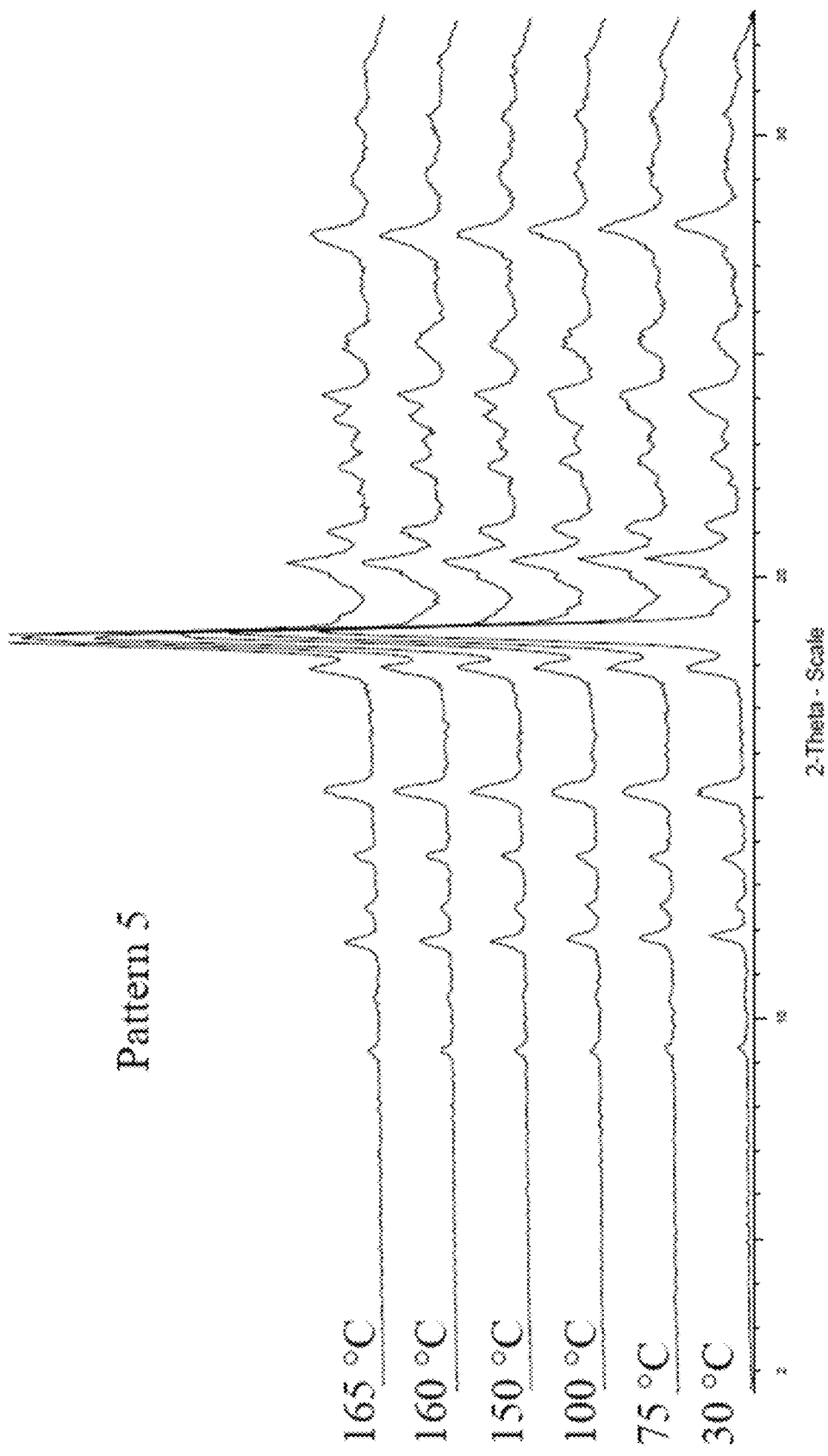

FIG. 30 illustrates certain variable temperature XRPD traces of Crystalline Pattern 5 of (I) free acid.

Figure 31:
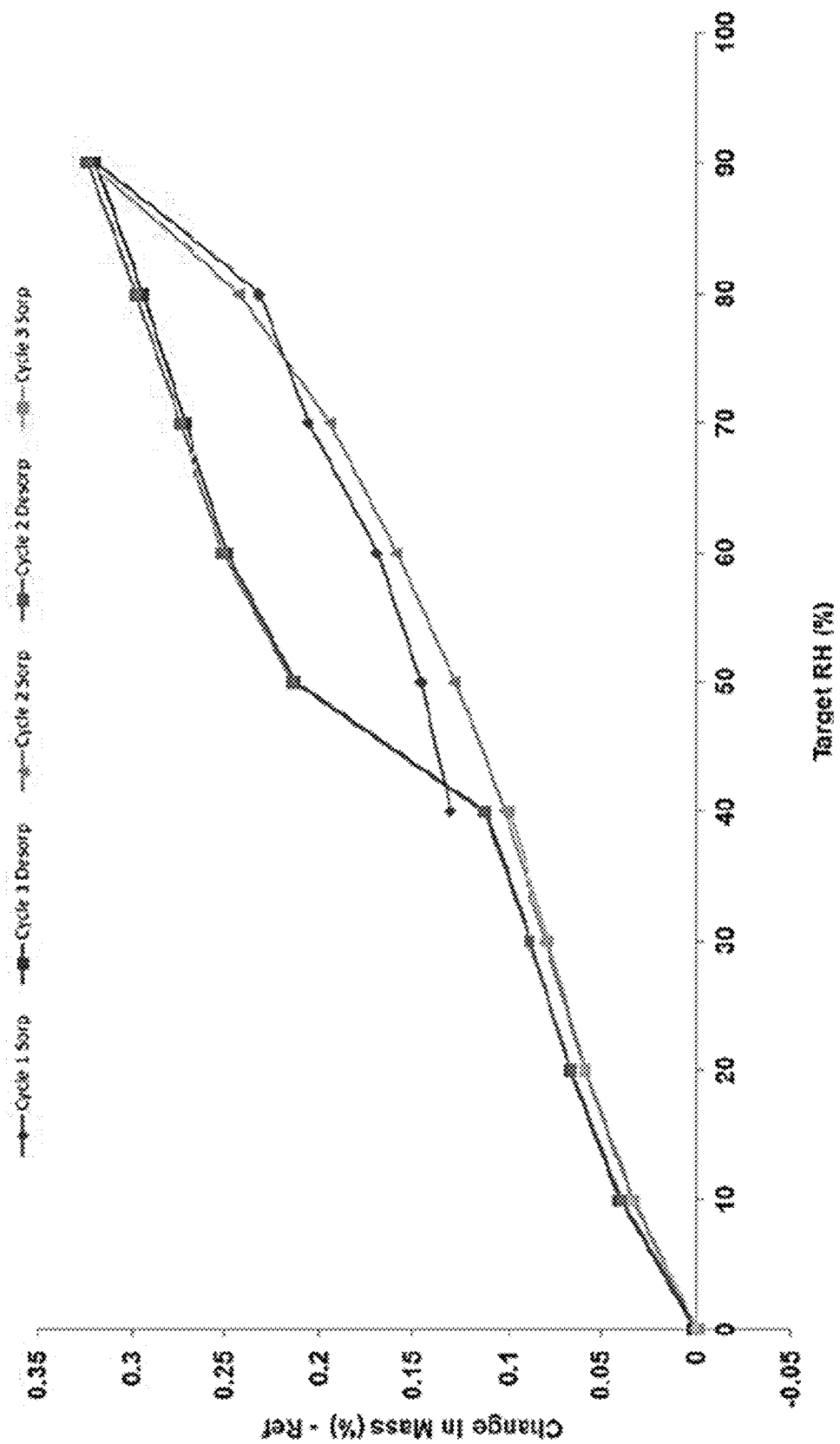

FIG. 31 illustrates a GVS isotherm plot of Crystalline Pattern 5 of (I) free acid.

Figure 32:
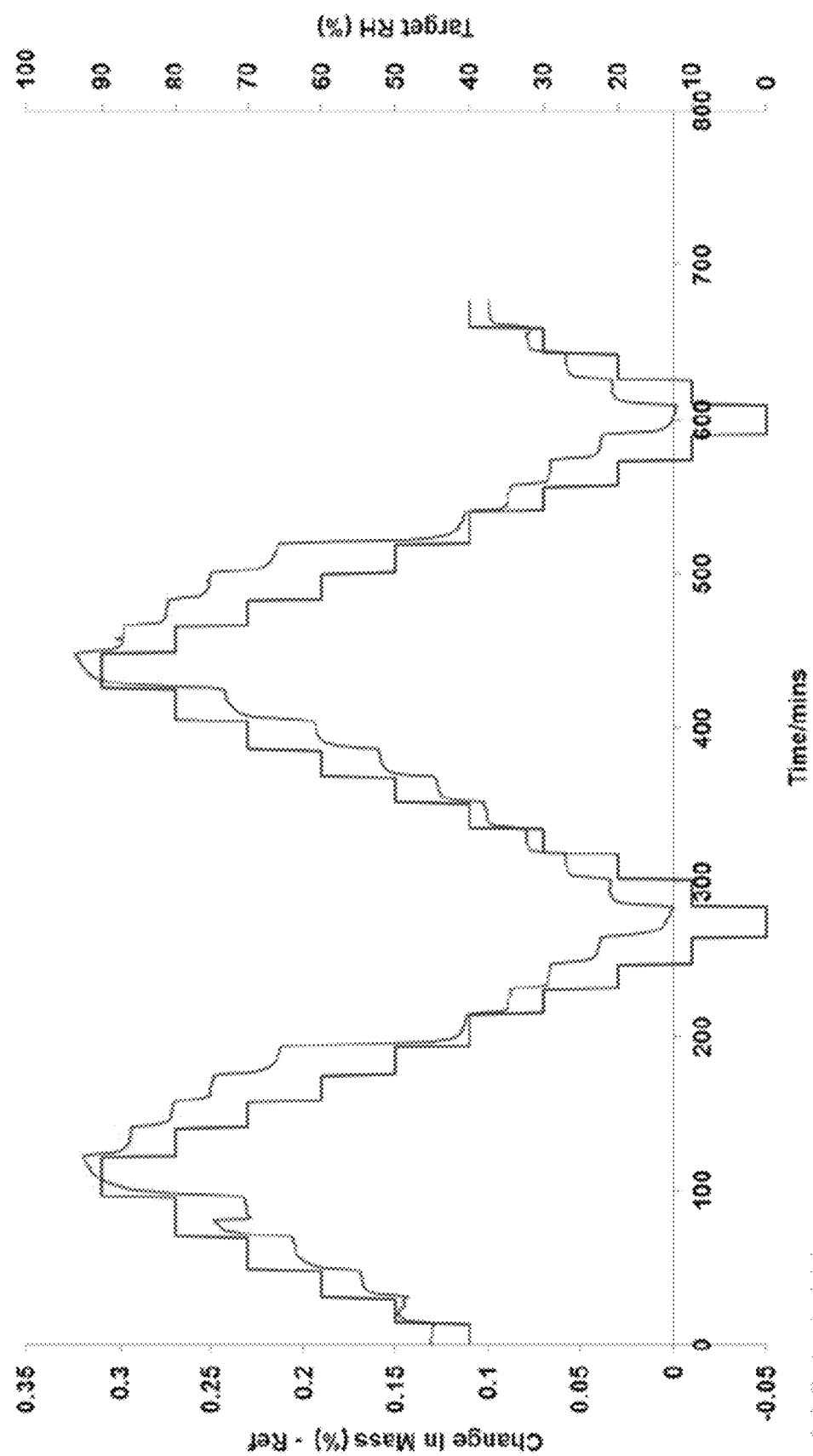

FIG. 32 illustrates a GVS kinetic plot of Crystalline Pattern 5 of (I) free acid.

Figure 33:
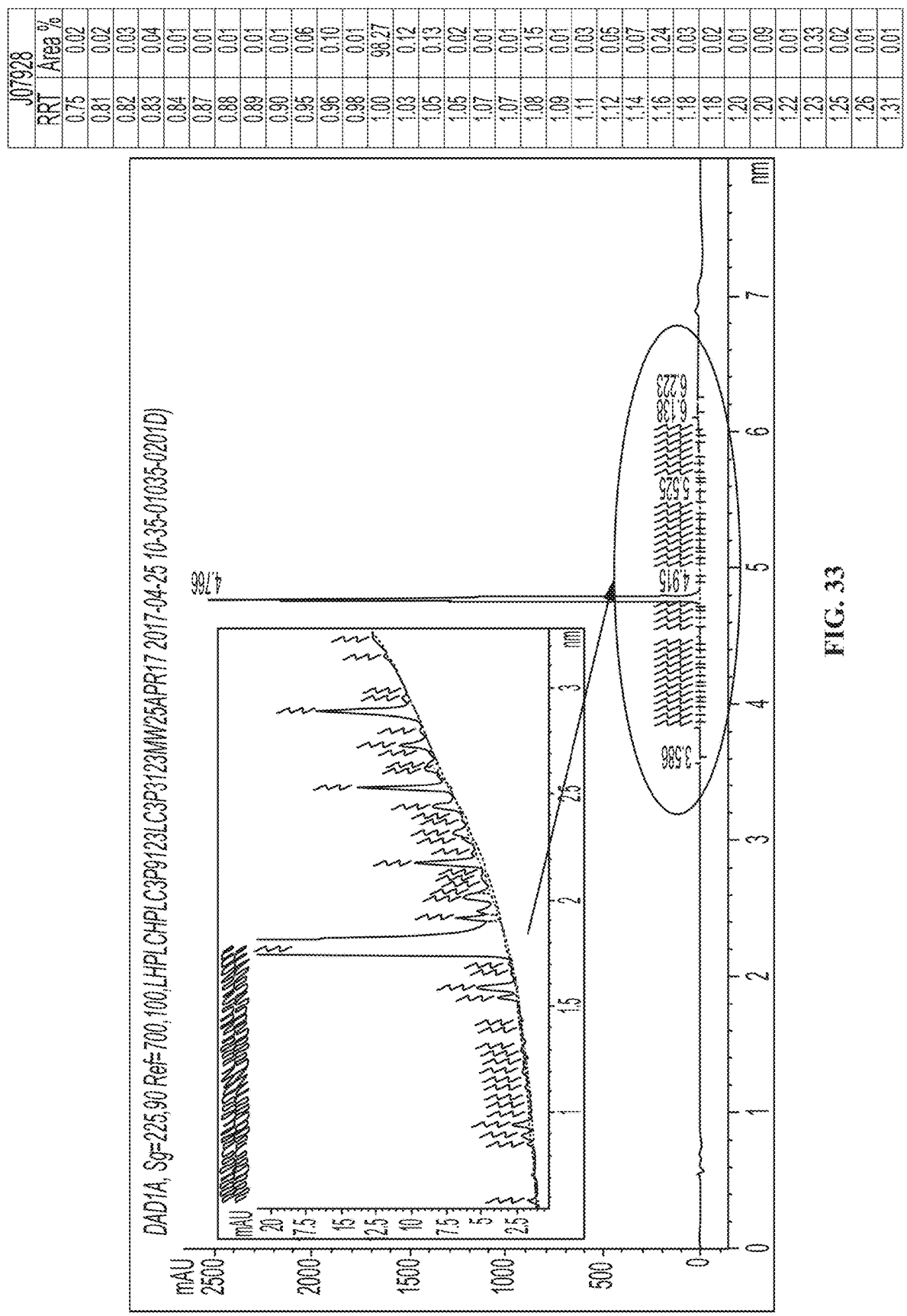

FIG. 33 illustrates a HPLC purity analysis trace for Crystalline Pattern 5 of (I) free acid.

Figure 34:
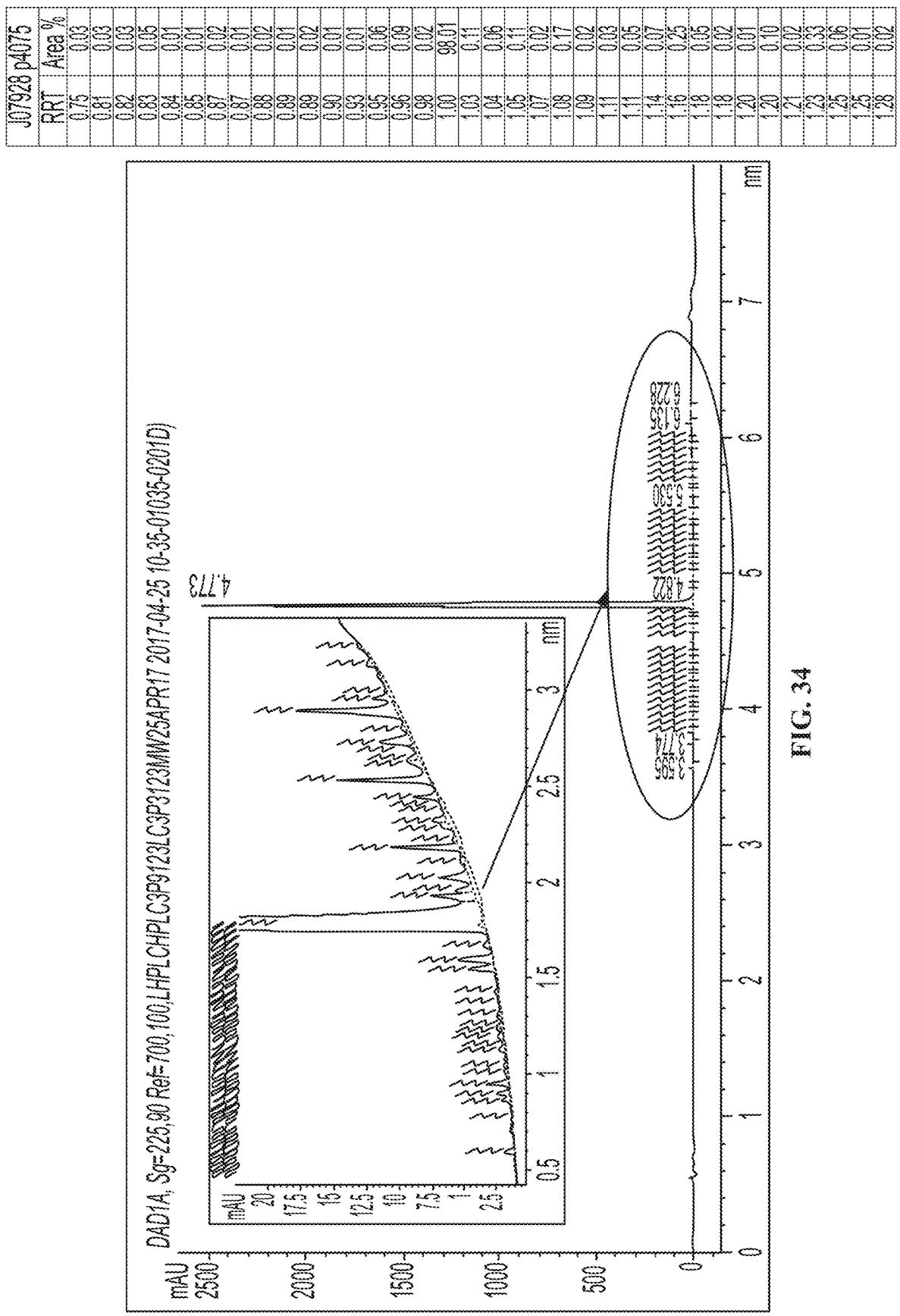

FIG. 34 illustrates a HPLC purity analysis trace for Crystalline Pattern 5 of (I) free acid after one week storage at 40° C./75% RH.

Figure 35:
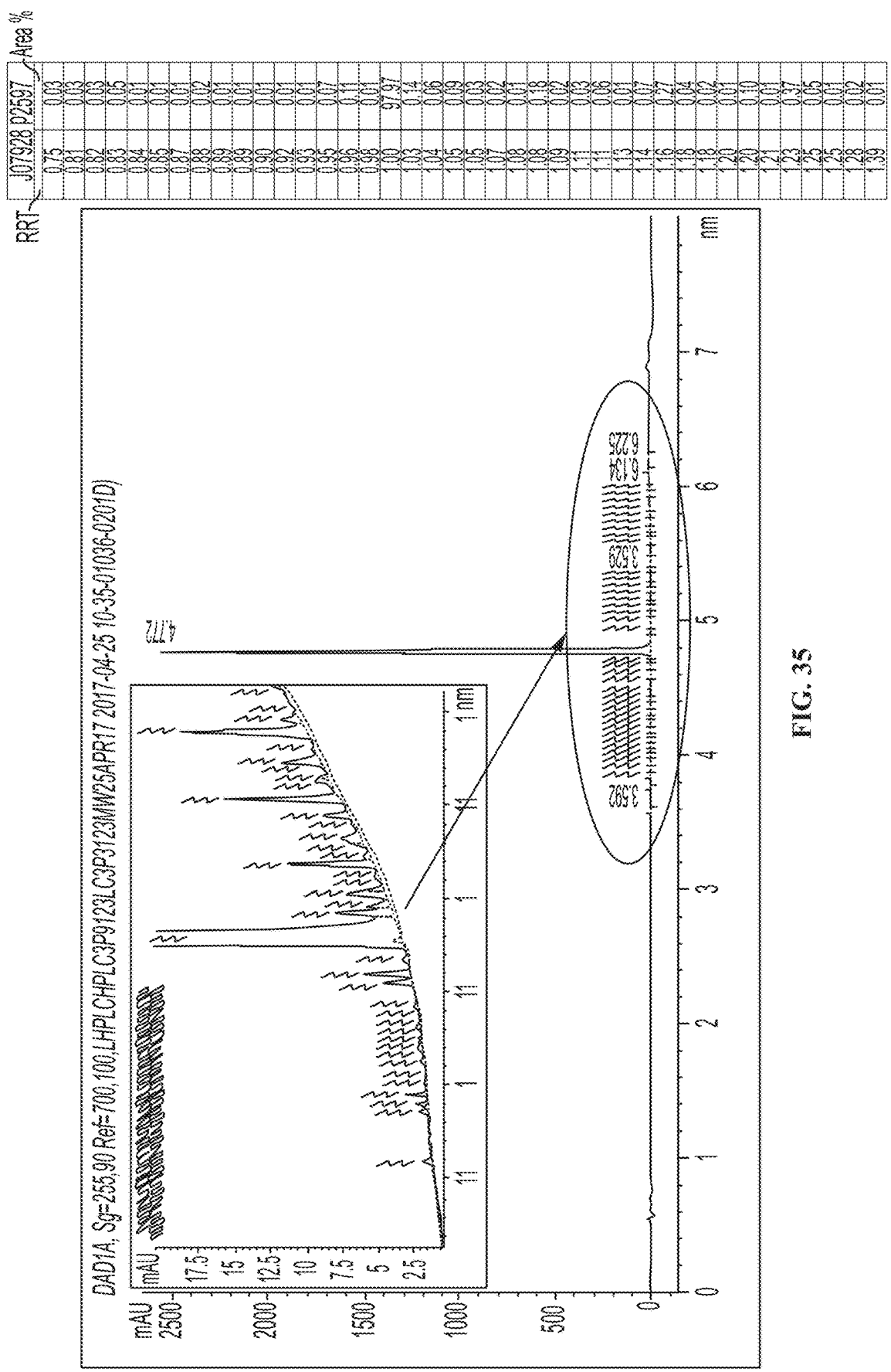

FIG. 35 illustrates a HPLC purity analysis trace for Crystalline Pattern 5 of (I) free acid after one week storage at 25° C./97% RH.

DETAILED DESCRIPTION OF THE INVENTION

The invention relates, in certain aspects, to developable forms of certain substituted compounds that are useful to treat and/or prevent EBV infection and related conditions in a subject. In certain embodiments, such compounds were described in PCT Application Publication No. WO/2016/183534, which is incorporated herein in its entirety by reference.

In certain embodiments, the present invention provides developable forms of 2-(1H-Indol-6-yl)-3-[4-(tetrahydro-pyran-4-yloxymethyl)-phenylethynyl]-benzoic acid (I), or a salt or solvate thereof:

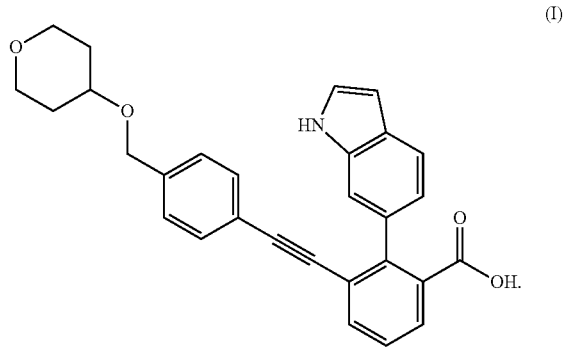 [SMILES: O=C(O)c1cccc(C#Cc2ccc(COC3CCOCC3)cc2)c1-c1ccc2cc[nH]c2c1]

In other embodiments, the present invention provides polymorphs of (I) free acid (which may include any solvates thereof), or a salt thereof.

As described herein, four crystalline solvated forms of (I) free acid were identified during the crystallization screen from dichloromethane (DCM), toluene, acetone or acetone/water, and nitromethane. In each of these structures, efforts made to produce anhydrous (or hydrated) forms by drying the solvated form (and re-hydration with atmosphere water) were unsuccessful, as the solvents seemed to be integral part of the structure.

As described herein, a crystalline, non-solvated, non-hygroscopic form of (I), denoted Crystalline Pattern 5, was identified. No change in crystalline form of Crystalline Pattern 5 was observed by XRPD after one week storage at elevated temperatures and humidity levels (40° C./75% RH and 25° C./97% RH). The chemical purity of the received material was 98.3% A.U.C., which remained unchanged after stability storage at both conditions. A sharp melt was observed on the DSC thermogram at 172.9° C., and by varying the heating rate, there was no sign of a shoulder preceding the main melting event. The stability assessment of Crystalline Pattern 5 at two different temperatures (4 and 50° C.) and 8 solvents, including solvent mixtures, resulted in Pattern 5 being recovered in all cases. In other words, Pattern 5 remained unchanged throughout the course of the study.

Definitions

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

As used herein, unless defined otherwise, all technical and scientific terms generally have the same meaning as commonly understood by one of ordinary skill in the art to which this invention belongs. Generally, the nomenclature used herein and the laboratory procedures in organic chemistry, virology, biochemistry and pharmaceutical sciences are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

For the purposes of the present invention the terms "compound," "analog," and "composition of matter" stand equally well for the prodrug agent described herein, including all enantiomeric forms, diastereoisomeric forms, salts, and the like, and the terms "compound," "analog," and "composition of matter" are used interchangeably throughout the present specification.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "EBNA1 inhibitor" refers a compound that inhibits EBNA1.

As used herein, the term "EBV" refers to Epstein-Barr virus.

As used herein, an "effective amount," "therapeutically effective amount" or "pharmaceutically effective amount" of a compound is that amount of compound that is sufficient to provide a beneficial effect to the subject to which the compound is administered.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention.

Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

The term "prevent," "preventing" or "prevention," as used herein, means avoiding or delaying the onset of symptoms associated with a disease or condition in a subject that has not developed such symptoms at the time the administering of an agent or compound commences. Disease, condition and disorder are used interchangeably herein.

As used herein, a "patient" or "subject" may be a human or non-human mammal or a bird. Non-human mammals include, for example, livestock and pets, such as ovine, bovine, porcine, canine, feline and murine mammals. In certain embodiments, the subject is human.

The term "treat," "treating" or "treatment," as used herein, means reducing the frequency or severity with which symptoms of a disease or condition are experienced by a subject by virtue of administering an agent or compound to the subject.

Abbreviations individual numbers within that range, for example, 1, 2, 2.7, 3, 4, 5, 5.3, and 6. This applies regardless of the breadth of the range.

Compounds

The compounds described herein can form salts with acids and/or bases, and such salts are included in the present invention. In certain embodiments, the salts are pharmaceutically acceptable salts. The term "salts" embraces addition salts of free acids and/or bases that are useful within the methods of the invention. The term "pharmaceutically acceptable salt" refers to salts that possess toxicity profiles within a range that affords utility in pharmaceutical applications. Pharmaceutically unacceptable salts can nonetheless possess properties such as high crystallinity, which have utility in the practice of the present invention, such as for example utility in process of synthesis, purification or formulation of compounds useful within the methods of the invention.

Suitable pharmaceutically acceptable acid addition salts can be prepared from an inorganic acid or from an organic acid. Examples of inorganic acids include sulfate, hydrogen sulfate, hemisulfate, hydrochloric, hydrobromic, hydriodic, nitric, carbonic, sulfuric, and phosphoric acids (including hydrogen phosphate and dihydrogen phosphate). Appropriate organic acids can be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric,

| Acronym | Meaning | Acronym | Meaning |
|---|---|---|---|
| Ca. | Approximately | $^1$H-NMR | Proton Nuclear Magnetic Resonance |
| Eq. | Equivalent | CCD | Charge Coupled Detector |
| ID | Identification | DSC | Differential Scanning Calorimetry |
| N/A | Not applicable | DVS | Dynamic Vapour Sorption |
| PTFE | Polytetrafluoroethylene | GVS | Gravimetric Vapour Sorption |
| RH | Relative humidity | HPLC | High Performance Liquid Chromatography |
| RT, rt, or r.t. | Room temperature | IC | Ion Chromatography |
| Vol. | Volumes | KF | Karl-Fischer |
| MeCN | Acetonitrile | MDSC | Modulated Differential Scanning Calorimetry |
| DEA | Diethylamine | PLM | Polarised Light Microscopy |
| DEAE | 2-Diethylaminoethanol | SEM | Scanning Electron Microscopy |
| DMSO | Dimethylsulfoxide | TGA | Thermal Gravimetric Analysis |
| EtOH | Ethanol | UV | Ultraviolet |
| $H_2O$ | Water | XRPD | X-ray Powder Diffraction |
| IPA | Propan-2-ol | | |
| MEK | Methyl ethyl ketone | | |
| MeOH | Methanol | | |
| AUC | Area under curve | | |
| MeOH | Methanol | | |
| THF | Tetrahydrofuran | | |

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate).

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, ammonium, N,N'-dibenzylethylene-diamine, chloroprocaine, choline, diethanolamine, ethylenediamine, meglumine (N-methyl-glucamine) and procaine.

All of these salts can be prepared from the corresponding compound by reacting, for example, the appropriate acid or base with the compound. Salts can be comprised of a fraction of less than one, one, or more than one molar equivalent of acid or base with respect to any compound of the invention.

In certain embodiments, the at least one compound of the invention is a component of a pharmaceutical composition further including at least one pharmaceutically acceptable carrier.

The compounds contemplated in the invention may possess one or more stereocenters, and each stereocenter may exist independently in either the (R) or (S) configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereoisomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Vol. 1-17 (John Wiley and Sons, 1991); Rodd's Chemistry of Carbon Compounds, Vol. 1-5 and Supplementals (Elsevier Science Publishers, 1989); Organic Reactions, Vol. 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry, 4$^{th}$ Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

The processes described herein can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry, or by chromatography such as high pressure liquid chromatography (HPLC), gas chromatography (GC), gel-permeation chromatography (GPC), or thin layer chromatography (TLC).

Combination Therapies

The compounds identified using the methods described here are useful in the methods of the invention in combination with one or more additional agents useful for treating EBV infection and/or EBV-associated cancer. These additional agents may comprise compounds identified herein or agents, e.g., commercially available agents, known to treat, prevent, or reduce the symptoms of EBV infection and/or EBV-associated cancer.

One or more compounds of the invention described herein may be administered to a patient in need thereof with one or more of these agents. In certain embodiments, the compound of the invention is combined with one or more of agents, i.e., delivered to the patient concurrently. In other embodiment, the compound of the invention is delivered to the patient concurrently therewith one or more of these agents. In yet other embodiments, the compound of the invention is delivered prior to one or more of these agents. In yet other embodiments, the compound of the invention is delivered subsequent to one or more of these agents.

As used herein, combination of two or more compounds/agents may refer to a composition wherein the individual compounds/agents are physically mixed or wherein the individual compounds/agents are physically separated. A combination therapy encompasses administering the components/agents separately to produce the desired additive, complementary or synergistic effects. In certain embodiments, the compound and the agent are physically mixed in the composition. In other embodiments, the compound and the agent are physically separated in the composition.

The compounds identified using the methods described here are useful in the methods of the invention in combination with one or more additional treatment protocol useful for treating EBV infection and/or EBV-associated cancer. These additional treatment protocols can comprise treatment protocols and/or adjunctive therapies known to treat, prevent, or reduce the symptoms of EBV infection and/or EBV-associated cancer.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Kits

Also provided are kits or packages of pharmaceutical formulations containing (i) at least one compound of the invention; and (ii) an antiviral and/or anticancer agent. In certain embodiments, the compound of the invention and the antiviral and/or anticancer agent are formulated for the desired delivery vehicle and route. In certain embodiments, the kit is also includes a chemotherapeutic agent described herein. In other embodiments, the compound and antiviral and/or anticancer agent are formulated for any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In yet other embodiments, the kit is designed for delivery at home. The kit can thus include tubes or other containers, applicators, needles, syringes, and other appropriate packaging and instructions for use.

Methods

The invention provides a method of treating and/or preventing a disease or disorder caused by EBNA1 activity in a subject. The invention further provides a method of treating and/or preventing Epstein-Barr Virus (EBV) infection, and/or a disease or disorder associated with EBV infection, in a subject. The invention further provides a method of treating and/or preventing lytic and/or latent EBV infection in a subject.

In certain embodiments, the disease or disorder is infectious mononucleosis. In certain embodiments, the disease or disorder is chronic fatigue syndrome. In certain embodiments, the disease or disorder is multiple sclerosis. In certain embodiments, the disease or disorder is systemic lupus erythematosus. In certain embodiments, the disease or disorder is rheumatoid arthritis. In certain embodiments, the disease or disorder is cancer. In certain embodiments, the cancer is at least one selected from the group consisting of nasopharyngeal carcinoma, gastric carcinomas, non-Hodgkin's lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmacytic lymphoma, nodal marginal zone B cell lymphoma, splenic marginal zone lymphoma, intravascular large B-cell lymphoma, primary effusion lymphoma, lymphomatoid granulomatosis, angioimmunoblastic lymphadenopathy, leiomyosarcomas, X-linked lymphoproliferative disease, post-transplant lymphoproliferative disorders (PTLDs), Hodgkin's lymphoma and breast cancer. In certain embodiments, the cancer is nasopharyngeal carcinoma. In certain embodiments, the cancer is gastric carcinoma. In certain embodiments, the cancer is non-Hodgkin's lymphoma. In certain embodiments, the cancer is a post-transplant lymphoproliferative disorder.

In certain embodiments, the methods of the invention comprise administering a therapeutically effective amount of a compound and/or composition of the invention to the subject in need thereof. In other embodiments, the compound of the invention is part of a pharmaceutical composition further comprising at least one pharmaceutically acceptable carrier. In yet other embodiments, the compound and/or composition is administered to the subject by at least one route selected from the group consisting of oral, nasal, inhalational, topical, buccal, rectal, pleural, peritoneal, vaginal, intramuscular, subcutaneous, transdermal, epidural, intratracheal, otic, intraocular, intrathecal, and intravenous routes. In yet other embodiments, the compound and/or composition is administered orally. In yet other embodiments, the compound is administered as part of a pharmaceutical composition. In yet other embodiments, the subject is a mammal. In yet other embodiments, the mammal is human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent in the composition. In yet other embodiments, the compound of the invention is the only biologically active agent in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In a non-limiting example, the compounds for use in the invention may be formulated for oral administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration.

Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age, sex and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods:

X-Ray Powder Diffraction (XRPD):

PANalytical Empyrean XRPD:

X-Ray Powder Diffraction (XRPD) patterns were collected on a PANalytical Empyrean diffractometer using Cu Kα radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The instrument was performance checked using silicon powder on a weekly basis. The software used for data collection was X'Pert Data Collector v. 5.3, and the data were analyzed and presented using Diffrac Plus EVA v. 15.0.0.0 or Highscore Plus v. 4.5.

Samples were prepared and analyzed in either a metal or Millipore 96 well-plate in transmission mode. X-ray transparent film was used between the metal sheets on the metal well-plate and powders (approximately 1-2 mg) were used as received. The Millipore plate was used to isolate and analyze solids from suspensions by adding a small amount of suspension directly to the plate before filtration under a light vacuum.

The scan mode for the metal plate used the gonio scan axis, whereas a 2θ scan was utilized for the Millipore plate. A performance check was carried out using silicon powder (metal well-plate). The details of the data collection were: Angular range of 2.5 to 32.0° 2θ; Step size of 0.0130° 2θ; Total collection time of 2.07 min.

Bruker AXS C2 GADDS:

X-Ray Powder Diffraction (XRPD) patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Göbel multilayer mirror coupled with a pinhole collimator of 0.3 mm. A weekly performance check was carried out using a certified standard NIST 1976 Corundum (flat plate). The beam divergence, i.e. the effective size of the X-ray beam on the sample, was approximately 4 mm. A θ-θ continuous scan mode was employed with a sample—detector distance of 20 cm which gives an effective 2θ range of 3.2°-29.7°. Typically the sample would be exposed to the X-ray beam for 120 seconds. The software used for data collection was GADDS for XP/2000 4.1.43 and the data were analyzed and presented using Diffrac Plus EVA v15.0.0.0.

Ambient Conditions:

Samples run under ambient conditions were prepared as flat plate specimens using powder as received without grinding. Approximately 1-2 mg of the sample was lightly pressed on a glass slide to obtain a flat surface.

Non-Ambient Conditions:

Samples run under non-ambient conditions were mounted on a silicon wafer with heat-conducting compound. The sample was then heated to the appropriate temperature at 30° C./min and subsequently held isothermally for 1 minute before data collection was initiated.

Bruker AXS D8 Advance:

X-Ray Powder Diffraction (XRPD) patterns were collected on a Bruker D8 diffractometer using Cu Kα radiation (40 kV, 40 mA), θ–2θ goniometer, and divergence of V4 and receiving slits, a Ge monochromator and a Lynxeye detector. The instrument was performance checked using a certified Corundum standard (NIST 1976). The software used for data collection was Diffrac Plus XRD Commander v2.6.1 and the data were analyzed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection were: Angular range of 2 to 42° 2θ; Step size of 0.05° 2θ; Collection time of 0.5 s/step.

Proton Nuclear Magnetic Resonance ($^1$H NMR):

$^1$H NMR spectra were collected on a Bruker 400 MHz instrument equipped with an auto-sampler and controlled by a DRX400 console. Automated experiments were acquired using ICON-NMR v4.0.7 running with Topspin v1.3 using the standard Bruker loaded experiments. For non-routine spectroscopy, data were acquired through the use of Topspin alone. Samples were prepared in DMSO-$d_6$, unless otherwise stated. Off-line analysis was carried out using ACD Spectrus Processor 2014.

Differential Scanning Calorimetry (DSC):

DSC data were collected on a TA Instruments Discovery DSC equipped with a 50 position auto-sampler. The calibration for thermal capacity was carried out using sapphire and the calibration for energy and temperature was carried out using certified indium. Typically 0.5-3 mg of each sample, in a pin-holed aluminium pan, was heated at 10° C./min from 25° C. to 300° C. A purge of dry nitrogen at 50 ml/min was maintained over the sample. Modulated temperature DSC was carried out using an underlying heating rate of 2° C./min and temperature modulation parameters of ±0.318° C. (amplitude) every 60 seconds (period). The instrument control and data analysis software was TRIOS v3.2.0.3877.

Thermo-Gravimetric Analysis (TGA):

TGA data were collected on a TA Instruments Discovery TGA, equipped with a 16 or 25 position auto-sampler. The instrument was temperature calibrated using certified alumel and nickel. Typically 5-10 mg of each sample was loaded onto a pre-tared aluminium DSC pan and heated at 10° C./min from ambient temperature to 350° C. A nitrogen purge at 25 or 60 ml/min was maintained over the sample. The instrument control and data analysis software was TRIOS v3.2.0.3877.

Polarized Light Microscopy (PLM):

Samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-colour filter.

Scanning Electron Microscopy (SEM):

Data were collected on a Phenom Pro Scanning Electron Microscope. A small quantity of sample was mounted onto an aluminum stub using conducting double-sided adhesive tape. A thin layer of gold was applied using a sputter coater (20 mA, 120 s).

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Ca. 10 mg of sample was used per titration and duplicate determinations were made. Data collection and analysis using Tiamo v2.2.

Chemical Purity Determination by HPLC:

Purity analysis was performed on an Agilent HP1100 series system equipped with a diode array detector and using ChemStation software vB.04.03 using the method detailed in Table 1.

TABLE 1

HPLC method for chemical purity determinations.

| Parameter | Value | | |
|---|---|---|---|
| Type of method | Reverse phase with gradient elution | | |
| Sample Preparation | 0.5 mg/ml in acetonitrile:water 1:1 | | |
| Column | Supelco Ascentis Express C18, 100 × 4.6 mm, 2.7 μm | | |
| Column Temperature (° C.) | 25 | | |
| Injection (μl) | 2 | | |
| Wavelength, Bandwidth (nm) | 255, 90 | | |
| Flow Rate (ml/min) | 2 | | |
| Phase A | 0.1% TFA in water | | |
| Phase B | 0.085% TFA in acetonitrile | | |
| | Time (min) | % Phase A | % Phase B |
| Timetable | 0 | 95 | 5 |
| | 6 | 5 | 95 |
| | 6.2 | 95 | 5 |
| | 8 | 95 | 5 |

Gravimetric Vapour Sorption (GVS):

Sorption isotherms were obtained using a SMS DVS Intrinsic moisture sorption analyzer, controlled by DVS Intrinsic Control software. The sample temperature was maintained at 25° C. by instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change (mass relaxation) of the sample as a function of % RH was constantly monitored by the microbalance (accuracy ±0.005 mg).

Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was carried out using Microsoft Excel. The sample was recovered after completion of the isotherm and re-analyzed by XRPD.

TABLE 2

Method for SMS DVS intrinsic experiments.

| Parameter | Value |
|---|---|
| Adsorption - Scan 1 | 40-90 |
| Desorption/Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |

Ion Chromatography (IC):

Data were collected on a Metrohm 930 Compact IC Flex with 858 Professional autosampler and 800 Dosimo dosage unit monitor, using IC MagicNet software v3.1. Accurately weighed samples were prepared as stock solutions in an appropriate dissolving solution and diluted appropriately prior to testing. Quantification was achieved by comparison with standard solutions of known concentration of the ion being analyzed.

TABLE 3

IC method for cation chromatography.

| Parameter | Value |
|---|---|
| Type of method | Cation exchange |
| Column | Metrosep C 4 - 250 (4.0 × 250 mm) |
| Column Temperature (° C.) | Ambient |
| Injection (μl) | Various |
| Detection | Conductivity detector |
| Flow Rate (ml/min) | 0.9 |
| Eluent | 1.7 mM Nitric Acid 0.7 mM Dipicolinic acid in a 5% acetone aqueous solution. |

TABLE 4

IC method for anion chromatography.

| Parameter | Value |
|---|---|
| Type of method | Anion exchange |
| Column | Metrosep A Supp 5 - 150 (4.0 × 150 mm) |
| Column Temperature (° C.) | Ambient |
| Injection (μl) | Various |
| Detection | Conductivity detector |
| Flow Rate (ml/min) | 0.7 |
| Eluent | 3.2 mM sodium carbonate, 1.0 mM sodium hydrogen carbonate in a 5% acetone aqueous solution. |

Thermodynamic Solubility:

Aqueous solubility was determined by suspending sufficient compound in SGF or FeSSIF to give a maximum final concentration of ≥30 mg/ml of the parent free form of the compound. The suspension was equilibrated at 25° C. for 24 hours (750 rpm), and then the pH was measured. The suspension was filtered through a glass fibre C filter (particle retention>1.2 μm). The filtrate was then diluted by an appropriate factor. Quantitation was by HPLC with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection.

TABLE 5

HPLC method for solubility measurements.

| Parameter | Value | | |
|---|---|---|---|
| Type of method | Reverse phase with gradient elution | | |
| Column | Phenomenex Luna, C18 (2) 5 μm 50 × 4.6 mm | | |
| Column Temperature (° C.) | 25 | | |
| Standard Injections (μl) | 1, 2, 3, 4, 5, 7 | | |
| Test Injections (μl) | 1, 2, 3, 10, 15, 20 | | |
| Detection: Wavelength, Bandwidth (nm) | 260, 90 | | |
| Flow Rate (ml/min) | 2 | | |
| Phase A | 0.1% TFA in water | | |
| Phase B | 0.085% TFA in acetonitrile | | |
| | Time (min) | % Phase A | % Phase B |
| Timetable | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Analysis was performed on an Agilent HP1100 series system equipped with a diode array detector and using ChemStation software vB.04.03.

Results are now illustrated.

Example 1: Studies of Crystalline Forms of (I) Free Base 1.1. Purification of Supplied Amorphous (I) Free Acid:

Procedure A: (I) free acid (ca. 75 mg) was suspended in water (10 vol, 750 μl). The solid did not wet well, and therefore the mixture was shaken thoroughly prior to stirring at 25° C. for 2 hours. The solid was then isolated by filtration (gravity, aided by an air flow). The material was analyzed by XRPD and IC.

Procedure B: (I) free acid (ca. 750 mg) was suspended in water (10 vol, 7.5 ml). The mixture was shaken thoroughly and stirred at 25° C. for 30 minutes. The suspension was split into two vials. The solids were filtered by gravity or suction and then dried under vacuum. The two batches were analyzed by IC, HPLC and XRPD.

A XRPD trace for amorphous (I) free base is illustrated in FIG. 2.

1.2. Preliminary Solubility Assessment and Crystallization Screen:

Amorphous (I) free acid (post washing, ca. 20 mg) was dissolved or suspended in a range of solvent systems (using 10 or 20 volumes) at RT. Solutions were placed in a fridge at 4° C. overnight. If no solid was obtained, the solution was then allowed to evaporate at RT. Suspensions were matured between RT-50° C. heat-cool cycles (8 h per cycle) for up to 7 days. Solids were analyzed by XRPD.

1.3. Crystallization Experiments; Scale-Up:

(I) free acid (150 mg) was dissolved or suspended in the selected solvents at RT. Solutions were set for slow evaporation at RT, and the suspensions were matured using heat-cool cycles (8 h per cycle) for 11 days. The solids were analyzed by XRPD after filtration under vacuum.

1.4. Grinding in Water:

(I) free acid (ca. 30 mg) was initially wetted with 20 µl of water and ground for 2 h at 650 rpm using a Fritsch milling system with an Automaxion adapter in presence of two grinding beads. The samples obtained after this grinding procedure were air dried for 5 min, and analyzed by XRPD.

1.5. Amorphous (I) Free Acid:

A summary of characterization data of the supplied amorphous (I) is shown in Table 6.

TABLE 6

| (I) free acid amorphous material. | |
|---|---|
| Technique | Results |
| XRPD (FIG. 2) | Amorphous. Small peaks consistent with sodium chloride at 31.8 °2-theta. |
| $^1$H NMR | Spectrum was consistent with structure. |
| TGA (FIG. 3) | 0.6% w/w loss below 85° C. |
| DSC (FIG. 3) | Broad endotherms with onset between 35-90° C. Decomposition was observed above 200° C. |
| MDSC (FIG. 4) | Glass transition at 79.5° C. No evidence of crystallization. |
| Ion Chromatography | 0.5% w/w Cl; 0.3% w/w Na. |
| SEM/PLM (FIGS. 5-6) | Agglomerates of irregular fibres/particles. |
| Purity by HPLC | 95.5% (AUC). |
| Storage at 40° C./ 75% RH for 8 weeks | Unchanged by XRPD. 93.5% (AUC) purity. |
| Storage at 25° C./ 97% RH for 8 weeks | Amorphous by XRPD. Peak for NaCl not present. 91.5% (AUC) purity. |
| Storage at 60° C. for 8 weeks | Unchanged by XRPD. 94.4% (AUC) purity. |
| GVS | 5.5% w/w reversible moisture uptake between 0-90% RH with hysteresis. Unchanged by XRPD. |
| KF | 2.0% w/w water. |

Amorphous (I) free acid was supplied with a purity of 95.5% (AUC). The material contained sodium chloride as an impurity, as observed by XRPD and son Chromatography. No evidence of crystallization was observed upon heating prior the decomposition ca. 200° C. The material is hygroscopic, showing ca. 5.50% moisture uptake between 0-90% RH. An extended stability study was carried out, showing the material was unchanged by XRPD after 8 weeks storage at 40° C./75% RH and 60° C./room humidity. The material showed a completely amorphous trace by XRPD after 8 weeks stored at 25° C./97 RH, i.e. the sodium chloride peak was not observed. A slight decrease in chemical purity was observed in all the cases after storage.

1.6. Crystalline (I) Free Acid:

A summary of the characterization data for crystalline (I) free acid is shown in Table 7.

TABLE 7

| Crystalline material of (I) free acid. | |
|---|---|
| Technique | (I) Free Acid - Crystalline Material |
| XRPD (FIG. 7) | Crystalline. Denoted as Pattern 1 (reference) |
| $^1$H NMR | Spectrum was consistent with structure. 0.9 eq. dichloromethane (DCM) |
| TGA (FIG. 8) | 10.4% w/w loss below 115° C., followed by a further loss of 3.9% w/w below 185° C. |

TABLE 7-continued

| Crystalline material of (I) free acid. | |
|---|---|
| Technique | (I) Free Acid - Crystalline Material |
| DSC (FIG. 8) | Sharp endotherm with onset at 94.3° C. (87.4 J/g). Decomposition was observed above 225° C. |
| Ion Chromatography | 0.3% w/w Cl; 0.8% w/w Na |
| SEM/PLM (FIGS. 9-10) | Agglomerates of irregular prismatic crystals |
| Purity by HPLC | 97.2% (AUC) |
| Storage at 40° C./ 75% RH for 4 weeks | Unchanged by XRPD. |
| Storage at 25° C./ 97% RH for 4 weeks | Unchanged by XRPD. |
| KF | 0.3% w/w water |

Crystalline (I) was suspected to be a DCM solvate with a purity of 97.2% (AUC). The material contains 0.9 equivalents DCM by $^1$H-NMR (also consistent with the weight loss observed on the TGA thermogram). The material decomposition was observed from ca. 225° C. The material remained unchanged by XRPD after storage at 40° C./75% RH and 25° C./97% RH for up to 4 weeks.

1.7. Long-Term Stability Study:

Amorphous (I) free acid was stored at 40° C./75% RH (open vial), 25° C./97% RH (open vial) and 60° C. (closed vial, ambient humidity) for 8 weeks. Amorphous (I) free acid showed amorphous traces after storage up to 8 weeks at 60° C./ambient humidity, 40° C./75% RH and 25° C./97% RH. However, the latter conditions resulted in the absence of the characteristic peak for sodium chloride, suggesting high humidity atmosphere may be sufficient to dissolve the impurity.

A decrease in the chemical purity was observed in all three cases after 8 weeks. Storage at 60° C. resulted in the smallest decrease in purity out of the three conditions (1.1% (AUC)). The degree of degradation appeared to be in trend with the increasing humidity and, thus, the purity of the sample stored at 25° C./97% RH showed the lowest purity at 91.5% (AUC) (4.0% (AUC) decrease). The purity of the sample stored at 40° C./75% RH for 8 weeks showed a decrease of 2.0% (AUC).

Two samples of (I) were initially supplied. The main batch was amorphous and hygroscopic, with a purity of 95.5% (AUC). The crystalline batch was a suspected DCM solvate, which remained unchanged by XRPD after 4 weeks storage at 40° C./75% RH and 25° C./97% RH.

1.8. Purification of Amorphous Material:

Washing experiments using water were carried out in order to reduce the amount of residual sodium chloride detected in the supplied amorphous (I) free acid material. The purification methods are summarized elsewhere herein. The solids were analyzed by XRPD and IC after the washing procedures. Fully amorphous traces were observed by XRPD, with no evidence of the sodium chloride characteristic peaks. Ion chromatography showed a decrease in the amount of sodium and chloride ions. No decrease in the purity of the material was observed. The amorphous (I) free acid did not wet easily, and vigorous shaking was needed in order to reach good mixing of solid and solvent. The material was difficult to rinse from original vial and filtration device and therefore the recoveries were generally low. Given that the reduction in sodium and chloride amount is generally low and the washing procedure is not straightforward, it was decided to use the material as supplied for the salt screen and further work.

1.9. Solubility Assessment and Crystallization Screen:

The solubility assessment and crystallization screen were set up with the aim of exploring the polymorphic landscape of (I), as well as selecting the most appropriate solvents for the salt screen.

(I) free acid was soluble in 10 volumes of the majority of the solvents used with the exception of heptane, water, toluene and nitromethane. Nonetheless, the latter two solvents produced crystalline forms after maturation for 7 days (Patterns 2 and 4 respectively).

Several crystalline materials were obtained from cooling or evaporation of solutions. Two further samples produced crystalline material. Crystallization from DCM produced Pattern 1, consistent with the supplied crystalline material. Additionally, crystals obtained from acetone: 5% water exhibited a new crystalline pattern, denoted Pattern 3. Several gums and oils were also obtained after evaporation of the relevant solvents. No further work was carried out on these materials.

A summary of the results is found in Table 8 and an overlay of the crystalline patterns is shown in FIG. 21.

Crystalline Patterns 2, 3, and 4 were reproduced on a 150 mg scale. Experimental details are found in Table 9. The experiments using acetone and acetone: 5% water produced the same form, Pattern 3. Only one solid (from acetone) was characterized.

Characterization by XRPD, ¹H NMR, TGA, DSC and storage at 40° C./75% RH for one week was carried out. Details are found in Table 10.

The three crystalline materials contained significant amounts of residual solvent by ¹H NMR and remained unchanged after storage at 40° C./75% RH for one week. TGA and DSC showed significant weight losses, consistent with solvent loss as well as sharp endotherms. Nitromethane is an exception to this, and TGA analysis showed gradual weight loss which eventually resulted in decomposition. The weight losses have been quoted up to the sharp endotherm observed by DSC. The solvent content and stability observed suggested that the materials might be solvated forms.

TABLE 8

Solubility assessment and crystallization screen.

| Solvent | Solubility assessment | | | | Procedure | Obs. Overnight | Further work | XRPD |
|---|---|---|---|---|---|---|---|---|
| | 10 vol | Obs. | 20 vol | Obs. | | | | |
| 1,4-Dioxane | ✓ | Solution | N/A | N/A | Cooling at 4° C. | Solution | Evaporation | N/A (oil) |
| Ethanol | ✓ | Solution | N/A | N/A | Cooling at 4° C. | Solution | Evaporation | N/A (oil) |
| Tetrahydrofuran | ✓ | Solution | N/A | N/A | Cooling at 4° C. | Solution | Evaporation | N/A (oil) |
| Acetonitrile | ✓ | Solution | N/A | N/A | Cooling at 4° C. | Solution | Evaporation | N/A (oil) |
| Methanol | ✓ | Solution | N/A | N/A | Cooling at 4° C. | Solution | Evaporation | Amorphous |
| Acetone | ✓ | Solution | N/A | N/A | Cooling at 4° C. | Crystals | Evaporation of bulk gave gum | N/A |
| 2-Propanol | ✓ | Solution | N/A | N/A | Cooling at 4° C. | Solution | Evaporation | N/A (oil) |
| Methylethyl Ketone | ✓ | Solution | N/A | N/A | Cooling at 4° C. | Solution | Evaporation | N/A (oil) |
| Methylisoburyl Ketone | ✓ | Solution | N/A | N/A | Cooling at 4° C. | Solution | Evaporation | N/A (oil) |
| Ethyl Acetate | ✓ | Solution | N/A | N/A | Cooling at 4° C. | Solution | Evaporation | N/A (oil) |
| Toluene | x | Gummy solid | x | Gummy solid | Maturation RT-50° C. | Solid + crystals | N/A | Crystalline Pattern 2 |
| Anisole | ✓ | Solution | N/A | N/A | Cooling at 4° C. | Solution | Evaporation | Ongoing |
| Dichloromethane | ✓ | Solution | N/A | N/A | Cooling at 4° C. | Crystals | N/A | Crystalline Pattern 1 |
| Nitromethane | x | Gummy solid | x | Gummy solid | Maturation RT-50° C. | Gum | Maturation RT-50° C. for 7 days | Crystalline Pattern 4 |
| Heptane | x | Suspension | x | Suspension | Maturation RT-50° C. | Solution | Maturation RT-50° C. for 7 days | Amorphous |
| Acetone/5% water | ✓ | Solution | N/A | N/A | Cooling at 4° C. | Solution | Evaporation | Crystalline Pattern 3 |
| Ethanol/5% water | ✓ | Solution | N/A | N/A | Cooling at 4° C. | Solution | Evaporation | N/A (oil) |
| Water | x | Suspension* | x | Suspension* | Maturation RT-50° C. | Wet solid | Maturation RT-50° C. for 7 days | Amorphous |

Further experiments were carried out, involving heating, vacuum drying and/or grinding the materials in order to assess the stability of the solvated materials and the potential crystallization of an anhydrous form by desolvation. A summary of these data can be found in Table 11.

The materials appeared to keep a consistent amount of solvent after vacuum drying or storage at elevated temperature/humidity. The Pattern 2 material, containing 0.5 equivalents toluene as prepared, showed a decrease in the amount of toluene after grinding and drying, although a significant loss of crystallinity was also observed. These findings suggested that the crystalline forms contained the solvent, and anhydrous materials cannot be produced by drying these materials i.e. strong interaction between the solvent and the API.

TABLE 9

Scale-up crystallization experiments for crystalline forms of (I) free acid.

| Solvent | Observations | Procedure | Observations | XRPD |
|---|---|---|---|---|
| Toluene (13 vol) | Gum | Maturation | Solid observed after 11 days maturation | Crystalline, Pattern 2 |
| Acetone: 5% water (10 vol) | Solution (green shade) | Slow evaporation | Large crystals | Crystalline, Pattern 3 |
| Acetone (10 vol) | Solution (green shade) | Slow evaporation | Large crystals | Crystalline, Pattern 3, |
| Nitromethane (13 vol) | Gum | Maturation | Solid observed after 11 days maturation | Crystalline, Pattern 4, |
| Acetone: 20% water (10 vol) | Solution (green shade) | Evaporation | Large crystals | Crystalline, Pattern 3, |

TABLE 10

Characterization of crystalline forms of (I) free acid.

| Solvent | XRPD (dried) | $^1$H-NMR | TGA and DSC | Storage at 40° C./ 75% RH for 7 days |
|---|---|---|---|---|
| Toluene | Crystalline, Pattern 2, | 0.5 eq. toluene | 5.5% weight loss below 160° C. Sharp endotherm at 114.7° C. | Unchanged |
| Acetone | Crystalline, Pattern 3, | 0.8 eq. acetone | 5.7% weight loss below 110° C. Sharp endotherm at 85.0° C. | Unchanged |
| Nitromethane | Crystalline, Pattern 4, | 0.2 eq. nitromethane | 2.1% weight loss below 125° C. Sharp endotherm at 102.3° C. | Unchanged |

TABLE 11

Further stability experiments on crystalline forms of (I) free acid.

| XRPD Solvent Content | Vacuum drying 40° C. or 55° C. | Grinding and vacuum drying at 55° C. | Storage at 40° C./ 75% RH for 3.5 days |
|---|---|---|---|
| Pattern 2 0.5 eq. toluene | Unchanged by XRPD or $^1$H NMR | Lower crystallinity. 0.3 eq. toluene | N/A |
| Pattern 3 0.8 eq. acetone | Unchanged by XRPD or $^1$H NMR | N/A | Unchanged by XRPD and $^1$H NMR |

1.10. Attempt to Prepare Crystalline Forms in Water:

Grinding in the presence of water was attempted in order to assess the potential formation of hydrated forms. An amorphous trace was obtained after grinding. The solid did not mix well with water and therefore, the solid was dry after the experiment. No further work was carried out on this sample.

1.11. Comments:

Four crystalline forms of (I) free acid were observed. All appeared to be solvates with varying amounts of solvent. The forms were stable at RT and after vacuum drying. No anhydrous forms were isolated by drying these solvates.

Example 2

As described elsewhere herein, a salt screening study identified 4 crystalline solvated forms of the (I) free base from DCM, toluene, acetone and nitromethane. A batch of (I) free acid, which was crystallized from EtOH/EtOAc, yielded another crystalline form (Pattern 5).

An illustrative non-limiting recrystallization process for (I) free acid involved dissolution in ethyl acetate (3.0 vol.) and ethanol (1.0 vol.) at 60-70° C. The solution was then cooled to 25-30° C. over a period of 1 h and stirred for 18 h. After 18 h, the mixture was further cooled to 0-5° C. and stirred for 6 h. The crystallized solids were filtered and dried.

2.1. Characterization of Supplied Material:

The received material (I) free acid was characterized using a wide range of techniques to investigate the solid form properties. A summary of the results is shown in Table 12.

Solid state characterization confirmed that the (I) free acid batch was crystalline (Pattern 5), non-solvated, non-hygroscopic material, which remained unchanged by XRPD after one week storage at elevated temperature and humidity levels (40° C./75% RH, and 25° C./97% RH).

The chemical purity of the material was 98.3% A.U.C. The purity was 98.0% A.U.C. after storage at the aforementioned conditions. This difference was not viewed as significant.

A sharp melt was observed on the DSC thermogram at 172.9° C., and by varying the heating rate, there was no sign of a peak shoulder preceding the main melting event, as observed previously with the EtOH/EtOAc batch.

There was a difference in the onset temperatures of the melt between this material and the EtOH/EtOAc materials (172.9° C. and 176.3° C., respectively at a heating rate of 10° C./min), possibly owing to differing purity/impurity profiles of the materials. Variable temperature XRPD experiment showed that the sample remained as Pattern 5 between 25-165° C.

TABLE 12

| Characterization data for (I) free acid. | |
|---|---|
| XRPD | Crystalline Pattern 5 |
| XRPD post 25° C./97% RH | Unchanged |
| XRPD post 40° C./75% RH | Unchanged |
| HPLC Purity (Pharmorphix generic method) | 98.3% A.U.C. |
| HPLC Purity after storage at 25° C./ 97% RH (Pharmorphix generic method) | 98.0% A.U.C. |
| HPLC Purity after storage at 40° C./ 75% RH (Pharmorphix generic method) | 98.0% A.U.C. |
| $^1$H-NMR | Consistent with the proposed structure; no signs of residual solvents |
| TGA (10° C./min) | Small weight loss of 0.15% w/w between 25-50° C. (possibly residual water) |
| DSC (2° C./min) | No signed of a shoulder* on the main endothermic event (melt = 172.4° C.) |
| DSC (10° C./min) | No signed of a shoulder* on the main endothermic event (melt = 172.9° C.) |
| DSC (50° C./min) | No signed of a shoulder* on the main endothermic event (melt = 174.3° C.) |
| KF | 0.1 |
| GVS | The sample is not hygroscopic. 0.3% uptake between 0-90% RH. A small hysteresis event between 40-90% RH. Unchanged by XRPD |
| PLM SEM | Small particles, which tended to from agglomerates |
| Variable temperature XRPD | Remained as Pattern 5 from 25-165° C. |

*A small shoulder was previously observed on the DSC thermogram of the EtOH/EtOAc batch. Melt of the EtOH/EtOAc batch material = 176.3° C. (onset temperature).

2.2. Stability Assessments of the Supplied Material:

The aim of this set of experiments was to test the stability of Pattern 5 in different conditions by slurring the material at either 4 or 50° C. in a range of 8 selected solvents including mixtures.

The supplied material was dissolved or suspended in the chosen solvent at r.t. Solvents were added in 10 vol. aliquots up to 30 vol. and observations were recorded; if a solution was obtained at any point then no further additions were made. Samples were kept at 4° C. or 50° C. over 16 h, and analyzed by XRPD. The solids were filtered and analyzed by XRPD. The solutions were allowed to evaporate at r.t. to afford solids which were also analyzed by XRPD.

TABLE 13

Stability assessments of the supplied material at 4° C.

| | Volumes (RT) | | | Observations Overnight at 4° C. maturation | Evaporation at r.t. | XRPD |
|---|---|---|---|---|---|---|
| Solvent | 10 | 20 | 30 | | | |
| EtOH | x | x | x | White Suspension | n/a | Pattern 5 crystalline |
| EtOAc | x | x | ✓ | Yellow Transparent solution | Solid | Pattern 5 crystalline |
| TBME | x | x | x | White Suspension | n/a | Pattern 5 crystalline |
| MIBK | x | x | x | Off-White Suspension | n/a | Pattern 5 crystalline |
| IPA | x | x | x | White Suspension | n/a | Pattern 5 crystalline |
| Heptane | x | x | x | White Suspension | n/a | Pattern 5 crystalline |
| EtOAc/EtOH (3:1) | x | ✓ | | Yellow Transparent solution | Solid | Pattern 5 crystalline |
| EtOAc/EtOH (1:3) | ✓ | | | Yellow Transparent solution | Solid | Pattern 5 crystalline |

✓ = solution; x = suspensions; n/a = solution

TABLE 14

Stability assessments of the supplied material at 50° C.

| Solvent | Volumes (RT) 10 | 20 | 30 | Observations Overnight at 50° C. maturation | Evaporation at r.t. | XRPD |
|---|---|---|---|---|---|---|
| EtOH | x | x | x | Yellow Transparent solution | Solid | Pattern 5 crystalline |
| EtOAc | x | x | ✓ | Yellow Transparent solution | Solid | Pattern 5 crystalline |
| TBME | x | x | x | White Suspension | n/a | Pattern 5 crystalline |
| MIBK | x | x | x | Yellow Transparent solution | Solid | Pattern 5 crystalline |
| IPA | x | x | x | Yellow Transparent solution + yellow solid | Solid | Pattern 5 crystalline |
| Heptane | x | x | x | White Suspension | n/a | Pattern 5 crystalline |
| EtOAc/EtOH (3:1) | x | ✓ | | Yellow Transparent solution + yellow solid | Solid | Pattern 5 crystalline |
| EtOAc/EtOH (1:3) | ✓ | | | Yellow Transparent solution + yellow solid | Solid | Pattern 5 crystalline |

✓ = solution; x = suspensions; n/a = solution

Stability assessment on Pattern 5 material showed either slurries with no change in solid form in a range of solvents. At a higher temperature (50° C.) the input material (Pattern 5) was more soluble in a number of solvents, and solutions were subsequently allowed to evaporate, whereupon solids obtained were also all Pattern 5 material.

TABLE 15

Selected peak listing of certain XRPD spectra.

| Angle 2-Theta ° | Intensity % |
|---|---|
| Pattern 1 | |
| 2θ angle: 6.9; 8.4; 9.8; 11.0; 12.8; 14.7; 15.3; 16.5; 16.9; 17.9; 18.2; 18.7; 19.0; 19.6; 20.0; 20.3; 20.9; 21.4; 22.2; 23.9; 24.5; 24.8; 25.4; 25.9; 26.1; 27.1; 28.7; 29.2; 29.7 | |
| 6.9 | 6.1 |
| 8.4 | 9.3 |
| 9.8 | 3.8 |
| 11.0 | 12.2 |
| 12.8 | 7.6 |
| 14.7 | 4.2 |
| 15.3 | 5.2 |
| 16.5 | 50.5 |
| 16.9 | 38.7 |
| 17.9 | 8.0 |
| 18.2 | 9.9 |
| 18.7 | 15.8 |
| 19.0 | 19.1 |
| 19.6 | 100.0 |
| 20.0 | 10.8 |
| 20.3 | 15.3 |
| 20.9 | 29.5 |
| 21.4 | 46.0 |
| 22.2 | 18.3 |
| 23.9 | 9.3 |
| 24.5 | 15.0 |
| 24.8 | 8.9 |
| 25.4 | 21.6 |
| 25.9 | 23.6 |
| 26.1 | 31.6 |
| 27.1 | 7.0 |

TABLE 15-continued

Selected peak listing of certain XRPD spectra.

| Angle 2-Theta ° | Intensity % |
|---|---|
| 28.7 | 7.4 |
| 29.2 | 13.9 |
| 29.7 | 11.0 |
| Pattern 2 | |
| 2θ angle: 7.1; 7.9; 8.6; 9.4; 10.1; 10.5; 11.7; 12.7; 13.3; 14.3; 14.7; 15.0; 15.5; 16.0; 16.3; 16.6; 17.2; 17.8; 18.5; 18.9; 19.5; 20.3; 20.8; 21.6; 22.0; 22.7; 23.0; 23.5; 24.0; 24.6; 24.9; 25.6; 26.2; 26.7; 27.2; 27.8; 28.8; 29.2; 29.7. | |
| 7.1 | 14.8 |
| 7.9 | 3.0 |
| 8.6 | 20.7 |
| 9.4 | 6.4 |
| 10.1 | 6.3 |
| 10.5 | 16.4 |
| 11.7 | 2.9 |
| 12.7 | 2.0 |
| 13.3 | 10.0 |
| 14.3 | 8.2 |
| 14.7 | 3.1 |
| 15.0 | 4.6 |
| 15.5 | 15.7 |
| 16.0 | 18.4 |
| 16.3 | 29.1 |
| 16.6 | 3.8 |
| 17.2 | 4.3 |
| 17.8 | 31.6 |
| 18.5 | 47.2 |
| 18.9 | 100.0 |
| 19.5 | 16.7 |
| 20.3 | 11.1 |
| 20.8 | 6.9 |
| 21.6 | 79.2 |
| 22.0 | 11.1 |
| 22.7 | 6.8 |
| 23.0 | 19.7 |
| 23.5 | 15.4 |
| 24.0 | 10.2 |
| 24.6 | 5.9 |
| 24.9 | 6.0 |
| 25.6 | 13.3 |
| 26.2 | 6.1 |
| 26.7 | 15.4 |
| 27.2 | 7.3 |
| 27.8 | 5.8 |

TABLE 15-continued

Selected peak listing of certain XPRD spectra.

| Angle 2-Theta ° | Intensity % |
|---|---|
| 28.8 | 7.6 |
| 29.2 | 4.7 |
| 29.7 | 6.1 |
| Pattern 3 | |
| 2θ angle: 6.8; 8.3; 12.5; 12.8; 13.7; 15.4; 16.8; 17.8; 19.0; 19.3; 19.9; 20.7; 21.3; 21.8; 22.2; 22.9; 23.6; 24.2; 25.3; 25.7; 26.2; 26.5; 27.6; 28.5; 29.0; 29.5. | |
| 6.8 | 10.1 |
| 8.3 | 35.9 |
| 12.5 | 29.1 |
| 12.8 | 13.5 |
| 13.7 | 8.9 |
| 15.4 | 13.3 |
| 16.8 | 100.0 |
| 17.8 | 26.0 |
| 19.0 | 27.0 |
| 19.3 | 30.4 |
| 19.9 | 23.1 |
| 20.7 | 74.0 |
| 21.3 | 15.7 |
| 21.8 | 8.5 |
| 22.2 | 7.5 |
| 22.9 | 11.2 |
| 23.6 | 13.0 |
| 24.2 | 12.3 |
| 25.3 | 20.5 |
| 25.7 | 11.8 |
| 26.2 | 18.2 |
| 26.5 | 13.3 |
| 27.6 | 7.1 |
| 28.5 | 9.8 |
| 29.0 | 13.7 |
| 29.5 | 5.4 |
| Pattern 4 | |
| 2θ angle: 7.7; 8.2; 10.6; 11.2; 15.3; 16.9; 17.7; 18.8; 19.5; 21.2; 21.7; 22.5; 22.9; 23.4; 24.2; 25.2; 27.9. | |
| 7.7 | 21.2 |
| 8.2 | 3.1 |
| 10.6 | 6.6 |
| 11.2 | 3.3 |
| 15.3 | 6.1 |
| 16.9 | 27.1 |
| 17.7 | 18.2 |
| 18.8 | 3.3 |
| 19.5 | 4.1 |
| 21.2 | 11.5 |
| 21.7 | 12.8 |
| 22.5 | 5.7 |
| 22.9 | 6.6 |
| 23.4 | 100.0 |
| 24.2 | 6.5 |
| 25.2 | 6.7 |
| 27.9 | 5.8 |
| Pattern 5 | |
| 2θ angle: 9.4; 11.9; 12.6; 13.7; 15.2; 15.3; 18.0; 18.9; 19.4; 20.1; 20.5; 20.7; 21.3; 22.8; 23.3; 23.9; 24.3; 25.4; 25.8; 27.3; 27.6; 28.1; 29.3; 29.8. | |
| 9.4 | 3.4 |
| 11.9 | 9.1 |
| 12.6 | 2.5 |
| 13.7 | 5.1 |
| 15.2 | 9.8 |
| 15.3 | 10.7 |
| 18.0 | 9.1 |
| 18.9 | 100.0 |
| 19.4 | 3.6 |
| 20.1 | 7.4 |
| 20.5 | 22.2 |
| 20.7 | 3.5 |
| 21.3 | 7.1 |
| 22.8 | 7.1 |
| 23.3 | 5.1 |

TABLE 15-continued

Selected peak listing of certain XPRD spectra.

| Angle 2-Theta ° | Intensity % |
|---|---|
| 23.9 | 7.4 |
| 24.3 | 7.3 |
| 25.4 | 3.5 |
| 25.8 | 5.5 |
| 27.3 | 2.2 |
| 27.6 | 2.4 |
| 28.1 | 10.2 |
| 29.3 | 2.6 |
| 29.8 | 2.7 |

Enumerated Embodiments

The following exemplary embodiments are provided, the numbering of which is not to be construed as designating levels of importance.

Embodiment 1(a) provides 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern corresponding to Crystalline Form 1, with a X-ray powder diffraction spectrum comprising 2θ values (in degrees) of about: 6.9; 8.4; 9.8; 11.0; 12.8; 14.7; 15.3; 16.5; 16.9; 17.9; 18.2; 18.7; 19.0; 19.6; 20.0; 20.3; 20.9; 21.4; 22.2; 23.9; 24.5; 24.8; 25.4; 25.9; 26.1; 27.1; 28.7; 29.2; 29.7; wherein the XRDP is measured with a Copper X-ray source.

Embodiment 1(b) provides 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern corresponding to Crystalline Form 2, with a X-ray powder diffraction spectrum comprising 2θ values (in degrees) of about: 7.1; 7.9; 8.6; 9.4; 10.1; 10.5; 11.7; 12.7; 13.3; 14.3; 14.7; 15.0; 15.5; 16.0; 16.3; 16.6; 17.2; 17.8; 18.5; 18.9; 19.5; 20.3; 20.8; 21.6; 22.0; 22.7; 23.0; 23.5; 24.0; 24.6; 24.9; 25.6; 26.2; 26.7; 27.2; 27.8; 28.8; 29.2; 29.7; wherein the XRDP is measured with a Copper X-ray source.

Embodiment 1(c) provides 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern corresponding to Crystalline Form 3, with a X-ray powder diffraction spectrum comprising 2θ values (in degrees) of about: 6.8; 8.3; 12.5; 12.8; 13.7; 15.4; 16.8; 17.8; 19.0; 19.3; 19.9; 20.7; 21.3; 21.8; 22.2; 22.9; 23.6; 24.2; 25.3; 25.7; 26.2; 26.5; 27.6; 28.5; 29.0; 29.5; wherein the XRDP is measured with a Copper X-ray source.

Embodiment 1(d) provides 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern corresponding to Crystalline Form 4, with a X-ray powder diffraction spectrum comprising 2θ values (in degrees) of about: 7.7; 8.2; 10.6; 11.2; 15.3; 16.9; 17.7; 18.8; 19.5; 21.2; 21.7; 22.5; 22.9; 23.4; 24.2; 25.2; 27.9; wherein the XRDP is measured with a Copper X-ray source.

Embodiment 1(e) provides 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern corresponding to Crystalline Form 5, with a X-ray powder diffraction spectrum comprising 2θ values (in degrees) of about: 9.4; 11.9;

12.6; 13.7; 15.2; 15.3; 18.0; 18.9; 19.4; 20.1; 20.5; 20.7; 21.3; 22.8; 23.3; 23.9; 24.3; 25.4; 25.8; 27.3; 27.6; 28.1; 29.3; 29.8; wherein the XRDP is measured with a Copper X-ray source.

Embodiment 2 provides the solid of Embodiment 1(a), which comprises dichloromethane.

Embodiment 3 provides the solid of any of Embodiments 1(a) and 2, which is obtainable by crystallizing (I) free acid from dichloromethane.

Embodiment 4 provides the solid of Embodiment 1(b), which comprises toluene.

Embodiment 5 provides the solid of any of Embodiments 1(b) and 4, which is obtainable by crystallizing (I) free acid from toluene.

Embodiment 6 provides the solid of Embodiment 1(c), which comprises at least one selected from the group consisting of acetone and water.

Embodiment 7 provides the solid of any of Embodiments 1(c) and 6, which is obtainable by crystallizing (I) free acid from a mixture of acetone and water.

Embodiment 8 provides the solid of Embodiment 1(d), which comprises nitromethane.

Embodiment 9 provides the solid of any of Embodiments 1(d) and 8, which is obtainable by crystallizing (I) free acid from nitromethane.

Embodiment 10 provides the solid of Embodiment 1(e), which is obtainable by crystallizing (I) free acid from a mixture of ethanol and ethyl acetate.

Embodiment 11 provides the solid of any of Embodiments 1(e) and 10, wherein the mixture of ethanol and ethyl acetate ranges from about 1:10 to 10:1 ethanol/ethyl acetate.

Embodiment 12 provides the solid of any of Embodiments 1(e) and 10-11, wherein the mixture of ethanol and ethyl acetate ranges from about 1:3 to 3:1 ethanol/ethyl acetate.

Embodiment 13 provides the solid of Embodiment 1(a), further characterized by a Differential Scanning Calorimetry (DSC) thermogram having a single maximum value at about 99° C.

Embodiment 14 provides the solid of Embodiment 1(b), further characterized by a DSC thermogram having a single maximum value at about 123.8° C.

Embodiment 15 provides the solid of Embodiment 1(c), further characterized by a DSC thermogram having a single maximum value at about 89.6° C.

Embodiment 16 provides the solid of Embodiment 1(d), further characterized by a DSC thermogram having a single maximum value at about 110.3° C.

Embodiment 17 provides the solid of Embodiment 1(e), further characterized by a DSC thermogram having a single maximum value at about 175.9° C.

Embodiment 18 provides the solid of any of Embodiments 13-17, wherein the DSC measurement is performed by heating the solid from 25° C. at 10° C./min to at least 30° C. above the solid's melting point.

Embodiment 19 provides the solid of any of Embodiments 13-18, wherein the DSC measurement is performed with standard aluminum DSC sample pans and covers, with a nitrogen gas purge rate at about 50 ml/min.

Embodiment 20 provides a pharmaceutical composition comprising at least one pharmaceutically acceptable carrier and the solid of any of Embodiments 1-19.

Embodiment 21 provides the pharmaceutical composition of Embodiment 20, which is in solid dosage form for oral administration.

Embodiment 22 provides the pharmaceutical composition of any of Embodiments 20-21, which is part of a tablet, dragee, drop, suppository, capsule, caplet, and/or gelcap.

Embodiment 23 provides the pharmaceutical composition of any of Embodiments 20-22, which comprises about 30 mg of (I) free base, 200 mg of (I) free base, or any multiples or combinations thereof.

Embodiment 24 provides the pharmaceutical composition of any of Embodiments 20-23, further comprising at least one additional antiviral and/or anticancer agent.

Embodiment 25 provides a method of treating and/or preventing a disease or disorder caused by EBNA1 activity in a subject, the method comprising administering to the subject a therapeutically effective amount of the solid of any of Embodiments 1-19 and/or the pharmaceutical composition of any of Embodiments 20-24.

Embodiment 26 provides the method of Embodiment 25, wherein the solid and/or pharmaceutical composition is administered orally to the subject.

Embodiment 27 provides the method of any of Embodiments 25-26, wherein the disease or disorder is at least one selected from the group consisting of infectious mononucleosis, chronic fatigue syndrome, multiple sclerosis, systemic lupus erythematosus, and rheumatoid arthritis.

Embodiment 28 provides a method of treating and/or preventing a cancer caused by EBNA1 activity in a subject, the method comprising administering to the subject a therapeutically effective amount of the solid of any of Embodiments 1-19 and/or the pharmaceutical composition of any of Embodiments 20-24.

Embodiment 29 provides the method of Embodiment 28, wherein the cancer is at least one selected from the group consisting of nasopharyngeal carcinoma, gastric carcinoma, non-Hodgkin's lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmacytic lymphoma, nodal marginal zone B cell lymphoma, splenic marginal zone lymphoma, intravascular large B-cell lymphoma, primary effusion lymphoma, lymphomatoid granulomatosis, angioimmunoblastic lymphadenopathy, leiomyosarcomas, X-linked lymphoproliferative disease, post-transplant lymphoproliferative disorders, Hodgkin's lymphoma, and breast cancer.

Embodiment 30 provides the method of any of Embodiments 28-29, wherein the cancer is at least one selected from the group consisting of nasopharyngeal carcinoma, gastric carcinoma, non-Hodgkin's lymphoma, and post-transplant lymphoproliferative disorder (PTLD).

Embodiment 31 provides a method of treating and/or preventing Epstein-Barr Virus (EBV) infection, and/or a disease or disorder associated with EBV infection, in a subject, the method comprising administering to the subject a therapeutically effective amount of the solid of any of Embodiments 1-19 and/or the pharmaceutical composition of any of Embodiments s 20-24.

Embodiment 32 provides the method of Embodiment 31, wherein the solid and/or pharmaceutical composition is administered orally to the subject.

Embodiment 33 provides a method of treating and/or preventing lytic and/or latent EBV infection in a subject, the method comprising administering to the subject a therapeutically effective amount of the solid of any of Embodiments 1-19 and/or the pharmaceutical composition of any of Embodiments 20-24.

Embodiment 34 provides the method of Embodiment 33, wherein the solid and/or pharmaceutical composition is administered orally to the subject.

Embodiment 35 provides the method of any of Embodiments 25-34, wherein the solid and/or pharmaceutical composition is administered to the subject by at least one route selected from the group consisting of oral, nasal, inhalational, topical, buccal, rectal, pleural, peritoneal, vaginal, intramuscular, subcutaneous, transdermal, epidural, intratracheal, otic, intraocular, intrathecal, and intravenous routes.

Embodiment 36 provides the method of any of Embodiments 25-35, wherein the subject is further administered at least one additional antiviral and/or anticancer agent.

Embodiment 37 provides the method of any of Embodiments 25-36, wherein the subject is a mammal.

Embodiment 38 provides the method of any of Embodiments 25-37, wherein the mammal is human.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating or ameliorating a cancer caused by EBNA1 activity in a subject, the method comprising administering to the subject a therapeutically effective amount of 2-(1H-Indol-6-yl)-3-[4-(tetrahydro-pyran-4-yloxymethyl)-phenylethynyl]-benzoic acid (I) free acid crystalline solid, which is characterized by an X-ray powder diffraction (XRPD) pattern selected from the group consisting of:
  (a) Crystalline Form 1, with a X-ray powder diffraction spectrum comprising 2θ values (in degrees) of about: 6.9; 8.4; 9.8; 11.0; 12.8; 14.7; 15.3; 16.5; 16.9; 17.9; 18.2; 18.7; 19.0; 19.6; 20.0; 20.3; 20.9; 21.4; 22.2; 23.9; 24.5; 24.8; 25.4; 25.9; 26.1; 27.1; 4.7; 29.2; 29.7;
  (b) Crystalline Form 2, with a X-ray powder diffraction spectrum comprising 2θ values (in degrees) of about: 7.1; 7.9; 8.6; 9.4; 10.1; 10.5; 11.7; 12.7; 13.3; 14.3; 14.7; 15.0; 15.5; 16.0; 16.3; 16.6; 17.2; 17.8; 18.5; 18.9; 19.5; 20.3; 20.8; 21.6; 22.0; 22.7; 23.0; 23.5; 24.0; 24.6; 24.9; 25.6; 26.2; 26.7; 27.2; 27.8; 28.8; 29.2; 29.7;
  (c) Crystalline Form 3, with a X-ray powder diffraction spectrum comprising 2θ values (in degrees) of about: 6.8; 8.3; 12.5; 12.8; 13.7; 15.4; 16.8; 17.8; 19.0; 19.3; 19.9; 20.7; 21.3; 21.8; 22.2; 22.9; 23.6; 24.2; 25.3; 25.7; 26.2; 26.5; 27.6; 28.5; 29.0; 29.5;
  (d) Crystalline Form 4, with a X-ray powder diffraction spectrum comprising 2θ values (in degrees) of about: 7.7; 8.2; 10.6; 11.2; 15.3; 16.9; 17.7; 18.8; 19.5; 21.2; 21.7; 22.5; 22.9; 23.4; 24.2; 25.2; 27.9;
  (e) Crystalline Form 5, with a X-ray powder diffraction spectrum comprising 2θ values (in degrees) of about: 9.4; 11.9; 12.6; 13.7; 15.2; 15.3; 18.0; 18.9; 19.4; 20.1; 20.5; 20.7; 21.3; 22.8; 23.3; 23.9; 24.3; 25.4; 25.8; 27.3; 27.6; 28.1; 29.3; 29.8;
  wherein the XRPD is measured with a Copper X-ray source.

2. The method of claim 1, wherein the cancer is at least one selected from the group consisting of nasopharyngeal carcinoma, gastric carcinoma, non-Hodgkin's lymphoma, anaplastic large-cell lymphoma, angioimmunoblastic T-cell lymphoma, hepatosplenic T-cell lymphoma, B-cell lymphoma, Burkitt's lymphoma, reticuloendotheliosis, reticulosis, microglioma, diffuse large B-cell lymphoma, extranodal T/NK lymphoma/angiocentric lymphoma, follicular lymphoma, immunoblastic lymphoma, mucosa-associated lymphatic tissue lymphoma, B-cell chronic lymphocytic leukemia, mantle cell lymphoma, mediastinal large B cell lymphoma, lymphoplasmacytic lymphoma, nodal marginal zone B cell lymphoma, splenic marginal zone lymphoma, intravascular large B-cell lymphoma, primary effusion lymphoma, lymphomatoid granulomatosis, angioimmunoblastic lymphadenopathy, leiomyosarcomas, X-linked lymphoproliferative disease, post-transplant lymphoproliferative disorders, Hodgkin's lymphoma, and breast cancer.

3. The method of claim 1, wherein the cancer is at least one selected from the group consisting of nasopharyngeal carcinoma, gastric carcinoma, non-Hodgkin's lymphoma, and post-transplant lymphoproliferative disorder (PTLD).

4. The method of claim 1, wherein the (I) free acid crystalline solid is administered orally to the subject.

5. The method of claim 1, wherein the (I) free acid crystalline solid is administered to the subject by at least one route selected from the group consisting of oral, nasal, inhalational, topical, buccal, rectal, pleural, peritoneal, vaginal, intramuscular, subcutaneous, transdermal, epidural, intratracheal, otic, intraocular, intrathecal, and intravenous routes.

6. The method of claim 1, wherein the mammal is human, optionally the mammal is a human.

7. The method of claim 1, wherein the (I) free acid crystalline solid is formulated as a pharmaceutical composition.

8. The method of claim 7, wherein the pharmaceutical composition is in solid dosage form for oral administration.

9. The method of claim 7, wherein the pharmaceutical composition is part of a tablet, dragee, drop, suppository, capsule, caplet, or gelcap.

10. The method of claim 7, wherein the pharmaceutical composition comprises about 30 mg of (I) free base, 200 mg of (I) free base, or any multiples or combinations thereof.

* * * * *